United States Patent
Jakobi et al.

(10) Patent No.: US 8,252,723 B2
(45) Date of Patent: Aug. 28, 2012

(54) SUBSTITUTED 1-(3-PYRIDINYL)PYRAZOL-4-YLACETIC ACIDS, PROCESSES FOR THEIR PREPARATION AND THEIR USE AS HERBICIDES AND PLANT GROWTH REGULATORS

(75) Inventors: Harald Jakobi, Frankfurt (DE); Oswald Ort, Leverkusen (DE); Martin Hills, Idstein (DE); Heinz Kehne, Hofheim (DE); Christopher Rosinger, Hofheim (DE); Dieter Feucht, Eschborn (DE)

(73) Assignee: Bayer CropScience AG, Monheim (DE)

( * ) Notice: Subject to any disclaimer, the term of this patent is extended or adjusted under 35 U.S.C. 154(b) by 1187 days.

(21) Appl. No.: 11/965,185

(22) Filed: Dec. 27, 2007

(65) Prior Publication Data
US 2009/0036310 A1 Feb. 5, 2009

(30) Foreign Application Priority Data
Dec. 29, 2006 (EP) .................................. 06027044

(51) Int. Cl.
C07D 401/00 (2006.01)
C07D 231/10 (2006.01)
C07D 231/12 (2006.01)
A01N 43/00 (2006.01)
A01N 43/02 (2006.01)

(52) U.S. Cl. ..................................... 504/253; 546/275.4

(58) Field of Classification Search .................. 504/253; 546/275.4
See application file for complete search history.

(56) References Cited

U.S. PATENT DOCUMENTS

| | | | |
|---|---|---|---|
| 4,095,025 A | 6/1978 | Newberry | |
| 4,146,721 A | 3/1979 | Rainer | |
| 4,325,962 A * | 4/1982 | Rainer | ........................ 514/406 |
| 4,631,211 A | 12/1986 | Houghten | |
| 5,013,659 A | 5/1991 | Bedbrook et al. | |
| 2006/0264419 A1 | 11/2006 | Schiemann et al. | |
| 2007/0149406 A1 | 6/2007 | Bastiaans et al. | |

FOREIGN PATENT DOCUMENTS

| | | |
|---|---|---|
| DE | 21 41 124 A | 2/1972 |
| EP | 0 822 187 A1 | 2/1998 |
| WO | WO 2004/089931 A1 | 10/2004 |

OTHER PUBLICATIONS

International Search Report, Application No. PCT/EP2007/010649, dated Oct. 17, 2008, 3 pages.
Dialog File 351 Accession No. 447241, Derwent WPI English language abstract for DE 21 41 124 A (listed as document FP1 on accompanying form PTO/SB/08A), Feb. 24, 1972-publication date.

\* cited by examiner

*Primary Examiner* — Fereydoun G Sajjadi
*Assistant Examiner* — Courtney Brown
(74) *Attorney, Agent, or Firm* — Sterne, Kessler, Goldstein & Fox PLLC

(57) ABSTRACT

The invention relates to the use of compounds of the formula (I) or salts thereof

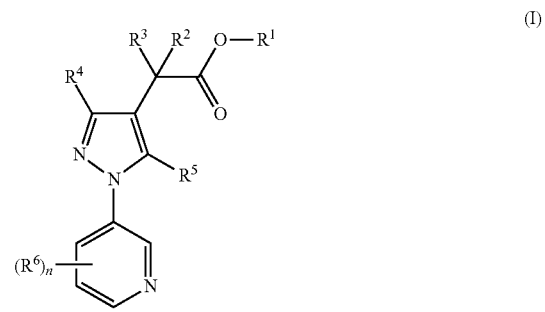

in which
$R^1$, $R^2$, $R^3$, $R^4$, $R^5$, $R^6$ and n are as defined in claim 1
as herbicides and plant growth regulators.
The invention also relates to novel compounds of the formula (I) and salts thereof (see claim 5).

7 Claims, No Drawings

SUBSTITUTED 1-(3-PYRIDINYL)PYRAZOL-4-YLACETIC ACIDS, PROCESSES FOR THEIR PREPARATION AND THEIR USE AS HERBICIDES AND PLANT GROWTH REGULATORS

This application claims priority to European Patent Application No. 06027044.4, filed Dec. 29, 2006 which is hereby incorporated by reference in its entirety.

The invention relates to the technical field of the herbicides and plant growth regulators, for example the herbicides for controlling broad-leaved weeds and weed grasses in crops of useful plants or the plant growth regulators which can be used for influencing the growth of crop plants.

In their application, crop protection agents known to date for the selective control of harmful plants in crops of useful plants or active compounds for controlling unwanted vegetation sometimes have disadvantages, be it (a) that they have low or else insufficient herbicidal activity against particular harmful plants, (b) that the spectrum of harmful plants which can be controlled with an active compound is not wide enough, (c) that their selectivity in crops of useful plants is too low or that they have a toxicologically unfavorable profile. Other active compounds which can be used as plant growth regulators for a number of useful plants cause unwanted reduced harvest yields in other useful plants or are not compatible with the crop plant, or only within a narrow application rate range. Other known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

Herbicidal 3-(hetero)aryl-4-[(hetero)arylcarbonyl]pyrazole compounds are known from EP-A-0822187 and the literature cited therein.

For the reasons mentioned, there is still a need for alternative, highly active herbicides for the selective application in plant crops and use on non-crop land. It is also desirable to prepare alternative chemically active compounds which, if appropriate, can be used advantageously as herbicides or plant growth regulators.

The present invention provides the use of compounds of the formula (I) or salts thereof

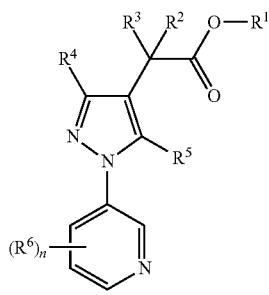

(I)

in which $R^1$ is hydrogen or a hydrolyzable radical, preferably hydrogen or an optionally substituted hydrocarbon radical or an optionally substituted heterocyclyl radical, where each of the two last mentioned carbon-containing radicals has, including substituents, 1 to 30 carbon atoms, preferably 1 to 24 carbon atoms, in particular 1 to 20 carbon atoms, or a radical of the formula $SiR^aR^bR^c$, $-NR^aR^b$ or $-N=CR^cR^d$, where in the 3 last mentioned formulae each of the radicals $R^a$, $R^b$, $R^c$ and $R^d$ independently of the others is hydrogen or an optionally substituted hydrocarbon radical or $R^a$ and $R^b$ together with the nitrogen atom are a 3- to 9-membered heterocycle which, in addition to the nitrogen atom, may contain one or two further hetero ring atoms from the group consisting of N, O and S and which is unsubstituted or substituted, or $R^c$ and $R^d$ together with the carbon atom are a 3- to 9-membered carbocyclic radical or a heterocyclic radical which may contain 1 to 3 hetero ring atoms from the group consisting of N, O and S, where the carbocyclic or heterocyclic radical is unsubstituted or substituted, where each of the radicals $R^a$, $R^b$, $R^c$ and $R^d$ including substituents has up to 30 carbon atoms, preferably up to 24 carbon atoms, in particular up to 20 carbon atoms, $R^2$ is hydrogen, halogen or $(C_1-C_6)$-alkyl which is unsubstituted or substituted by one or more radicals from the group consisting of halogen, $(C_1-C_4)$-alkoxy, $(C_1-C_4)$-alkylthio and $(C_1-C_4)$-haloalkoxy, $R^3$ is hydrogen, halogen or $(C_1-C_6)$-alkyl which is unsubstituted or substituted by one or more radicals from the group consisting of halogen, $(C_1-C_4)$-alkoxy, $(C_1-C_4)$-alkylthio and $(C_1-C_4)$-haloalkoxy, or $R^2$ and $R^3$ together with the carbon atom to which they are attached are a carbocyclic saturated or partially unsaturated ring having 3 to 6 carbon atoms which is unsubstituted or substituted by one or more radicals from the group consisting of halogen and $(C_1-C_4)$-alkyl, and $R^4$ is hydrogen, halogen, cyano, $(C_1-C_6)$-alkyl, $(C_2-C_6)$-alkenyl or $(C_2-C_6)$-alkynyl, where each of the three last mentioned radicals is unsubstituted or substituted by one or more radicals from the group consisting of halogen, cyano, hydroxyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_9)$-cycloalkyl, or preferably substituted by one or more radicals from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_9)$-cycloalkyl, or $(C_3-C_9)$-cycloalkyl, $(C_5-C_9)$-cycloalkenyl or $(C_5-C_9)$-cycloalkynyl, where each of the 3 last mentioned radicals is unsubstituted or substituted by one or more radicals from the group consisting of halogen, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy and $(C_1-C_4)$-alkylthio, or phenyl which is unsubstituted or substituted by one or more radicals from the group consisting of halogen, cyano, nitro, carboxyl, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_1-C_4)$-alkanoyl, $(C_1-C_4)$-haloalkanoyl, [$(C_1-C_4)$-alkoxy]carbonyl and [$(C_1-C_4)$-haloalkoxy]carbonyl, or $(C_1-C_6)$-alkanoyl which is unsubstituted or substituted by one or more radicals from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_6)$-cycloalkyl, or

[$(C_1-C_4)$-alkoxy]carbonyl which is unsubstituted or substituted by one or more radicals from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_6)$-cycloalkyl, or

[$(C_3-C_9)$-cycloalkoxy]carbonyl which is unsubstituted or substituted by one or more radicals from the group consisting of halogen, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy and $(C_1-C_4)$-alkylthio, $R^5$ is an aryl radical which is unsubstituted or, preferably, substituted and, including substituents, has 6 to 30 carbon atoms, preferably 6 to 24 carbon atoms, in particular 6 to 20 carbon atoms, or a heteroaromatic radical having 1 to 4 hetero ring atoms from the group consisting of N, O and S which is unsubstituted or substituted and, including substituents, has 1 to 30 carbon atoms, preferably 1 to 24 carbon atoms, in particular 1 to 20 carbon atoms, and $(R^6)_n$ are n substituents $R^6$, where $R^6$, in the case that n=1, or each of the substituents $R^6$ independently of the others, in the case that n is greater than 1, is a radical halogen, hydroxyl, amino, nitro, carboxyl, cyano, carbamoyl, $(C_1-C_6)$-alkyl, $(C_1-C_6)$-haloalkyl, $(C_1-C_4)$-alkoxy-$(C_1-C_4)$-alkyl, $(C_1-C_4)$-alkylthio-$(C_1-C_4)$-alkyl, mono- or di-[$(C_1-C_4)$-alkyl]aminoalkyl, hydroxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, [$(C_1-C_6)$-alkoxy]carbonyl, [$(C_1-C_6)$-haloalkoxy]carbonyl, $(C_1-C_6)$-alkanoyl, $(C_1-C_6)$-haloalkanoyl, mono- or di-[$(C_1-C_4)$-alkyl]aminocarbonyl, mono- or di-[$(C_1-C_6)$-acyl]amino, mono- or di-[$(C_1-C_4)$-alkyl]amino, N—[$(C_1-C_6)$-acyl]-N—[$(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_3-C_9)$-cycloalkyl or $(C_5-C_9)$-cycloalkenyl, where each of the two last mentioned radicals is unsubstituted or substituted by one or more radicals from the group consisting of halogen, $(C_1-C_4)$-alkyl and $(C_1-C_4)$-haloalkyl, and n is 0, 1, 2, 3 or 4, as herbicides or plant growth regulators.

By addition of a suitable inorganic or organic acid, such as, for example, HCl, HBr, $H_2SO_4$ or $HNO_3$, but also oxalic acid or sulfonic acids, onto a basic group, such as, for example, amino or alkylamino, the compounds of the formula (I) may form salts. Suitable substituents present in deprotonated form, such as, for example, sulfonic acids or carboxylic acids, may form inner salts with groups which for their part can be protonated, such as amino groups. Salts may also be formed by replacing the hydrogen of suitable substituents, such as, for example, sulfonic acids or carboxylic acids, by an agriculturally suitable cation. These salts are, for example, metal salts, in particular alkali metal salts or alkaline earth metal salts, especially sodium salts and potassium salts, or else ammonium salts, salts with organic amines or quaternary ammonium salts.

In the formula (I) and all subsequent formulae, terms for chemical radicals are used which have in particular the meanings illustrated below.

A hydrolyzable radical (see definition of $R^1$) is a radical which can be hydrolyzed under application conditions, for example a radical which can be hydrolyzed even in the spray liquor or in particular under the physiological conditions in plants, where a compound of the formula (I) having the carboxylic ester group —CO—$OR^1$ ($R^1$ is not hydrogen) is hydrolyzed to the compound of the formula (I) having the carboxylic acid group —CO—OH (i.e. the compound (I) where $R^1$=H). Expressly, the definition of the hydrolyzable radicals also includes radicals where $R^1$=hydrocarbon radical or heterocyclyl radical, the two last mentioned radicals being unsubstituted or substituted, even if some of them are hydrolyzable comparatively slowly.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc.; this applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified number of carbon atoms, for example "$(C_1-C_6)$-alkyl" correspondingly also include straight-chain or branched alkyl radicals having a larger number of carbon atoms, i.e., according to the example, also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in combined radicals. Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl. Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$-cycloalkyl or $(C_5-C_9)$-cycloalkenyl. $(C_3-C_9)$-Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5-C_9)$-Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$-alkylidene, is the radical of a straight-chain or branched alkane which is bonded via a double bond, the position of the binding site not being fixed. In the case of a branched alkane, of course, only positions at which two hydrogen atoms may be replaced by the double bond are possible; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are, respectively, alkyl, alkenyl and alkynyl substituted partly or fully by identical or different halogen atoms, preferably from the group of fluorine, chlorine and bromine, in particular from the group of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic; unless defined otherwise, it preferably contains one or more, in particular 1, 2 or 3, heteroatoms in the heterocyclic ring, preferably from the group of N, O and S; it is preferably an aliphatic heterocyclyl radical having from 3 to 7 ring atoms or a heteroaromatic radical having 5 or 6 ring atoms. The heterocyclic radical may, for example, be a heteroaromatic radical or ring (heteroaryl), for example a mono-, bi- or polycyclic aromatic system in which at least one ring contains one or more heteroatoms. It is preferably a heteroaromatic ring having a heteroatom from the group of N, O and S, for example pyridyl, pyrrolyl, thienyl or furyl; it is also preferably a corresponding heteroaromatic ring having 2 or 3 heteroatoms, for example pyrimidinyl, pyridazinyl, pyrazinyl, triazinyl, thiazolyl, thiadiazolyl, oxazolyl, isoxazolyl, pyrazolyl, imidazolyl and triazolyl. It is also preferably a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl. Possible substituents for a substituted heterocyclic radical include the substituents specified below, and additionally also oxo. The oxo group may also occur on the hetero ring atoms which may exist in various oxidation states, for example in the case of N and S.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon radicals mentioned, corresponding unsaturated aliphatic and aromatic radicals, such as optionally substituted alkenyl, alkynyl, alkenyloxy, alkynyloxy, phenyl, phenoxy, etc. In the case of substituted cyclic radicals having aliphatic moieties in the ring, cyclic systems with those substituents which are bonded on the ring by a double bond are also included, for example substituted by an alkylidene group such as methylidene or ethylidene.

The substituents mentioned by way of example ("first substituent level") may, when they contain hydrocarbon moieties, optionally be further substituted there ("second substituent level"), for example by one of the substituents as defined for the first substituent level. Corresponding further substituent levels are possible. The term "substituted radical" preferably includes only one or two substituent levels.

"Base radical" refers to the respective base structure of a radical to which substituents of a substituent level are attached.

Preferred substituents for the substituent levels are, for example,
amino, hydroxyl, halogen, nitro, cyano, mercapto, carboxyl, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkyl-aminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

Optionally substituted phenyl is preferably phenyl or phenyl which is unsubstituted or substituted by one or more radicals from the group consisting of halogen, cyano, $(C_1-C_4)$-alkyl, $(C_1-C_4)$-haloalkyl, $(C_1-C_4)$-alkoxy-$(C_1-C_4)$-alkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and nitro, in particular phenyl which is optionally substituted by one or more radicals from the group consisting of halogen, $(C_1-C_4)$-alkyl, $(C_1-C_4)$-haloalkyl and $(C_1-C_4)$-alkoxy.

In the case of radicals with carbon atoms, preference is given to those having from 1 to 6 carbon atoms, preferably from 1 to 4 carbon atoms, in particular 1 or 2 carbon atoms. In general, preferred substituents are those from the group of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably $(C_1-C_4)$-alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids. Acyl is, for example, formyl, alkylcarbonyl such as $[(C_1-C_4)$-alkyl]carbonyl, phenylcarbonyl, alkyloxycarbonyl, phenyloxycarbonyl, benzyloxycarbonyl, alkylsulfonyl, alkylsulfinyl, N-alkyl-1-aminoalkyl and other radicals of organic acids. The radicals may each be substituted further in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl. Acyl is preferably an acyl radical in the narrower sense, i.e. a radical of an organic acid in which the acid group is bonded directly to the carbon atom of an organic radical, for example formyl, alkylcarbonyl such as acetyl or $[(C_1-C_4)$-alkyl]carbonyl, phenylcarbonyl, alkylsulfonyl, alkylsulfinyl and other radicals of organic acids. More preferably, acyl is an alkanoyl radical having 1 to 6 carbon atoms, in particular 1 to 4 carbon atoms. Here, $(C_1-C_4)$-alkanoyl is the radical of an alkanoic acid having 1 to 4 carbon atoms after removal of the OH group of the acid group, i.e. formyl, acetyl, n-propionyl, i-propionyl or n-, i-, sec- or tert-butanoyl.

The "yl position" of a radical denotes the carbon atom having the free bond. Compounds of the formula (I) according to the invention and compounds of the formula (I) used according to the invention (and, if appropriate, salts thereof) are in short also referred to as "compounds (I)".

The invention also provides all stereoisomers which are encompassed by formula (I) and mixtures thereof. Such compounds of the formula (I) contain one or more asymmetric carbon atoms or else double bonds which are not stated specifically in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

For reasons of higher herbicidal action, better selectivity and/or better preparability in particular, inventive compounds of the formula (I) mentioned or salts thereof and their use according to the invention where individual radicals have one of the preferred definitions already mentioned or mentioned hereinafter, or especially those in which one or more of the preferred definitions already mentioned or mentioned hereinafter occur in combination are of particular interest.

Irrespective of the other radicals from the group of $R^1$, $R^2$, $R^3$, $R^4$, $R^5$ and $(R^6)_n$ in each case and the subdefinitions corresponding to the general radicals, and preferably in combination with preferred definitions of one or more of these radicals, inventive compounds or inventive uses of compounds of particular interest are those with the preferred definitions of the radicals in question listed below.

Preference is given to the use according to the invention of compounds of the formula (I) or salts thereof

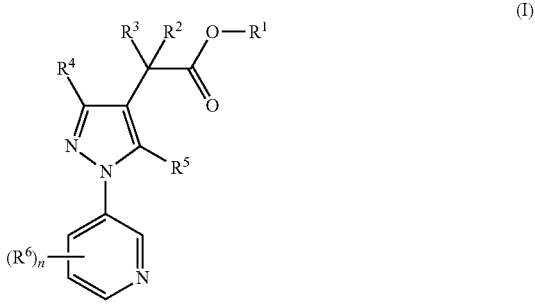

(I)

in which
$R^1$ is hydrogen, alkyl, alkenyl, alkynyl, cycloalkyl, cycloalkenyl, cycloalkynyl or aryl, where each of the 7 last mentioned radicals is unsubstituted or substituted and, including substituents, has up to 30 carbon atoms, preferably up to 24 carbon atoms, in particular up to 20 carbon atoms, or a heterocyclyl radical having 3 to 9 ring atoms which contains 1 to 4 heteroatoms from the group consisting of N, O and S, which is unsubstituted or substituted and which, including substituents, has 1 to 30 carbon atoms, preferably 1 to 24 carbon atoms, in particular 1 to 20 carbon atoms.

Here, more preference is also given to compounds (I) or salts thereof in which
$R^1$ is hydrogen.

Here, more preference is also given to compounds (I) or salts thereof in which
$R^1$ is H, $(C_1-C_{18})$-alkyl, $(C_2-C_{18})$-alkenyl, $(C_2-C_{18})$-alkynyl, $(C_3-C_9)$-cycloalkyl, $(C_5-C_{10})$-cycloalkenyl, $(C_5-C_9)$-cycloalkynyl or phenyl, where each of the 7 last mentioned radicals is unsubstituted or substituted and, including substituents, has up to 30 carbon atoms, preferably up to 24 carbon atoms, in particular up to 20 carbon atoms.

Here, more preference is also given to compounds (I) or salts thereof in which
$R^1$ is H, $(C_1-C_{18})$-alkyl, $(C_2-C_{18})$-alkenyl, $(C_2-C_{18})$-alkynyl, $(C_3-C_9)$-cycloalkyl, $(C_5-C_9)$-cycloalkenyl, $(C_5-C_9)$-cycloalkynyl or phenyl, where each of the 7 last mentioned radicals is unsubstituted or substituted by one or more radicals from the group consisting of halogen, cyano, thio, nitro, hydroxyl, $(C_1-C_8)$-alkyl, $(C_1-C_8)$-haloalkyl, $(C_1-C_4)$-alkoxy-$(C_1-C_4)$-alkyl, $(C_2-C_8)$-alkenyl, $(C_2-C_8)$-haloalkenyl, $(C_2-C_8)$-alkynyl, $(C_2-C_8)$-haloalkynyl, the 7 last mentioned radicals only in the case of cyclic base radicals, $(C_1-C_8)$-alkoxy, $(C_2-C_8)$-alkenyloxy, $(C_2-C_8)$-alkynyloxy, $(C_1-C_8)$-haloalkoxy, $(C_1-C_4)$-alkoxy-$(C_1-C_4)$-alkoxy, $(C_1-C_8)$-alkylthio, $(C_2-C_8)$-alkenylthio, $(C_2-C_8)$-alkynylthio, radicals of the formulae —NR*R**, —CO—NR*R** and —O—CO—NR*R**, where each of the radicals R and R in the 3 last mentioned formulae independently of the others is H, $(C_1-C_8)$-alkyl, $(C_2-C_8)$-alkenyl, $(C_2-C_8)$-alkynyl, benzyl, substituted benzyl, phenyl or substituted phenyl, or together with the nitrogen atom is a 3- to 8-membered heterocycle which, in addition to the nitrogen atom, may contain one or two further hetero ring atoms from the group consisting of N, O and S and which is unsubstituted or substituted by one or more radicals from the group consisting of $(C_1-C_4)$-alkyl and $(C_1-C_4)$-haloalkyl, and $[(C_1-C_8)$-alkoxy]carbonyl, $[(C_1-C_8)$-alkoxy]thiocarbonyl, $[(C_2-C_8)$-alkenyloxy]carbonyl, $[(C_2-C_8)$-alkynyloxy]carbonyl, $[(C_1-C_8)$-alkylthio]carbonyl, $[(C_2-C_8)$-alkenylthio]carbonyl, $[(C_2-C_8)$-alkynylthio]carbonyl, $(C_1-C_8)$-alkanoyl, $[(C_2-C_8)$-alkenyl]carbonyl, $[(C_2-C_8)$-alkynyl]carbonyl, $(C_1-C_4)$-alkylimino, $(C_1-C_4)$-alkoxyimino, $[(C_1-C_8)$-alkyl]carbonylamino, $[(C_2-C_8)$-alkenyl]carbonylamino, $[(C_2-C_8)$-alkynyl]carbonylamino, $[(C_1-C_8)$-alkoxy]carbonylamino, $[(C_2-C_8)$-alkenyloxy]carbonylamino, $[(C_2-C_8)$-alkynyloxy]carbonylamino, $[(C_1-C_8)$-alkylamino]carbonylamino, $[(C_1-C_6)$-alkyl]carbonyloxy, $[(C_2-C_6)$-alkenyl]carbonyloxy, $[(C_2-C_6)$-alkynyl]carbonyloxy, $[(C_1-C_8)$-alkoxy]carbonyloxy, $[(C_2-C_8)$-alkenyloxy]carbonyloxy, $[(C_2-C_8)$-alkynyloxy]carbonyloxy, $(C_1-C_8)$-alkylsulfinyl and $(C_1-C_8)$-alkylsulfonyl, where each of the 27 last mentioned radicals is unsubstituted or substituted by one or more radicals from the group consisting of halogen, $NO_2$, $(C_1-C_4)$-alkoxy and optionally substituted phenyl, and phenyl, phenyl-$(C_1-C_6)$-alkoxy, phenyl-$[(C_1-C_6)$-alkoxy]carbonyl, phenoxy, phenoxy-$(C_1-C_6)$-alkoxy, phenoxy-$[(C_1-C_6)$-alkoxy]carbonyl, phenoxycarbonyl, phenylcarbonyloxy, phenylcarbonylamino, phenyl-$[(C_1-C_6)$-alkyl]carbonylamino, phenyl-$[(C_1-C_6)$-alkyl]carbonyloxy, $(C_3-C_7)$-cycloalkyl and $(C_3-C_7)$-cycloalkoxy, where each of the 13 last mentioned radicals is unsubstituted in the ring or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and radicals of the formulae —SiR'$_{13}$, —O—SiR'$_{13}$, (R')$_3$Si—$(C_1-C_6)$-alkoxy, —CO—O—NR'$_2$, —O—N=CR'$_2$, —N=CR'$_2$, —O—NR'$_2$, —CH(OR')$_2$ and —O—$(CH_2)_m$—CH(OR')$_2$, in which each of the radicals R' independently of the others is H, $(C_1-C_4)$-alkyl or phenyl which is unsubstituted or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro or substituted in two adjacent positions by a $(C_2-C_6)$-alkylene bridge, and m is an integer of from 0 to 6, and radicals of the formula R"O—CHR'"CH(OR")—$(C_1-C_6)$-alkoxy, in which each of the radicals R" independently of the others is H or $(C_1-C_4)$-alkyl or the radicals R" together are a $(C_1-C_6)$-alkylene group and R'" is H or $(C_1-C_4)$-alkyl.

Here, more preference is also given to compound (I) or salts thereof in which $R^1$ is H, $(C_1-C_{12})$-alkyl, $(C_2-C_{12})$-alkenyl, $(C_2-C_{12})$-alkynyl, $(C_3-C_6)$-cycloalkyl, $(C_5-C_6)$-cycloalkenyl, $(C_5-C_6)$-cycloalkynyl or phenyl, where each of the 7 last mentioned radicals is unsubstituted or substituted by one or more radicals from the group consisting of halogen, cyano, thio, nitro, hydroxyl, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, the 7 last mentioned radicals only in the case of cyclic base radicals, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, radicals of the formulae —NR*R**, —CO—NR*R** and —O—CO—NR*R**.

where each of the radicals R* and R** in the 3 last mentioned formulae independently of the others is H, $(C_1-C_4)$-alkyl, $(C_2-C_4)$-alkenyl, $(C_2-C_4)$-alkynyl, benzyl, phenyl which is unsubstituted or substituted by one or more radicals from the group consisting of halogen, $(C_1-C_4)$-alkyl, $(C_1-C_4)$-haloalkyl and $(C_1-C_4)$-alkoxy, or together with the nitrogen atom is a piperidine, piperazine, pyrrolidine, pyrazolidine, piperazolidine or morpholine radical which is unsubstituted or substituted by one or more radicals from the group consisting of $(C_1-C_4)$-alkyl and $(C_1-C_4)$-haloalkyl, and $[(C_1-C_4)$-alkoxy]carbonyl, $[(C_1-C_4)$-alkyl]carbonylamino, $[(C_1-C_4)$-alkoxy]carbonylamino, $[(C_1-C_4$-alkylamino]carbonylamino, $[(C_1-C_4)$-alkyl]carbonyloxy, $[(C_1-C_4)$-alkoxy]carbonyloxy and $(C_1-C_4)$-alkylsulfonyl, where each of the 7 last mentioned radicals is unsubstituted or substituted by one or more radicals from the group consisting of halogen, $NO_2$, $(C_1-C_4)$-alkoxy and phenyl, which is unsubstituted or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and phenyl, phenyl-$(C_1-C_4)$-alkoxy, phenyl-$[(C_1-C_4)$-alkoxy]carbonyl, phenoxy, phenoxy-$(C_1-C_4)$-alkoxy, phenoxy-$[(C_1-C_4)$-alkoxy]carbonyl, phenoxycarbonyl, phenylcarbonyloxy, phenylcarbonylamino, phenyl-$[(C_1-C_4)$-alkyl]carbonylamino, phenyl-$[(C_1-C_4)$-alkyl]carbonyloxy, $(C_3-C_6)$-cycloalkyl and $(C_3-C_6)$-cycloalkoxy, where each of the 13 last mentioned radicals is unsubstituted in the ring or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and radicals of the formulae —CO—O—NR'$_2$, —O—N=CR'$_2$, —N=CR'$_2$, —O—NR'$_2$, —CH(OR')$_2$ and —O—$(CH_2)_m$—CH(OR')$_2$, in which each of the radicals R' independently of the others is H, $(C_1-C_4)$-alkyl or phenyl which is unsubstituted or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro or is substituted in two adjacent positions by a $(C_2-C_6)$-alkylene bridge, and m is an integer of from 0 to 6, and radicals of the formula R"O—CHR'"CH(OR")—$(C_1-C_6)$-alkoxy, in which each of the radicals R" independently of the others is H or $(C_1-C_4)$-alkyl or the radicals R" together are a $(C_1-C_4)$-alkylene group and R'" is H or $(C_1-C_2)$-alkyl.

Here, more preference is also given to compounds (I) or salts thereof in which $R^1$ is H, $(C_1-C_6)$-alkyl, $(C_2-C_6)$-alkenyl, $(C_2-C_6)$-alkynyl or $(C_3-C_6)$-cycloalkyl, where each of the 4 last mentioned radicals is unsubstituted or substituted by one or more radicals from the group consisting of halogen, $(C_1-C_6)$-alkyl, the latter only a substituent in the case of cyclic base radicals, $(C_1-C_4)$-alkoxy, $(C_1-C_4)$-alkylthio, $(C_3-C_6)$-cycloalkyl which is unsubstituted or substituted by one or more radicals from the group consisting of halogen and $(C_1-C_4)$-alkyl, and phenyl which is unsubstituted or substituted by one or more radicals from the group consisting of halogen, $(C_1-C_4)$-alkyl, $(C_1-C_4)$-alkoxy and $(C_1-C_4)$-haloalkyl.

Here, particular preference is also given to compounds (I) or salts thereof in which $R^1$ is H, $(C_1-C_4)$-alkyl, $(C_2-C_4)$-alkenyl or $(C_2-C_4)$-alkynyl, where each of the 3 last mentioned radicals is unsubstituted or substituted by one or more radicals from the group consisting of halogen, $(C_1-C_4)$-alkoxy, $(C_1-C_4)$-alkylthio, cyclopropyl, cyclobutyl, where each of the two last mentioned radicals is unsubstituted or substituted by one or more radicals from the group consisting of halogen and $(C_1-C_4)$-alkyl, and phenyl which is unsubstituted or substituted by one or more radicals from the group consisting of halogen, $(C_1-C_4)$-alkyl, $(C_1-C_4)$-alkoxy and $(C_1-C_4)$-haloalkyl, very particularly $R^1$ is H, methyl, ethyl, n-propyl, i-propyl, benzyl, cyclopropylmethyl, 1-cyclopropylethyl, (1-methylcyclopropyl)methyl, (2,2-dimethylcyclopropyl)-methyl, allyl, propargyl, 2-chloroprop-2-en-1-yl, 3-phenylprop-2-yn-1-yl, 3,3-dichloroprop-2-en-1-yl, 3,3-dichloro-2-fluoroprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-2-en-1-yl, (E)-pent-3-en-2-yl or (Z)-pent-3-en-2-yl.

Preference is also given to compounds (I) or salts thereof in which $R^1$ is a saturated, partially unsaturated or heteroaromatic heterocyclyl radical having 3 to 9 ring atoms, preferably 5 or 6 ring atoms, which contains 1 to 4 heteroatoms, preferably 1 to 3 hetero ring atoms, from the group consisting of N, O and S and which is unsubstituted or substituted by one or more radicals from the group consisting of halogen, cyano, thio, nitro, hydroxyl, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl and oxo.

Preference is also given to compounds (I) or salts thereof in which $R^1$ is a radical of the formula $SiR^aR^bR^c$, —$NR^aR^b$ or —N=$CR^cR^d$, preferably of the formula —$NR^aR^b$ or —N=$CR^cR^d$, where in the 5 last mentioned formulae each of the radicals $R^a$, $R^b$, $R^c$ and $R^d$ independently of the others is hydrogen, $(C_1-C_4)$-alkyl, $(C_2-C_4)$-alkenyl, $(C_2-C_4)$-alkynyl, benzyl, substituted benzyl, phenyl or substituted phenyl or $R^a$ and $R^b$ together with the nitrogen atom are a 3- to 8-membered heterocycle which, in addition to the nitrogen atom, may contain one or two further hetero ring atoms from the group consisting of N, O and S and which is unsubstituted or substituted by one or more radicals from the group consisting of $(C_1-C_4)$-alkyl and $(C_1-C_4)$-haloalkyl, or $R^c$ and $R^d$ together with the carbon atom are a 3- to 8-membered carbocyclic radical or heterocyclic radical which may contain 1 to 3 hetero ring atoms from the group consisting of N, O and S, where the carbocyclic or heterocyclic radical is unsubstituted or substituted by one or more radicals from the group consisting of $(C_1-C_4)$-alkyl and $(C_1-C_4)$-haloalkyl.

Preference is also given to the use of compounds of the formula (I) or salts thereof in which $R^2$ is hydrogen, halogen or $(C_1-C_4)$-alkyl which is unsubstituted or substituted by one or more radicals from the group consisting of halogen, such as fluorine or chlorine, preferably hydrogen or $(C_1-C_4)$-alkyl, in particular hydrogen, methyl or ethyl, very particularly hydrogen or methyl.

Preference is also given to the use of compounds of the formula (I) or salts thereof in which $R^3$ is hydrogen, halogen or $(C_1-C_4)$-alkyl which is unsubstituted or substituted by one or more radicals from the group consisting of halogen, such as fluorine or chlorine, preferably hydrogen or $(C_1-C_4)$-alkyl, in particular hydrogen or methyl, very particularly hydrogen.

Preference is also given to the use of compounds of the formula (I) or salts thereof in which $R^2$ and $R^3$ together with the carbon atom to which they are attached are $(C_3-C_6)$-cycloalkyl or $(C_5-C_6)$-cycloalkenyl, preferably $(C_3-C_6)$-cycloalkyl, where each of the 3 last mentioned radicals is unsubstituted or substituted by one or more radicals from the group consisting of halogen and $(C_1-C_4)$-alkyl.

Here, preferably, $R^2$ and $R^3$ together with the carbon atom to which they are attached are cyclopropyl, cyclobutyl, cyclopentyl or cyclohexyl, in particular cyclopropyl, where each of the 4 last mentioned radicals is unsubstituted or substituted by one or more radicals from the group consisting of halogen and methyl, preferably fluorine, chlorine and methyl.

Preference is also given to the use of compounds of the formula (I) or salts thereof in which $R^4$ is hydrogen, halogen, cyano, $(C_1-C_4)$-alkyl, $(C_2-C_4)$-alkenyl or $(C_2-C_4)$-alkynyl, where each of the three last mentioned radicals is unsubstituted or substituted by one or more radicals from the group consisting of halogen and hydroxyl, preferably unsubstituted or substituted by one or more radicals from the group consisting of halogen, such as fluorine and chlorine, or $(C_3-C_6)$-cycloalkyl which is unsubstituted or substituted by one or more radicals from the group consisting of halogen and $(C_1-C_4)$-alkyl, or phenyl which is unsubstituted or substituted by one or more radicals from the group consisting of halogen, nitro, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, [$(C_1-C_4)$-alkoxy]carbonyl and [$(C_1-C_4)$-haloalkoxy]carbonyl, or $(C_1-C_4)$-alkanoyl which is unsubstituted or substituted by one or more radicals from the group consisting of halogen, such as fluorine and chlorine, cyano, $(C_1-C_4)$-alkoxy, $(C_1-C_4)$-haloalkoxy and $(C_1-C_2)$-alkoxy-$(C_1-C_2)$-alkoxy, preferably formyl, or

[(C$_1$-C$_4$)-alkoxy]carbonyl which is unsubstituted or substituted by one or more radicals from the group consisting of halogen, such as fluorine and chlorine, or

[(C$_3$-C$_6$)-cycloalkoxy]carbonyl which is unsubstituted or substituted by one or more radicals from the group consisting of halogen and (C$_1$-C$_4$)-alkyl.

More preference is also given to the use of compounds of the formula (I) or salts thereof in which R$^4$ is hydrogen, halogen, such as fluorine or chlorine, cyano, (C$_1$-C$_4$)-alkyl which is optionally substituted by hydroxyl [=(C$_1$-C$_4$)-hydroxyalkyl], (C$_1$-C$_4$)-haloalkyl, cyclopropyl or cyclobutyl, where each of the two last mentioned radicals is unsubstituted or substituted by one or more radicals from the group consisting of halogen, such as fluorine and chlorine, and (C$_1$-C$_4$)-alkyl, or phenyl which is unsubstituted or substituted by one or more radicals from the group consisting of halogen, (C$_1$-C$_4$)-alkyl, (C$_1$-C$_4$)-haloalkyl, (C$_1$-C$_4$)-alkoxy and (C$_1$-C$_4$)-alkylthio, or (C$_1$-C$_4$)-alkanoyl which is unsubstituted or substituted by one or more radicals from the group consisting of halogen, such as fluorine and chlorine, preferably formyl, or [(C$_1$-C$_4$)-alkoxy]carbonyl or [(C$_1$-C$_4$)-haloalkoxy]carbonyl, preferably R$^4$ is hydrogen, halogen, such as fluorine or chlorine, cyano, methyl, ethyl, n-propyl, i-propyl, CH$_2$Cl, CHCl$_2$, CCl$_3$, CH$_2$F, CHF$_2$, CF$_3$ or formyl.

Here, more preference is given to the abovementioned preferred or particularly preferred uses of compounds (I) or salts thereof in which R$^4$ is cyano or in which R$^4$ has one of the other meanings mentioned, other than cyano or formyl.

More preferably, R$^4$ is one of the radicals mentioned for R$^4$ and is different from hydrogen.

Preference is also given to the use of compounds of the formula (I) or salts thereof in which R$^5$ is phenyl which is unsubstituted or, preferably, substituted and, including substituents, has 6 to 24 carbon atoms, in particular 6 to 20 carbon atoms, or a 5- or 6-membered heteroaromatic radical having 1 to 3 hetero ring atoms from the group consisting of N, O and S which is unsubstituted or substituted and, including substituents, has 1 to 24 carbon atoms, in particular 1 to 20 carbon atoms.

More preference is also given to the use of compounds of the formula (I) or salts thereof in which R$^5$ is phenyl which is unsubstituted or, preferably, substituted by one or more radicals from the group consisting of halogen, hydroxyl, amino, nitro, carboxyl, cyano, carbamoyl, (C$_1$-C$_6$)-alkyl, (C$_1$-C$_6$)-haloalkyl, (C$_1$-C$_4$)-alkoxy-(C$_1$-C$_4$)-alkyl, (C$_1$-C$_4$)-alkylthio-(C$_1$-C$_4$)-alkyl, mono- and di-[(C$_1$-C$_4$)-alkyl]aminoalkyl, hydroxy-(C$_1$-C$_4$)-alkyl, carboxy-(C$_1$-C$_4$)-alkyl, cyano-(C$_1$-C$_4$)-alkyl, (C$_1$-C$_6$)-alkoxy which may optionally also be halogenated [=(C$_1$-C$_6$)-haloalkoxy], (C$_1$-C$_4$)-alkoxy-(C$_1$-C$_4$)-alkoxy, (C$_1$-C$_6$)-alkylthio, [(C$_1$-C$_6$)-alkoxy]carbonyl, [(C$_1$-C$_6$)-haloalkoxy]carbonyl, (C$_1$-C$_6$)-alkanoyl, (C$_1$-C$_6$)-haloalkanoyl, mono- and di-[(C$_1$-C$_4$)-alkyl]aminocarbonyl, mono- and di-[(C$_1$-C$_6$)-acyl]amino, mono- and di-[(C$_1$-C$_4$)-alkyl]amino, N—[(C$_1$-C$_6$)-acyl]-N—[(C$_1$-C$_6$)-alkyl]amino, (C$_1$-C$_6$)-alkylsulfinyl, (C$_1$-C$_6$)-haloalkylsulfinyl, (C$_1$-C$_6$)-alkylsulfonyl, (C$_1$-C$_6$)-haloalkylsulfonyl, (C$_3$-C$_6$)-cycloalkyl, (C$_3$-C$_6$)-cycloalkyloxy, phenyl and phenoxy, where each of the 4 last mentioned radicals is unsubstituted or substituted by one or more radicals from the group consisting of halogen, (C$_1$-C$_4$)-alkyl and (C$_1$-C$_4$)-haloalkyl, and where two adjacent substituents may form a fused-on 5- or 6-membered ring which is carbocyclic or may additionally contain 1 to 3 hetero ring atoms from the group consisting of N, O and S and which is unsubstituted or substituted by one or more radicals from the group consisting of halogen and (C$_1$-C$_6$)-alkyl, or R$^5$ is a 5- or 6-membered heteroaromatic ring having 1 to 3 hetero ring atoms from the group consisting of N, O and S, which is unsubstituted or substituted by one or more radicals from the group consisting of halogen, hydroxyl, amino, nitro, carboxyl, cyano, carbamoyl, (C$_1$-C$_6$)-alkyl, (C$_1$-C$_6$)-haloalkyl, (C$_1$-C$_4$)-alkoxy-(C$_1$-C$_4$)-alkyl, (C$_1$-C$_4$)-alkylthio-(C$_1$-C$_4$)-alkyl, mono- and di-[(C$_1$-C$_4$)-alkyl]aminoalkyl, hydroxy-(C$_1$-C$_4$)-alkyl, carboxy-(C$_1$-C$_4$)-alkyl, cyano-(C$_1$-C$_4$)-alkyl, (C$_1$-C$_6$)-alkoxy which may optionally also be halogenated [=(C$_1$-C$_6$)-haloalkoxy], (C$_1$-C$_4$)-alkoxy-(C$_1$-C$_4$)-alkoxy, (C$_1$-C$_6$)-alkylthio, [(C$_1$-C$_6$)-alkoxy]carbonyl, [(C$_1$-C$_6$)-haloalkoxy]carbonyl, (C$_1$-C$_6$)-alkanoyl, (C$_1$-C$_6$)-haloalkanoyl, mono- and di-[(C$_1$-C$_4$)-alkyl]aminocarbonyl, mono- and di-[(C$_1$-C$_6$)-acyl]amino, mono- and di-[(C$_1$-C$_4$)-alkyl]amino, N—[(C$_1$-C$_6$)-acyl]-N—[(C$_1$-C$_6$)-alkyl]amino, (C$_1$-C$_6$)-alkylsulfinyl, (C$_1$-C$_6$)-haloalkylsulfinyl, (C$_1$-C$_6$)-alkylsulfonyl, (C$_1$-C$_6$)-haloalkylsulfonyl, (C$_3$-C$_6$)-cycloalkyl, (C$_3$-C$_6$)-cycloalkyloxy, phenyl and phenoxy, where each of the 4 last mentioned radicals is unsubstituted or substituted by one or more radicals from the group consisting of halogen, (C$_1$-C$_4$)-alkyl and (C$_1$-C$_4$)-haloalkyl.

Here, more preference is also given to the use of compounds of the formula (I) or salts thereof in which R$^5$ is phenyl which is unsubstituted or, preferably, substituted by one or more radicals from the group consisting of halogen, hydroxyl, nitro, carboxyl, cyano, (C$_1$-C$_4$)-alkyl, (C$_1$-C$_4$)-haloalkyl, (C$_1$-C$_4$)-alkoxy-(C$_1$-C$_4$)-alkyl, (C$_1$-C$_4$)-alkylthio-(C$_1$-C$_4$)-alkyl, hydroxy-(C$_1$-C$_4$)-alkyl, (C$_1$-C$_4$)-alkoxy which may optionally also be halogenated [=(C$_1$-C$_4$)-haloalkoxy], (C$_1$-C$_4$)-alkoxy-(C$_1$-C$_4$)-alkoxy, (C$_1$-C$_4$)-alkylthio, [(C$_1$-C$_4$)-alkoxy]carbonyl, [(C$_1$-C$_4$)-haloalkoxy]carbonyl, (C$_1$-C$_4$)-alkylsulfinyl, (C$_1$-C$_4$)-haloalkylsulfinyl, (C$_1$-C$_4$)-alkylsulfonyl, (C$_1$-C$_4$)-haloalkylsulfonyl, (C$_3$-C$_6$)-cycloalkyl, (C$_3$-C$_6$)-cycloalkyloxy, phenyl and phenoxy, where each of the 4 last mentioned radicals is unsubstituted or substituted by one or more radicals from the group consisting of halogen, (C$_1$-C$_4$)-alkyl and (C$_1$-C$_4$)-haloalkyl, and where two adjacent substituents may form a fused-on 5- or 6-membered ring which is carbocyclic and may additionally contain 1 to 3 hetero ring atoms from the group consisting of N, O and S and which is unsubstituted or substituted by one or more radicals from the group consisting of halogen and (C$_1$-C$_4$)-alkyl, or R$^5$ is a 5- or 6-membered heteroaromatic radical having 1 to 3 hetero ring atoms from the group consisting of N, O and S, which is unsubstituted or substituted by one or more radicals from the group consisting of halogen, hydroxyl, carboxyl, cyano, (C$_1$-C$_4$)-alkyl, (C$_1$-C$_4$)-haloalkyl, (C$_1$-C$_4$)-alkoxy-(C$_1$-C$_4$)-alkyl, (C$_1$-C$_4$)-alkylthio-(C$_1$-C$_4$)-alkyl, hydroxy-(C$_1$-C$_4$)-alkyl, (C$_1$-C$_4$)-alkoxy which may optionally also be halogenated [=(C$_1$-C$_4$)-haloalkoxy], (C$_1$-C$_4$)-alkoxy-(C$_1$-C$_4$)-alkoxy, (C$_1$-C$_4$)-alkylthio, [(C$_1$-C$_6$)-alkoxy]carbonyl, [(C$_1$-C$_6$)-haloalkoxy]carbonyl, (C$_1$-C$_4$)-alkylsulfinyl, (C$_1$-C$_4$)-haloalkylsulfinyl, (C$_1$-C$_4$)-alkylsulfonyl, (C$_1$-C$_4$)-haloalkylsulfonyl and (C$_3$-C$_6$)-cycloalkyl which is unsubstituted or substituted by one or more radicals from the group consisting of halogen, (C$_1$-C$_4$)-alkyl and (C$_1$-C$_4$)-haloalkyl.

Here, even more preference is also given to the use of compounds of the formula (I) or salts thereof in which
$R^5$ is phenyl which is unsubstituted or, preferably, substituted by one or more radicals from the group consisting of halogen, cyano, (C$_1$-C$_4$)-alkyl, (C$_1$-C$_4$)-haloalkyl, (C$_1$-C$_4$)-alkoxy and (C$_1$-C$_4$)-alkylthio,
or
$R^5$ is a 5- or 6-membered heteroaromatic radical having 1 to 3 hetero ring atoms from the group consisting of N, O and S,
  which is unsubstituted or substituted by one or more radicals from the group consisting of halogen, hydroxyl, (C$_1$-C$_4$)-alkyl, (C$_1$-C$_4$)-haloalkyl, (C$_1$-C$_4$)-alkoxy and (C$_1$-C$_4$)-alkylthio.

Here, particular preference is given to the use of compounds of the formula (I) or salts thereof in which
$R^5$ is phenyl which is unsubstituted or, preferably, substituted by one or more radicals from the group consisting of halogen, such as fluorine, chlorine, bromine and iodine, cyano, methyl, ethyl, n-propyl, i-propyl, n-butyl, sec-butyl, i-butyl, t-butyl, CF$_3$, CCl$_3$, methoxy and ethoxy,
preferably
$R^5$ is phenyl, 2-fluorophenyl, 2-chlorophenyl, 2-bromophenyl, 2-iodophenyl, 2-methylphenyl, 2-CF$_3$-phenyl, 2-methoxyphenyl, 3-fluorophenyl, 3-chlorophenyl, 3-bromophenyl, 3-iodophenyl, 3-methylphenyl, 3-CF$_3$-phenyl, 3-methoxyphenyl, 4-fluorophenyl, 4-chlorophenyl, 4-bromophenyl, 4-iodophenyl, 4-methylphenyl, 4-CF$_3$-phenyl, 4-methoxyphenyl, 2,3-dichlorophenyl, 2,3-dimethylphenyl, 2,4-dichlorophenyl, 2,4-dimethylphenyl, 2,5-dichlorophenyl, 2,5-dimethylphenyl, 2,6-dichlorophenyl, 2,6-dimethylphenyl, 3,4-dichlorophenyl, 3,4-dimethylphenyl, 3,5-dichlorophenyl, 3,5-dimethylphenyl, 2-chloro-3-methylphenyl, 2-chloro-4-methylphenyl, 2-chloro-5-methylphenyl, 2-chloro-6-methylphenyl, 3-chloro-4-methylphenyl, 3-chloro-5-methylphenyl, 3-chloro-2-methylphenyl, 4-chloro-2-methylphenyl, 4-chloro-3-methylphenyl or 5-chloro-2-methylphenyl.

Here, preference is also given to the use of compounds of the formula (I) or salts thereof in which
$R^5$ is 2-pyridyl, 3-pyridyl, 4-pyridyl, 2-thienyl, 3-thienyl, 2-furyl, 3-furyl, 2-pyrrolyl, 3-pyrrolyl, 2-pyrimidinyl, 4-pyrimidinyl, 5-pyrimidinyl, 3-pyridazinyl, 4-pyridazinyl, 2-pyrazinyl, 3-pyrazinyl, 2-imidazolinyl, 4-imidazolinyl, 1-pyrazolyl, 3-pyrazolyl, 4-pyrazolyl, 5-pyrazolyl, 1,3,5-triazin-2-yl, 1,2,4-triazin-3-yl, 1,2,4-triazin-5-yl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, thiadiazolyl or triazolyl, preferably 2-pyridyl, 3-pyridyl, 4-pyridyl, 2-thienyl, 3-thienyl or 2-furyl, where each of the heteroaromatic radicals mentioned above is unsubstituted or substituted, preferably substituted by the radicals which have already been mentioned above as being preferred, in particular by one or more radicals from the group consisting of halogen, hydroxyl, (C$_1$-C$_4$)-alkyl, (C$_1$-C$_4$)-haloalkyl, (C$_1$-C$_4$)-alkoxy, (C$_1$-C$_4$)-alkylthio.

Here, particular preference is also given to the use of compounds of the formula (I) or salts thereof in which
$R^5$ is 2-pyridyl, 3-fluoropyrid-2-yl, 3-chloropyrid-2-yl, 3-bromopyrid-2-yl, 3-methylpyrid-2-yl, 3-methoxypyrid-2-yl, 3-trifluoromethylpyrid-2-yl, 4-fluoropyrid-2-yl, 4-chloropyrid-2-yl, 4-bromopyrid-2-yl, 4-methylpyrid-2-yl, 4-methoxypyrid-2-yl, 4-trifluoromethylpyrid-2-yl, 5-fluoropyrid-2-yl, 5-chloropyrid-2-yl, 5-bromopyrid-2-yl, 5-methylpyrid-2-yl, 5-methoxypyrid-2-yl, 5-trifluoromethylpyrid-2-yl, 6-fluoropyrid-2-yl, 6-chloropyrid-2-yl, 6-bromopyrid-2-yl, 6-methylpyrid-2-yl, 6-methoxypyrid-2-yl, 6-trifluoromethylpyrid-2-yl, 3-pyridyl, 2-fluoropyrid-3-yl, 2-chloropyrid-3-yl, 2-bromopyrid-3-yl, 2-methylpyrid-3-yl, 2-methoxypyrid-3-yl, 2-trifluoromethylpyrid-3-yl, 4-fluoropyrid-3-yl, 4-chloropyrid-3-yl, 4-bromopyrid-3-yl, 4-methylpyrid-3-yl, 4-methoxypyrid-3-yl, 4-trifluoromethylpyrid-3-yl, 5-fluoropyrid-3-yl, 5-chloropyrid-3-yl, 5-bromopyrid-3-yl, 5-methylpyrid-3-yl, 5-methoxypyrid-3-yl, 5-trifluoromethylpyrid-3-yl, 6-fluoropyrid-3-yl, 6-chloropyrid-3-yl, 6-bromopyrid-3-yl, 6-methylpyrid-3-yl, 6-methoxypyrid-3-yl, 6-trifluoromethylpyrid-3-yl, 4-pyridyl, 2-fluoropyrid-4-yl, 2-chloropyrid-4-yl, 2-bromopyrid-4-yl, 2-methylpyrid-4-yl, 2-methoxypyrid-4-yl, 2-trifluoromethylpyrid-4-yl, 3-fluoropyrid-4-yl, 3-chloropyrid-4-yl, 3-bromopyrid-4-yl, 3-methylpyrid-3-yl, 3-methoxypyrid-4-yl, 3-trifluoromethylpyrid-4-yl, 2-thienyl, 3-fluorothien-2-yl, 3-chlorothien-2-yl, 3-bromothien-2-yl, 3-methylthien-2-yl, 3-methoxythien-2-yl, 3-trifluoromethylthien-2-yl, 4-fluorothien-2-yl, 4-chlorothien-2-yl, 4-bromothien-2-yl, 4-methylthien-2-yl, 4-methoxythien-2-yl, 4-trifluoromethylthien-2-yl, 5-fluorothien-2-yl, 5-chlorothien-2-yl, 5-bromothien-2-yl, 5-methylthien-2-yl, 5-methoxythien-2-yl, 5-trifluoromethylthien-2-yl, 3-thienyl, 2-fluorothien-3-yl, 2-chlorothien-3-yl, 2-bromothien-3-yl, 2-methylthien-3-yl, 2-methoxythien-3-yl, 2-trifluoromethylthien-3-yl, 4-fluorothien-3-yl, 4-chlorothien-3-yl, 4-bromothien-3-yl, 4-methylthien-3-yl, 4-methoxythien-3-yl, 4-trifluoromethylthien-3-yl, 5-fluorothien-3-yl, 5-chlorothien-3-yl, 5-bromothien-3-yl, 5-methylthien-3-yl, 5-methoxythien-3-yl, 5-trifluoromethylthien-3-yl, 2-furyl, 3-fluorofur-2-yl, 3-chlorofur-2-yl, 3-bromofur-2-yl, 3-methylfur-2-yl, 3-methoxyfur-2-yl, 3-trifluoromethylfur-2-yl, 4-fluorofur-2-yl, 4-chlorofur-2-yl, 4-bromofur-2-yl, 4-methylfur-2-yl, 4-methoxyfur-2-yl, 4-trifluoromethylfur-2-yl, 5-fluorofur-2-yl, 5-chlorofur-2-yl, 5-bromofur-2-yl, 5-methylfur-2-yl, 5-methoxyfur-2-yl or 5-trifluoromethylfur-2-yl,
preferably
$R^5$ is 2-pyridyl, 5-fluoropyrid-2-yl, 5-chloropyrid-2-yl, 5-bromopyrid-2-yl, 5-methylpyrid-2-yl, 5-methoxypyrid-2-yl, 5-trifluoromethylpyrid-2-yl, 3-pyridyl, 6-fluoropyrid-3-yl, 6-chloropyrid-3-yl, 6-bromopyrid-3-yl, 6-methylpyrid-3-yl, 6-methoxypyrid-3-yl or 6-trifluoromethylpyrid-3-yl, 2-thienyl, 3-chlorothien-2-yl, 3-methylthien-2-yl, 4-chlorothien-2-yl, 4-methylthien-2-yl, 5-chlorothien-2-yl, 5-bromothien-2-yl or 5-methylthien-2-yl
or else 4-fluoropyrid-2-yl, 4-chloropyrid-2-yl, 4-bromopyrid-2-yl, 4-methylpyrid-2-yl or 4-trifluoropyrid-2-yl.

Preference is also given to the use of compounds of the formula (I) or salts thereof in which
$(R^6)_n$ are n substituents $R^6$, where $R^6$, in the case that n=1, or each of the substituents $R^6$ independently of the others, in the case that n is greater than 1, is a radical halogen, ($C_1$-$C_4$)-alkyl, ($C_1$-$C_4$)-haloalkyl, ($C_1$-$C_4$)-alkoxy, ($C_1$-$C_4$)-alkylthio, ($C_1$-$C_4$)-alkylsulfinyl, ($C_1$-$C_4$)-haloalkylsulfinyl, ($C_1$-$C_4$)-alkylsulfonyl or ($C_1$-$C_4$)-haloalkylsulfonyl, and n is 0, 1, 2, 3 or 4, preferably 0, 1 or 2.

Here, preference is also given to the use of compounds of the formula (I) or salts thereof in which $(R^6)_n$ are n substituents $R^6$, where $R^6$, in the case that n=1, or each of the substituents $R^6$ independently of the others, in the case that n is greater than 1, is a radical halogen, such as fluorine, chlorine, bromine or iodine, methyl, ethyl, $CF_3$, methoxy, ethoxy, methylthio, methylsulfinyl, ethylsulfinyl, methylsulfonyl or ethylsulfonyl, and n is 0, 1, 2, 3 or 4, preferably 0, 1 or 2.

Here, more preference is given to the use of compounds of the formula (I) or salts thereof in which n is 0 (=the number zero, i.e. there are no substituents $R^6$ present, i.e. all free bonds on the ring are occupied by hydrogen) or $(R^6)_n$ is 2-fluoro, 2-chloro, 4-fluoro, 4-chloro, 5-fluoro, 5-chloro, 6-fluoro, 6-chloro, 2-methyl, 2-ethyl, 4-methyl, 4-ethyl, 5-methyl, 5-ethyl, 6-methyl, 6-ethyl, 2-$CF_3$, 2-methoxy, 2-ethoxy, 2-methylsulfonyl, 2-methylsulfinyl, 2-methylthio, 4-$CF_3$, 4-methoxy, 4-ethoxy, 4-methylsulfonyl, 4-methylsulfinyl, 4-methylthio, 5-$CF_3$, 5-methoxy, 5-ethoxy or 5-methylsulfonyl, 5-methylthio, 6-$CF_3$, 6-methoxy, 6-ethoxy or 6-methylsulfonyl, 6-methylthio, 2,6-dimethyl, 2,4-dimethyl, 2,5-dimethyl, 4,5-dimethyl, 4,6-dimethyl, 5,6-dimethyl, 2,6-dichloro, 2,4-dichloro, 2,5-dichloro, 4,5-dichloro, 4,6-dichloro or 5,6-dichloro, where the numbering of the radicals refers to the position of the radical on the 3-pyridyl radical (nitrogen atom=position 1).

Here, particular preference is given to the use of compounds of the formula (I) or salts thereof in which n=0 or in which $(R^6)_n$ is 4-fluoro, 4-chloro, 4-methyl, 4-$CF_3$, 4-methoxy, 4-methylsulfonyl, 4-methylsulfinyl or 4-methylthio, preferably 4-methyl.

Preference is also given to the use of compounds of the formula (I) or salts thereof in which the radicals $R^1$, $R^2$, $R^3$, $R^4$, $R^5$, $R^6$ and n have been selected according to two or more of the meanings mentioned as being preferred.

Particular preference is given to the compounds of the general formula (I) or salts thereof in which $R^1$ is hydrogen and $R^2$, $R^3$, $R^4$, $R^5$, $R^6$ and n are as defined in formula (I) [=compounds of the formula (I'')] or $R^1$ is methyl and $R^2$, $R^3$, $R^4$, $R^5$, $R^6$ and n are as defined in formula (I) [=compounds of the formula (I''')] or $R^2$ and $R^3$ are each hydrogen and $R^1$, $R^4$, $R^5$, $R^6$ and n are as defined in formula (I) [=compounds of the formula (I'''')].

Here, particular preference is given to the compounds of the formula (I) and salts thereof in which one or more of the radicals $R^1$ to $R^6$ have the radical meanings used in the example tables.

The compounds of the formula (I) according to the invention include all stereoisomers which can occur on the basis of the centers of asymmetry or double bonds in the molecule whose configuration is not designated specifically in the formula or which are not specified explicitly, and mixtures thereof, including the racemic compounds and the mixtures enriched partly with particular stereoisomers.

The invention also includes all tautomers, such as keto and enol tautomers, and their mixtures and salts, if appropriate functional groups are present.

Some compounds of the formula (I) are already known. Thus, DE-A-2141124 (U.S. Pat. No. 4,325,962, U.S. Pat. No. 4,146,721) describes heteroaromatically substituted pyrazoles and their use as antiphlogistics, analgetics and antipyretics. Specifically described therein is the preparation of:

a) 3,5-diphenyl-1-(3-pyridyl)pyrazole-4-acetic acid (see DE-A-2141124, Example 1, see U.S. Pat. No. 4,146,721, Example 52), which is the compound of the formula (I) where $R^1$=H, $R^2$=H, $R^3$=H, $R^4$=phenyl, $R^5$=phenyl and n=0, b) ethyl 3,5-diphenyl-1-(3-pyridyl)pyrazole-4-acetate [see DE-A-2141124, Example 1, see U.S. Pat. No. 4,146,721, Example 52, assumed to be an intermediate in the preparation of the compound from paragraph a)], which is the compound of the formula (I) where $R^1$=ethyl, $R^2$=H, $R^3$=H, $R^4$=phenyl, $R^5$=phenyl and n=0, c) 3-methyl-5-phenyl-1-(3-pyridyl)pyrazole-4-acetic acid [see DE-A-2141124, Example 3, U.S. Pat. No. 4,146,721, Example 47(c)], which is the compound of the formula (I) where $R^1$=H, $R^2$=H, $R^3$=H, $R^4$=methyl, $R^5$=phenyl and n=0, d) ethyl 3-methyl-5-phenyl-1-(3-pyridyl)pyrazole-4-acetate (see DE-A-2141124, Example 3, U.S. Pat. No. 4,146,721, Example 47(c)), which is the compound of the formula (I) where $R^1$=ethyl, $R^2$=H, $R^3$=H, $R^4$=methyl, $R^5$=phenyl and n=0.

However, the use according to the invention of these compounds as herbicides and plant growth regulators has hitherto not been known.

U.S. Pat. No. 4,095,025 describes 1,3-diarylpyrazole-4-acrylic acid (derivatives) for pharmaceutical (for example antiinflammatory) purposes. The table for Example 7 (see column 13, "Product") also mentions the compound 3-phenyl-1-(pyrid-3-yl)-pyrazol-4-ylacetic acid. This compound differs from the compounds according to the application in that an aryl or heteroaryl radical in the 5-position of the pyrazole ring is missing. A herbicidal action for the compound is not described.

WO 2004/089931 describes substituted pyrazoles having optionally substituted phenyl or pyrid-3-yl radicals on the nitrogen atom in position 1 of the pyrazole, for the treatment and prophylaxis of diseases moderated by binding of the compounds to 5 HT receptors.

Accordingly, the invention also provides novel compounds of the formula (I) and salts thereof as defined above or as preferably defined above for the use according to the invention, except for the compounds 3,5-diphenyl-1-(3-pyridyl)pyrazole-4-acetic acid, ethyl 3,5-diphenyl-1-(3-pyridyl)pyrazole-4-acetate, 3-methyl-5-phenyl-1-(3-pyridyl)pyrazole-4-acetic acid, ethyl 3-methyl-5-phenyl-1-(3-pyridyl)pyrazole-4-acetate and salts of the compounds mentioned.

The invention also provides processes for preparing the novel compounds of the formula (I) and salts thereof, which comprise (a) reacting a compound of the formula (II)

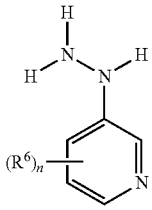

(II)

in which $(R^6)_n$ is as defined in formula (I)
with a compound of the formula (III)

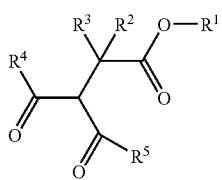

(III)

in which $R^1$, $R^2$, $R^3$, $R^4$ and $R^5$ are as defined in formula (I)
to give the compound of the formula (I) or its salt or (b) in the case that $R^1$ in formula (I) is different from hydrogen, reacting a compound of the formula (I')

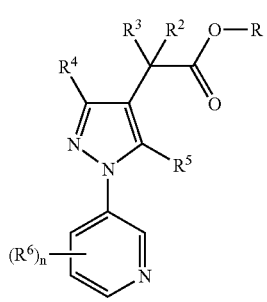

(I')

in which $R^1$, $R^2$, $R^3$, $R^4$ and $R^5$ are as defined in formula (I) and

R is a radical different from the radical $R^1$ and different from hydrogen selected from the group of radicals as defined for $R^1$, or an anhydride, acid halide or an activated ester of the compound of the formula (I') in which R=H, with a compound of the formula (IV)

$R^1$—OH (IV)

in which $R^1$ is as defined in formula (I)
to give the compound of the formula (I) or (c) in the case that $R^1$ in formula (I) is different from hydrogen, esterifying a compound of the formula (I")

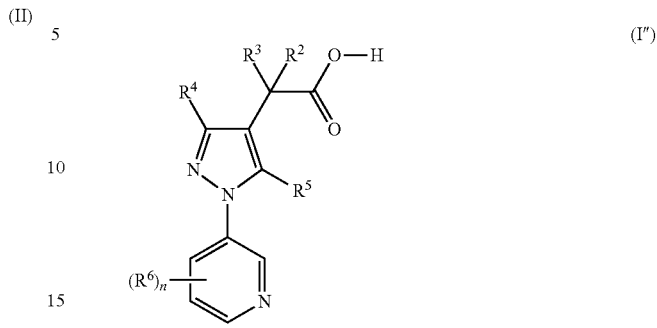

(I")

in which $R^2$, $R^3$, $R^4$ and $R^5$ are as defined in formula (I),
if appropriate after activation of the acid group, with a compound of the formula (IV)

$R^1$—OH (IV)

in which $R^1$ is as defined in formula (I)
to give the compound of the formula (I) or (d) in the case that the compound of the formula (I) in which R═H or its salt is prepared, hydrolyzing a compound of the formula (I') [see definition in variant (b)] to give the compound of the formula (I) or its salt.

In general, the starting materials of the formulae (II), (III) and (IV) are known or can be prepared analogously to known processes.

The compounds of the formula (III) can be prepared, for example, by reacting a dicarbonyl compound of the formula (V)

$R^4$—CO—CH$_2$—CO—$R^5$ (V)

with a compound of the formula (VI)

$R^2R^3$C(Hal)-CO—OR$^1$ (VI)

where $R^1$, $R^2$, $R^3$, $R^4$ and $R^5$ are as defined in formula (III) and $R^1$ is preferably methyl or ethyl and Hal is a leaving group, preferably a reactive halogen, such as a chlorine atom or, in particular, a bromine atom.

In an analogous manner, the processes are already known. Thus, compounds of the formula (I) according to the invention can be prepared analogously to known methods, as described, for example, in *Methoden der organischen Chemie* [Methods of Organic Chemistry] (Houben-Weyl, E. Schaumann, Ed.) volume E8b, Hetarenes III, part 2, pp. 399-710, Georg Thieme Verlag, Stuttgart 1994 and the literature cited therein, where the syntheses according to *Methoden der organischen Chemie* (Houben-Weyl, E. Schaumann, Ed.) volume E8b, Hetarenes III, part 2, p. 420 ff., Georg Thieme Verlag, Stuttgart 1994 and the literature cited therein; *Synthesis*, 1986, 409; *J. Chinese Chem. Soc.*, 2001, 48, 45 and in particular U.S. Pat. No. 4,146,721, DE2141124, DOS1946370 and *Justus Liebigs Ann. Chem.* 1973, 1919 are of particular interest.

The substituted 1,3-dicarbonyl compounds of the formula (III), used as starting materials in process (a) according to the invention for preparing compounds of the formula (I), are preferably those in which the radicals $R^1$, $R^2$, $R^3$, $R^4$ and $R^5$ have the preferred meanings which have already been mentioned above in connection with the description of the compounds of the formula (I) according to the invention as being preferred. Accordingly, the substituted 3-pyridylhydrazines of the formula (II) used as starting materials in the process (a) according to the invention for preparing compounds of the formula (I) also preferably have those meanings of $(R^6)_n$ which have already been given above in connection with the description of the compounds of the formula (I) according to the invention as being preferred for $(R^6)_n$.

The starting materials of the general formula (III) can be obtained by generally known processes by alkylation of appropriate 1,3-diketones with 2-halogenated acetic acid derivatives, for example bromoacetic acid derivatives (c.f., for example, DE-A 1946370, p. 13). The 1,3-diketones (V) used as starting materials for this purpose are commercially available or known and/or can be prepared by known methods (see, for example, U.S. Pat. No. 4,146,721, DE2141124, DOS1946370 or *J. Am. Chem. Soc.,* 1948, 70, 4023; Justus Liebigs Ann. Chem. 1973, 1919; *Justus Liebigs Ann. Chem.* 1976, 13; *J. Chem. Soc. Perkin Trans.* 2, 1993, 6, 1067; *Heteroatom Chemistry,* 1997, 8, 147).

Hydrazines of the formula (II) or salts thereof as starting materials are known and/or can be prepared by known processes (cf., for example, *Methoden der organischen Chemie* (Houben-Weyl, D. Klamann, Ed.) volume E16a, part 1, p. 421 ff., Georg Thieme Verlag, Stuttgart 1990 and the literature cited therein; *J. Am. Chem. Soc.,* 1954, 76, 596; Monatshefte für Chemie 1988, 119, 333; *J. Heterocyclic Chem.* 1988, 25, 1055; *J. Heterocyclic Chem.* 1989, 26, 475; *Heterocycles* 1994, 37, 379).

The reaction of the compounds of the formulae (II) and (III) can be carried out without catalyst or in the presence of catalysts, for example of an acid as catalyst, preferably in an organic solvent, such as tetrahydrofuran (THF), dioxane, acetonitrile, dimethylformamide (DMF), methanol and ethanol, at temperatures between 20° C. and the boiling point of the solvent, preferably at from 50° C. to 150° C. If acid addition salts of the formula (II) are used, these are generally liberated in situ with the aid of a base. Suitable bases or basic catalysts are alkali metal hydroxides, alkali metal hydrides, alkali metal carbonates, alkali metal bicarbonates, alkali metal alkoxides, alkaline earth metal hydroxides, alkaline earth metal hydrides, alkaline earth metal carbonates or organic bases, such as triethylamine, diisopropylethylamine or 1,8-diazabicyclo[5.4.0]undec-7-ene (DBU).

The reaction of the compounds of the formulae (I') and (IV) can be carried out by standard methods of transesterification or esterification via activated carboxylic acids.

The reaction of the compounds of the formulae (I") and (IV) can be carried out by standard methods of esterification or, if appropriate, via activated carboxylic acids. The preparation of compounds of the formula (I") from compounds (I') can be carried out by standard methods of hydrolysis.

Also possible for preparing enantiomers of the compounds (I) are customary methods for optical resolution (cf. textbooks of stereochemistry), for example following processes for separating mixtures into diastereomers, for example physical processes, such as crystallization, chromatographic processes, in particular column chromatography and high-pressure liquid chromatography, distillation, if appropriate under reduced pressure, extraction and other processes, it is possible to separate remaining mixtures of enantiomers, generally by chromatographic separation on chiral solid phases. Suitable for preparative amounts or on an industrial scale are processes such as the crystallization of diastereomeric salts which can be obtained from the compounds (I) using optically active acids and, if appropriate, provided that acidic groups are present, using optically active bases.

Optically active acids which are suitable for optical resolution by crystallization of diastereomeric salts are, for example, camphorsulfonic acid, camphoric acid, bromocamphorsulfonic acid, quinic acid, tartaric acid, dibenzoyltartaric acid and other analogous acids; suitable optically active bases are, for example, quinine, cinchonine, quinidine, brucine, 1-phenylethylamine and other analogous bases. The crystallizations are then in most cases carried out in aqueous or aqueous-organic solvents, where the diastereomer which is less soluble precipitates first, if appropriate after seeding. One enantiomer of the compound of the formula (I) is then liberated from the precipitated salt, or the other is liberated from the crystals, by acidification or using a base.

The following acids are suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulfonic acids, such as p-toluenesulfonic acid and 1,5-naphthalenedisulfonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide of the formula $[NRR'R''R''']^+ OH^-$.

What is meant by the "inert solvents" referred to in the above process variants are in each case solvents which are inert under the particular reaction conditions but need not be inert under all reaction conditions.

A collection of compounds of the formula (I) which can be synthesized by the abovementioned processes can additionally be prepared in a parallelized manner, in which case this can be done in a manual, partly automated or completely automated manner. It is possible to automate the reaction procedure, the workup or the purification of the products or intermediates. Overall, this is understood to mean a procedure as described, for example, by S. H. DeWitt in "Annual Reports in Combinatorial Chemistry and Molecular Diversity: Automated Synthesis", Volume 1, Verlag Escom, 1997, pages 69 to 77.

For parallelized reaction procedure and workup, a number of commercially available units can be used, as supplied, for example, by Stem Corporation, Woodrolfe Road, Tollesbury, Essex, CM98SE, England or H+P Labortechnik GmbH, Bruckmannring 28, 85764 Oberschleißheim, Germany. For the parallelized purification of compounds (I) or of intermediates which occur in the preparation, available apparatus includes chromatography apparatus, for example from ISCO, Inc., 4700 Superior Street, Lincoln, Nebr. 68504, USA. The apparatus listed enables a modular procedure in which the individual working steps are automated but manual operations have to be performed between the working steps. This can be circumvented by the use of partly or completely integrated automation systems in which the individual automation modules are operated, for example, by robots. Such automation systems can be purchased, for example, from Zymark Corporation, Zymark Center, Hopkinton, Mass. 01748, USA.

In addition to the methods described, compounds of the formula (I) can be prepared completely or partially by solid phase-supported methods. For this purpose, individual intermediates or all intermediates of the synthesis or of a synthesis adjusted for the appropriate procedure are bound to a synthetic resin. Solid phase-supported synthesis methods are described adequately in the technical literature, for example: Barry A. Bunin in "The Combinatorial Index", Verlag Academic Press, 1998.

The use of solid phase-supported synthesis methods enables a number of literature procedures, which can again be performed in a manual or automated manner. For example the "teabag method" (Houghten, U.S. Pat. No. 4,631,211; Houghten et al., Proc. Natl. Acad. Sci., 1985, 82, 5131-5135) with products from IRORI, 11149 North Torrey Pines Road, La Jolla, Calif. 92037, USA, can be partly automated. The automation of solid phase-supported parallel synthesis is possible, for example, by means of apparatus from Argonaut Technologies, Inc., 887 Industrial Road, San Carlos, Calif. 94070, USA or MultiSynTech GmbH, Wullener Feld 4, 58454 Witten, Germany.

The preparation by the processes described here affords compounds of the formula (I) in the form of substance collections or libraries. The present invention therefore also provides libraries of the compounds of the formula (I) which comprise at least two compounds of the formula (I) and precursors thereof.

The inventive compounds of the formula (I) and salts thereof have excellent herbicidal activity against a wide spectrum of economically important monocotyledonous and dicotyledonous harmful plants. The active ingredients also act efficiently on perennial weeds which are difficult to control and give out shoots from rhizomes, root stocks or other perennial organs. It is unimportant whether the substances are applied before sowing, pre-emergence or post-emergence.

A few representatives of the mono- and dicotyledonous weed flora which can be controlled by the inventive compounds will be specified individually by way of example, without any intention that the specification should bring about a restriction to particular species.

Among the monocotyledonous weed species, those on which the active substances act efficiently are, for example, *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea* and *Cyperus* species from the annual group, and, among the perennial species, *Agropyron, Cynodon, Imperata* and *Sorghum*, and also perennial *Cyperus* species.

In the case of dicotyledonous weed species, the activity spectrum extends to species such as, for example, *Galium, Viola, Veronica, Lamium, Stellaria, Amaranthus, Sinapis, Ipomoea, Matricaria, Abutilon* and *Sida* on the annual side, and also *Convolvulus, Cirsium, Rumex* and *Artemisia* among the perennial weeds. Herbicidal action is also achieved in the case of dicotyledonous harmful plants such as *Ambrosia, Anthemis, Carduus, Centaurea, Chenopodium, Cirsium, Convolvulus, Datura, Emex, Galeopsis, Galinsoga, Kochia, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

Weeds which occur in rice under the specific crop conditions, for example *Sagittaria, Alisma, Eleocharis, Scirpus* and *Cyperus*, are likewise controlled outstandingly by the inventive active ingredients.

When the inventive compounds are applied to the soil surface before germination, the weed seedlings are either prevented completely from emerging or the weeds grow up to the cotyledon stage but then stop growing and finally die off completely after three to four weeks have passed.

When the active substances are applied to the green plant parts post-emergence, a drastic stop in growth likewise occurs very rapidly after the treatment, and the weed plants remain at the stage of growth at the time of application or die off completely after a certain time, so that weed competition which is harmful to the crop plants is thus eliminated at a very early stage and in a lasting manner.

Even though the inventive compounds have excellent herbicidal activity against mono- and dicotyledonous weeds, crop plants of economically significant crops, for example wheat, barley, rye, rice, maize, sugarbeet, soya, in particular plantation crops such as oil palms, olives, coconut, rubber tree, citrus, pineapple, apple, pear, cherry, cotton, coffee, cocoa, grapes and other comparable fruit and plantation crops, are damaged only insignificantly, if at all. For these reasons, the present compounds are very suitable for the selective control of undesired plant growth in stands of agriculturally useful plants, including ornamental stands. The active ingredients are also suitable, optionally in combination with other active ingredients, for use in uncultivated land, such as on paths, open spaces, beds, lawns, railway embankments, industrial areas, for controlling unwanted plant growth.

In addition, the inventive substances have outstanding growth-regulatory properties in crop plants. They intervene to regulate the plants' metabolism and can thus be used for controlled influence on plant constituents and for easing the harvest, for example by inducing desiccation and stunted growth. Moreover, they are also suitable for the general control and inhibition of undesired vegetative growth without killing the plants. Inhibition of vegetative growth plays a major role in many mono- and dicotyledonous crops, since this allows lodging to be reduced or completely prevented.

Owing to their herbicidal and plant growth-regulatory properties, the active ingredients can also be used to control harmful plants or regulate growth in crops of known genetically modified plants or genetically modified plants which are yet to be developed. The transgenic plants generally feature particular advantageous properties, for example resistances against particular pesticides, especially particular herbicides, resistances toward plant diseases or pathogens of plant diseases, such as particular insects or microorganisms, such as fungi, bacteria or viruses. Other exceptional properties relate, for example, to the harvest with regard to amount, quality, storability, composition and specific constituents. Thus, transgenic plants with increased starch content or altered starch quality or those with different fatty acid composition of the harvest are known.

Preference is given to the use of the inventive compounds of the formula (I) or salts thereof in economically significant transgenic crops of useful and ornamental plants, for example of cereals such as wheat, barley, rye, oats, millet, rice, manioc and maize, or else crops of sugarbeet, cotton, soya, rape, potato, tomato, pea and other vegetable types.

The compounds of the formula (I) can preferably be used as herbicides in useful plant crops which are resistant toward the phytotoxic effects of the herbicides or have been made resistant by genetic engineering.

Conventional routes to the production of novel plants which have modified properties in comparison to existing plants consist, for example, in traditional breeding methods and the generation of mutants. Alternatively, novel plants with altered properties can be obtained with the aid of recombinant methods (see, for example, EP-A-0221044, EP-A-0131624). For example, several cases of the following have been described:

recombinant modifications of crop plants for the purpose of modification of the starch synthesized in the plants (for example WO 92/11376, WO 92/14827, WO 91/19806), transgenic crop plants which are resistant toward particular herbicides of the glufosinate type (cf., for example, EP-A-0242236, EP-A-242246) or glyphosate type (WO 92/00377) or sulfonylurea type (EP-A-0257993, U.S. Pat. No. 5,013,659), transgenic crop plants, for example cotton, with the ability to produce *Bacillus thuringiensis* toxins (Bt toxins) which make the plants resistant to particular pests (EP-A-0142924, EP-A-0193259), transgenic crop plants with modified fatty acid composition (WO 91/13972).

Numerous molecular biology techniques with which novel transgenic plants with altered properties can be produced are known in principle; see, for example, Sambrook et al., 1989, Molecular Cloning, A Laboratory Manual, 2nd Ed. Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423-431.

For such recombinant manipulations, nucleic acid molecules can be incorporated into plasmids which allow mutagenesis or a change in sequence through recombination of DNA sequences. With the aid of the abovementioned standard methods, it is possible, for example, to undertake base exchanges, remove part-sequences or add natural or synthetic sequences. For the bonding of the DNA fragments to one another, it is possible to attach adapters or linkers to the fragments.

The production of plant cells with a reduced activity of a gene product can be achieved, for example, by the expression of at least one appropriate antisense RNA, a sense RNA for achieving a cosuppression effect or the expression of at least one correspondingly constructed ribozyme which specifically cleaves transcripts of the abovementioned gene product. To this end, it is possible firstly to use DNA molecules which include the entire coding sequence of a gene product including any flanking sequences present, or DNA molecules which include only parts of the coding sequence, in which case these parts have to be long enough to bring about an antisense effect in the cells. It is also possible to use DNA sequences which have a high degree of homology to the coding sequences of a gene product but are not completely identical.

In the expression of nucleic acid molecules in plants, the synthesized protein can be localized in any compartment of the plant cell. In order, though, to achieve localization in a particular compartment, it is possible, for example, to link the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants may be plants of any desired plant species, i.e. either monocotyledonous or dicotyledonous plants.

It is thus possible to obtain transgenic plants which have altered properties through overexpression, suppression or inhibition of homologous (=natural) genes or gene sequences or expression of heterologous (=foreign) genes or gene sequences.

The inventive compounds (I) may preferably be used in transgenic cultures which are resistant toward herbicides from the group of the imidazolinones, sulfonylureas, glufosinate-ammonium or glyphosate-isopropylammonium and analogous active ingredients.

When the inventive active ingredients are used in transgenic cultures, in addition to the effects on harmful plants observed in other crops, effects specific to the application in the particular transgenic culture often occur, for example an altered or specifically extended weed spectrum which can be controlled, altered application rates which can be used for the application, preferably good combinability with the herbicides toward which the transgenic culture is resistant, and influencing of growth and yield of the transgenic crop plants.

The invention therefore also provides for the use of the inventive compounds (I) as herbicides for controlling harmful plants or for regulating the growth of plants in transgenic crop plants.

The inventive use for the control of harmful plants or for growth regulation of plants also includes the case in which the active ingredient of the formula (I) or its salt is not formed from a precursor substance ("prodrug") until after application on the plant, in the plant or in the soil.

The inventive compounds can be used in the form of wettable powders, emulsifiable concentrates, sprayable solutions, dusting products or granules in the customary formulations. The invention therefore also provides herbicidal and plant growth-regulating compositions which comprise compounds of the formula (I).

The compounds of the formula (I) can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflätchenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Wettable powders are preparations which can be dispersed uniformly in water and, as well as the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the active herbicidal ingredients are ground finely, for example in customary apparatus such as hammer mills, blower mills and air-jet mills and simultaneously or subsequently mixed with the formulation assistants.

Emulsifiable concentrates are prepared by dissolving the active ingredient in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active ingredient onto adsorptive granulated inert material or by applying active ingredient concentrates by means of adhesives, for example polyvinyl alcohol, sodium polyacrylate or else mineral oils, onto the surface of carriers such as sand, kaolinites or of granulated inert material. It is also possible to granulate suitable active ingredients in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of active ingredient of the formula (I). In wettable powders, the active ingredient concentration is, for example, from about 10 to 90% by weight; the remainder to 100% by weight consists of customary formulation constituents. In the case of emulsifiable concentrates, the active ingredient concentration may be from about 1 to 90% by weight, preferably from 5 to 80% by weight. Dust-type formulations contain from 1 to 30% by weight of active ingredient, preferably usually from 5 to 20% by weight of active ingredient; sprayable solutions contain from about 0.05 to 80% by weight, preferably from 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described inter alia in "Chemistry and Technology of Agrochemical Formulations", ed. D. A. Knowles, Kluwer Academic Publishers (1998).

The compounds of the formula (I) or salts thereof may be used as such or in the form of their formulations combined with other pesticidally active substances, for example insecticides, acaricides, nematicides, herbicides, fungicides, safeners, fertilizers and/or growth regulators, for example as a finished formulation or as tankmixes. The combination formulations can be prepared on the basis of the above-mentioned formulations, while taking account of the physical properties and stabilities of the active ingredients to be combined.

Possible combination partners for the inventive active ingredients, in mixed formulations or in a tankmix, are, for example, known active ingredients which are based on inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other usable compounds, with a mechanism of action that is, in some cases, unknown or different, are described, for example, in Weed Research 26, 441-445 (1986), or "The Pesticide Manual", 14th edition 2006/2007, published by the British Crop Protection Council (hereinafter also abbreviated to "PM"), and literature cited there. Herbicides, plant growth regulators and herbicide safeners, which are known from the literature and which can be combined with the compounds of the formula (I), include, for example, the following active ingredients (note: the compounds are either referred to by the common name in accordance with the International Organization for Standardization (ISO) or by the chemical name, if appropriate together with a customary code number): acetochlor; acibenzolar-5-methyl; acifluorfen(-sodium); aclonifen; AD-67; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; aminopyralid; amitrole; AMS, i.e. ammonium sulfamate; ancymidol; anilofos; asulam; atrazine; aviglycine, azafenidin, azimsulfuron (DPX-A8947); aziprotryn; barban; BAS 516H, i.e. 5-fluoro-2-phenyl-4H-3,1-benzoxazin-4-one; beflubutamid, benazolin(-ethyl); bencarbzone; benfluralin; benfuresate; benoxacor; bensulfuron(-methyl); bensulide; bentazone; benzfendizone, benzobicyclon, benzofenap; benzofluor; benzoylprop(-ethyl); benzthiazuron; bialaphos; bifenox; bilanafos (bialaphos), bispyribac(-sodium), borax, bromacil; bromobutide; bromofenoxim; bromoxynil; bromuron; buminafos; busoxinone; butachlor; butafenacil, butamifos; butenachlor; buthidazole; butralin; butroxydim, butylate; cafenstrole (CH-900); carbetamide; carfentrazone(-ethyl) (ICI-A0051); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlorflurenol(-methyl), chlormequat (-chloride), chlormesulon (ICI-A0051); chlorbromuron; chlorbufam; chlorfenac; chloridazon; chlorimuron(-ethyl); chlornitrofen; chlorotoluron; chloroxuron; chlorpropham; chlorsulfuron; chlorthaldimethyl; chlorthiamid; chlortoluron, cinidon(-methyl and -ethyl), cinmethylin; cinosulfuron; clefoxydim, clethodim; clodinafop and its ester derivatives (e.g. clodinafop-propargyl); clofencet; clomazone; clomeprop; cloprop, cloproxydim; clopyralid; clopyrasulfuron(-methyl), cloquintocet(-mexyl), cloransulam(-methyl), cumyluron (JC 940); cyanamide, cyanazine; cyclanilide, cycloate; cyclosulfamuron (AC 104); cycloxydim; cycluron; cyhalofop and its ester derivatives (e.g. butyl ester, DEH-112); cyperquat; cyprazine; cyprazole; cyprosulfamide; daimuron; 2,4-D, 2,4-DB; 2,4-DB, dalapon; daminozide, dazomet, n-decanol, desmedipham; desmetryn; di-allate; dicamba; dichlobenil; dichlormid, dichlorprop(-P) (salts); diclofop and its esters such as diclofop-methyl; diclosulam; diethatyl(-ethyl); difenoxuron; difenzoquat(-metilsulfate); diflufenican; diflufenzopyr, dimefuron; dimepiperate, dimethachlor; dimethametryn; dimethazone; dimethenamid (SAN-582H); dimethenamid-P, dimethylarsinic acid, dimexyflam, dimethipin; dimetrasulfuron, dinitramine; dinoseb; dinoterb; diphenamid; dipropetryn; diquat (salts); dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethephon, ethidimuron; ethiozin; ethofumesate; ethoxyfen and its esters (e.g. ethyl ester, HN-252); ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]phenyl]ethanesulfonamide; fenchlorazole(-ethyl), fenclorim; fenoprop; fenoxan, fenoxapropand fenoxaprop-P and their esters, e.g. fenoxaprop-P-ethyl and fenoxaprop-ethyl; fenoxydim; fentrazamide, fenuron; ferrous sulfate, flamprop(-methyl or -isopropyl or -isopropyl-L); flazasulfuron; floazulate, florasulam; fluazifop and fluazifop-P and their esters, e.g. fluazifop-butyl and fluazifop-P-butyl; fluazolate, flucarbazone(-sodium), flucetosulfuron, fluchloralin; flufenacet, flufenpyr(-ethyl), flumetralin, flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupropanoate, flupyrsulfuron(-methyl)(-sodium), flurazole, flurenol(-butyl), fluridone; fluorochloridone; fluoroxypyr(-meptyl); flurprimidol, flurtamone; fluthiacet(-methyl), fluthiamide, fluxofenim, fomesafen; foramsulfuron, forchlorfenuron, fosamine; furilazole, furyloxyfen; gibberillic acid, glufosinate (-ammonium); glyphosate(-isopropylammonium); halosafen; halosulfuron(-methyl) and its esters (e.g. methyl ester, NC-319); haloxyfop and its esters; haloxyfop-P(=R-haloxyfop) and its esters; HC-252, hexazinone; imazamethabenz(-methyl); imazamox, imazapic, imazapyr; imazaquin and salts such as the ammonium salt; imazamethapyr, imazapic, imazethamethapyr; imazethapyr; imazosulfuron; inabenfide, indanofan, indole-3-ylacetic acid, 4-indol-3-ylbutyric acid, iodosulfuron-methyl(-sodium), ioxynil; isocarbamid; isopropalin; isoproturon; isouron; isoxaben; isoxachlortole, isoxadifen(-ethyl), isoxaflutole, isoxapyrifop; karbutilate; lactofen; lenacil; linuron; maleic hydrazide, MCPA; MCPB; mecoprop(-P), mefenacet; mefenpyr(-diethyl), mefluidid; mepiquat(-chloride), mesotrione, mesosulfuron(-methyl), mesotrione, metam, metamifop, metamitron; metazachlor; methabenzthiazuron; methazole; methoxyphenone; methylarsonic acid, 1-methylcyclopropene, methyldymron; methyl isothiocyanate, metobenzuron, metobromuron; (alpha-)metolachlor; metosulam (XRD 511); metoxuron; metribuzin; metsulfuron-methyl; MH; MK-616, molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; 2-(1-naphthyl) acetamide, 1-naphthylacetic acid, 2-naphthyloxyacetic acid, naproanilide; napropamide; naptalam; NC 310, i.e. 4-(2,4-dichlorobenzoyl)-1-methyl-5-benzyloxypyrazole; neburon; nicosulfuron; nipyraclofen; nitralin; nitrofen; nitrophenolate mixture, nitrofluorfen; nonanoic acid, norflurazon; orbencarb; orthasulfamuron, oryzalin; oxabetrinil, oxadiargyl (RP-020630); oxadiazon; oxasulfuron, oxaziclomefone, oxyfluorfen; paclobutrazol, paraquat(-dichloride); pebulate; pelargonic acid, pendimethalin; penoxulam, pentachlorophenol, pentanochlor, pentoxazone, perfluidone; pethoxamid, phenisopham; phenmedipham; picloram; picolinafen, pinoxaden, piperophos; piributicarb; pirifenop-butyl; pretilachlor; primisulfuron(-methyl); probenazole, procarbazone(-sodium), procyazine; prodiamine; profluralin; profoxydim, prohexadione(-calcium), prohydrojasmon, proglinazine(-ethyl); prometon; prometryn; propachlor; propanil; propaquizafop and its esters; propazine; propham; propisochlor; propoxycarbazone(-sodium), n-propyl dihydrojasmonate, propyzamide; prosulfalin; prosulfocarb; prosulfuron (CGA-152005); prynachlor; pyraclonil, pyraflufen(-ethyl), pyrasulfotole, pyrazolynate; pyrazon; pyrazosulfuron(-ethyl); pyrazoxyfen; pyribenzoxim, pyributicarb, pyridafol, pyridate; pyriftalid, pyriminobac(-methyl), pyrimisulfan, pyrithiobac (-sodium) (KIH-2031); pyroxasulfone, pyroxofop and its esters (e.g. propargyl ester); pyroxsulam, quinclorac; quinmerac; quinoclamine, quinofop and its ester derivatives, quizalofop and quizalofop-P and their ester derivatives, e.g. quizalofop-ethyl; quizalofop(P-tefuryl and -ethyl); renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; sintofen, SN 106279, i.e. 2-[[7-[2-chloro-4-(trifluoromethyl)phenoxy]-2-naphthalenyl]oxy]propanoic acid and its methyl ester; sulcotrione, sulfentrazone (FMC-97285, F-6285); sulfazuron; sulfometuron(-methyl); sulfosate (ICI-A0224); sulfosulfuron, 2,3,6-TBA, TCA; tebutam (GCP-5544); tebuthiuron; tecnazene, tefuryltrione, tembotrione, tepraloxydim, terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide, thiazafluoron; thiazopyr (Mon-13200); thidiazimin (SN-24085); thidiazuron, thiencarbazone, thifensulfuron(-methyl);

thiobencarb; TI-35, tiocarbazil; topramezone, tralkoxydim; tri-allate; triasulfuron; triaziflam, triazofenamide; tribenuron (-methyl); triclopyr; tridiphane; trietazine; trifloxysulfuron(-sodium), trifluralin; triflusulfuron and esters (e.g. methyl ester, DPX-66037); trimeturon; trinexapac(-ethyl), tritosulfuron, tsitodef; uniconazole, vernolate; WL 110547, i.e. 5-phenoxy-1-[3-(trifluoromethyl)phenyl]-1H-tetrazole;

BAY MKH 6561, UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

What is of particular interest is the selective control of harmful plants in crops of useful and ornamental plants. Although the inventive compounds (I) have very good to satisfactory selectivity in a large number of crops, it is possible in principle that phytotoxicity in the crop plants can occur in some crops and, in particular, also in the case of mixtures with other herbicides which are less selective. In this respect, combinations of particular interest are those of inventive compounds (I) which contain the compounds (I), or their combinations with other herbicides or pesticides, and safeners. The safeners, which are used in such amounts that they act as antidotes, reduce the phytotoxic side effects of the herbicides/pesticides used, for example in economically important crops such as cereals (wheat, barley, rye, maize, rice, millet), sugarbeet, sugar cane, rape, cotton and soya, preferably cereals. The following groups of compounds are useful, for example, as safeners for the compounds (I) and their combinations with other pesticides:

a) Compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (S1-1) ("mefenpyr-diethyl", PM), and related compounds, as described in WO 91/07874, b) Derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds, as described in EP-A-333 131 and EP-A-269 806.

c) Compounds of the triazolecarboxylic acid type, preferably compounds such as fenchlorazole(ethyl ester), i.e. ethyl 1-(2,4-dichlorophenyl)-5-trichloromethyl-(1H)-1,2,4-triazole-3-carboxylate (S1-6) and related compounds (EP-A-174 562 and EP-A-346 620);

d) Compounds of the 5-benzyl- or 5-phenyl-2-isoxazoline-3-carboxylic acid type, or the 5,5-diphenyl-2-isoxazoline-3-carboxylic acid type, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or the n-propyl ester (S1-10) or ethyl 5-(4-fluorophenyl)-5-phenyl-2-isoxazoline-3-carboxylate (S1-11), as described in German patent application WO-A-95/07897.

e) Compounds of the 8-quinolineoxyacetic acid type (S2), preferably
1-methylhex-1-yl (5-chloro-8-quinolineoxy)acetate (common name "cloquintocet-mexyl" (S2-1) (see PM)
1,3-dimethylbut-1-yl (5-chloro-8-quinolineoxy)acetate (S2-2),
4-allyloxybutyl (5-chloro-8-quinolineoxy)acetate (S2-3),
1-allyloxyprop-2-yl (5-chloro-8-quinolineoxy)acetate (S2-4),
ethyl (5-chloro-8-quinolineoxy)acetate (S2-5),
methyl (5-chloro-8-quinolineoxy)acetate (S2-6),
allyl (5-chloro-8-quinolineoxy)acetate (S2-7),
2-(2-propylideneiminoxy)-1-ethyl (5-chloro-8-quinolineoxy)acetate (S2-8),
2-oxoprop-1-yl (5-chloro-8-quinolineoxy)acetate (S2-9)
and related compounds, as described in EP-A-86 750, EP-A-94 349 and EP-A-191 736 or EP-A-0 492 366.

f) Compounds of the (5-chloro-8-quinolineoxy)malonic acid type, preferably compounds such as diethyl (5-chloro-8-quinolineoxy)malonate, diallyl (5-chloro-8-quinolineoxy) malonate,
methylethyl (5-chloro-8-quinolineoxy)malonate and related compounds, as described in EP-A-0 582 198.

g) Active ingredients of the phenoxyacetic or -propionic acid derivative type or the aromatic carboxylic acid type, for example 2,4-dichlorophenoxyacetic acid/esters (2,4-D), 4-chloro-2-methylphenoxypropionic esters (mecoprop), MCPA or 3,6-dichloro-2-methoxybenzoic acid/esters (dicamba).

h) Active ingredients of the pyrimidine type, which are used as soil-acting safeners in rice, for example
"fenclorim" (PM) (=4,6-dichloro-2-phenylpyrimidin), which is known as safener for pretilachlor in sown rice, i) Active ingredients of the dichloroacetamide type, which are frequently used as pre-emergent safeners (soil-acting safeners), for example
"dichlormid" (PM) (=N,N-diallyl-2,2-dichloroacetamide),
"R-29148" (=3-dichloroacetyl-2,2,5-trimethyl-1,3-oxazolidine from Stauffer),
"benoxacor" (PM) (=4-dichloroacetyl-3,4-dihydro-3-methyl-2H-1,4-benzoxazine),
"PPG-1292" (=N-allyl-N-[(1,3-dioxolan-2-yl)methyl] dichloroacetamide from PPG Industries),
"DK-24" (=N-allyl-N-[(allylaminocarbonyl)methyl] dichloroacetamide from Sagro-Chem),
"AD-67" or "MON 4660" (=3-dichloroacetyl-1-oxa-3-aza-spiro[4,5]decane from Nitrokemia or Monsanto),
"diclonon" or "BAS145138" or "LAB145138" (=(=3-dichloroacetyl-2,5,5-trimethyl-1,3-diazabicyclo[4.3.0] nonane from BASF) and
"furilazol" or "MON 13900" (see PM) (=(RS)-3-dichloroacetyl-5-(2-furyl)-2,2-dimethyloxazolidine)

j) Active ingredients of the dichloroacetone derivative type, for example "MG 191" (CAS-Reg. No. 96420-72-3) (=2-dichloromethyl-2-methyl-1,3-dioxolane from Nitrokemia), which is known as safener for maize, k) Active ingredients of the oxyimino compound type, which are known as seed dressings, for example
"oxabetrinil" (PM) (=(Z)-1,3-dioxolan-2-ylmethoxyimino (phenyl)acetonitrile), which is known as a seed dressing safener for millet against metolachlor damage,
"fluxofenim" (PM) (=1-(4-chlorophenyl)-2,2,2-trifluoro-1-ethanone-O-(1,3-dioxolan-2-ylmethyl) oxime), which is known as a seed dressing safener for millet against metolachlor damage, and
"cyometrinil" or "-CGA-43089" (PM) (=(Z)-cyanomethoxy-imino(phenyl)acetonitrile), which is known as a seed dressing safener for millet against metolachlor damage, l) Active ingredients of the thiazolecarboxylic ester type, which are known as seed dressings, for example "flurazol" (PM) (=benzyl 2-chloro-4-trifluoromethyl-1,3-thiazole-5-carboxylate), which is known as a seed dressing safener for millet against alachlor and metolachlor damage, m) Active ingredients of the naphthalenedicarboxylic acid derivative type, which are known as seed dressings, for example "naphthalic anhydride" (PM) (=1,8-naphthalenedicarboxylic anhydride), which is known as a seed dressing safener for maize against thiocarbamate herbicide damage, n) Active ingredients of the chromanacetic acid derivative type, for example "CL 304415" (CAS-Reg. No. 31541-57-8) (=2-(4-carboxychroman-4-yl)acetic acid from American Cyanamid), which is known as safener for maize against imidazolinone damage, o) Active ingredients which, in addition to a herbicidal action against harmful plants, also have safener action in crop plants such as rice, for example "dimepiperate" or "MY-93" (PM) (=S-1-methyl-1-phenylethyl piperidine-1-thiocarboxylate), which is known as safener for rice against herbicide molinate damage, "daimuron" or "SK 23" (PM) (=1-(1-methyl-1-phenylethyl)-3-p-tolylurea), which is known as safener for rice against herbicide imazosulfuron damage, "cumyluron"="JC-940" (=3-(2-chlorophenylmethyl)-1-(1-methyl-1-phenylethyl)urea, see JP-A-60087254), which is known as safener for rice against damage by some herbicides, "methoxyphenon" or "NK 049" (=3,3'-dimethyl-4-methoxy-benzophenone), which is known as safener for rice against damage by some herbicides, "CSB" (=1-bromo-4-(chloromethylsulfonyl)benzene) (CAS-Reg. No. 54091-06-4 from Kumiai), which is known as safener against damage by some herbicides in rice, p) N-Acylsulfonamides of the formula (S3) and salts thereof,

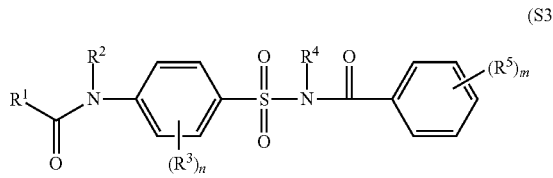

as described in WO-A-97/45016, q) Acylsulfamoylbenzoamides of the formula (S4), if appropriate also in salt form,

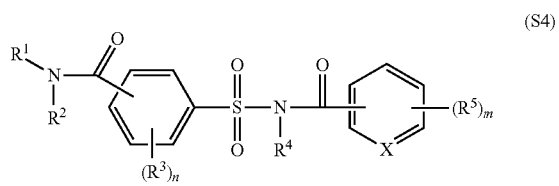

as described in the International Application No. PCT/EP98/06097, for example "cyprosulfamides" (S4-1) and r) compounds of the formula (S5),

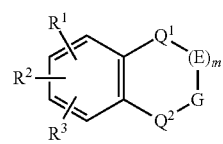

as described in WO-A 98/13 361,
including the stereoisomers and the salts normally used in agriculture.

Among the safeners mentioned, (S1-1), (S1-9), (S2-1) and (S4-1), are of particular interest.

Some of the safeners are already known as herbicides and consequently also display, in addition to the herbicidal action against harmful plants, protective action in connection with crop plants.

The ratios by weight of herbicide (mixture) to safener generally depend on the application rate of the herbicide and the efficacy of the safener in question and can vary within wide limits, for example in the range from 200:1 to 1:200, preferably from 100:1 to 1:100, in particular from 20:1 to 1:20. Analogously to the compounds (I) or their mixtures, the safeners can be formulated with other herbicides/pesticides and be provided and used as a finished formulation or tankmix with the herbicides.

For use, the herbicide or herbicide/safener formulations which are present in commercially available form are, if appropriate, diluted in the customary manner, for example using water in the case of wettable powders, emulsifiable concentrates, dispersions and water-dispersible granules. Preparations in the form of dusts, granules for soil application or broadcasting and sprayable solutions are usually not diluted further with other inert substances prior to use.

The required application rate of the compounds of the formula (I) varies with the external conditions, such as temperature, humidity, the nature of the herbicide used and the like. It can vary within wide limits. For the application of herbicide for controlling harmful plants, it is, for example, in the range of from 0.001 to 10.0 kg/ha or more of active substance, preferably in the range of from 0.005 to 5 kg/ha, in particular in the range of from 0.01 to 1 kg/ha, of active substance. This applies both to the pre-emergence and the post-emergence application.

When used as plant growth regulator, for example as culm stabilizer for crop plants like those mentioned above, preferably cereal plants, such as wheat, barley, rye, triticale, millet, rice or corn, the application rate is, for example, in the range of from 0.001 to 2 kg/ha or more of active substance, preferably in the range of from 0.005 to 1 kg/ha, in particular in the range of from 10 to 500 g/ha of active substance, very particularly from 20 to 250 g/ha of active substance. This applies both to application by the pre-emergence method and the post-emergence method, the post-emergence treatment generally being preferred.

The application as culm stabilizer may take place at various stages of the growth of the plants. Preferred is, for example, an application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

In an exemplary manner, some synthesis examples of compounds of the general formula (I) are described below.

In the examples, the amounts (including percentages) refer to the weight, unless especially stated otherwise. If, in the context of the description and the examples, the terms "R" and "S" are given for the absolute configuration on a center of chirality of the stereoisomers of the formula (I), this RS nomenclature, follows, unless defined differently, the Cahn-Ingold-Prelog rule.

(A) SYNTHESIS EXAMPLES

Example A1

Methyl [5-(3-chlorophenyl)-3-methyl-1-pyridin-3-yl-1H-pyrazol-4-yl]acetate (see Table 2, Example 2-17)

0.577 g (4.233 mmol) of 3-hydrazinopyridine in 5.00 ml of ethanol was added to 0.650 g (2.419 mmol) of methyl 3-(3-chlorobenzoyl)-4-oxopentanoate, and the mixture was stirred in a closed vessel in a microwave oven at 130° C. for 1.5 h. The solvent was removed under reduced pressure, and the residue was taken up in dichloromethane and washed twice with in each case 25 ml of water. The combined organic phases were dried over sodium sulfate, and the solvent was removed under reduced pressure. Chromatography of the residue gave 0.364 g (42% of theory) of a light-yellow oil. $^1$H-NMR (CDCl$_3$): see Table 2.

Example A2

[5-(3-Chlorophenyl)-3-methyl-1-pyridin-3-yl-1H-pyrazol-4-yl]acetic acid (see Table 1, Example 1-17)

0.053 g (1.334 mmol) of 2 molar aqueous sodium hydroxide solution was added to 0.114 g (0.334 mmol) of methyl [5-(3-chlorophenyl)-3-methyl-1-pyridin-3-yl-1H-pyrazol-4-yl]acetate (see A1), and the mixture was stirred at 20° C. for 1 h. The methanol formed during the reaction was removed under reduced pressure, and the residue was poured onto a mixture of 10 ml of water and 15 ml of dichloromethane. The aqueous phase was extracted with 15 ml of dichloromethane, acidified with concentrated hydrochloric acid (pH=3) and extracted three times with in each case 15 ml of dichloromethane. Drying of the combined organic phases and removal of the solvent under reduced pressure give 0.050 g (43% of theory) of a light-beige solid of melting point 163° C.

Example A3

Methyl [3-methyl-1-(4-methylpyridin-3-yl)-5-phenyl-1H-pyrazol-4-yl]acetate (see Table 2, Example 2-10)

0.315 g (2.049 mmol) of 3-hydrazino-4-methylpyridine in 5.00 ml of ethanol was added to 0.400 g (1.708 mmol) of methyl 3-benzoyl-4-oxopentanoate, and the mixture was stirred under reflux for 8 h. The solvent was removed under reduced pressure giving, after chromatography of the residue, 0.305 g (47% of theory) of a reddish wax-like solid. $^1$H-NMR (CDCl$_3$): see Table 2.

Example A4

[3-Methyl-1-(4-methylpyridin-3-yl)-5-phenyl-1H-pyrazol-4-yl]acetic acid (see Table 1, Example 1-10)

0.100 g (2.489 mmol) of 2 molar aqueous sodium hydroxide solution was added to 0.200 g (0.498 mmol) of methyl [3-methyl-1-(4-methylpyridin-3-yl)-5-phenyl-1H-pyrazol-4-yl]acetate in 5.00 ml of methanol, and the mixture was stirred at 20° C. for 1 h. The methanol was removed under reduced pressure, and the residue was poured onto a mixture of 10 ml of water and 15 ml of dichloromethane. The aqueous phase was extracted with 15 ml of dichloromethane, acidified with concentrated hydrochloric acid (pH=3) and extracted three times with in each case 15 ml of dichloromethane. Drying of the combined organic phases and removal of the solvent under reduced pressure give 0.108 g (71% of theory) of a yellow solid of melting point 246° C.

Example A5

Prop-2-yn-1-yl [3-methyl-1-(4-methylpyridin-3-yl)-5-phenyl-1H-pyrazol-4-yl]acetate (see Table 3, Example 3-76)

0.445 g (6.345 mmol) of prop-2-yn-1-ol and a drop of concentrated sulfuric acid were added to 0.130 g (0.423 mmol) of [3-methyl-1-(4-methylpyridin-3-yl)-5-phenyl-1H-pyrazol-4-yl]acetic acid, and the mixture was stirred under reflux for 4 h. The solvent was removed under reduced pressure, a mixture of 10 ml of dichloromethane, 1.5 ml of diisopropylethylamine and 10 ml of water was added to the residue and the aqueous phase was extracted with 15 ml of dichloromethane. The combined organic phases were dried over sodium sulfate, and the solvent was removed under reduced pressure. Chromatography of the residue gave 0.083 g (57% of theory) of a light-beige solid of melting point 106° C.

Example A6

Cyclopropylmethyl [3-methyl-1-(4-methylpyridin-3-yl)-5-phenyl-1H-pyrazol-4-yl]acetate (see Table 3, Example 3-99)

0.296 g (2.575 mmol) of dichloro(methoxy)methane was added to 0.175 g (0.569 mmol) [3-methyl-1-(4-methylpyridin-3-yl)-5-phenyl-1H-pyrazol-4-yl]acetic acid, and the mixture was stirred at 60° C. for 2 h. Excess dichloro(methoxy)methane was removed under reduced pressure, 0.660 g (9.153 mmol) of cyclopropylmethanol was added to the residue and the mixture was stirred at 20° C. for 0.5 h. The solvent was removed under reduced pressure, a mixture of 10 ml of dichloromethane, 1.5 ml of diisopropylethylamine and 10 ml of water was added to the residue and the aqueous phase was extracted with 15 ml of dichloromethane. The combined organic phases were dried over sodium sulfate, and the solvent was removed under reduced pressure. Chromatography of the residue gave 0.123 g (59% of theory) of a colorless solid of m.p. 87° C.

The compounds described in the tables below are obtained according to or analogously to the examples described above.

In the tables:
F, Cl, Br, I=fluorine, chlorine, bromine or iodine, according to the customary chemical symbols for atoms
Me=methyl
MeO or OMe=methoxy
2,6-Me$_2$=2,6-dimethyl (for example as substitution on a phenyl ring)
Et=ethyl
Pr=n-propyl
iPr=isopropyl
iOPr=isopropyloxy
cypr=cyclopropyl
tBu=tertiary butyl Ph=phenyl
PhO=phenoxy
Ac=COCH$_3$=acetyl
Allyl=prop-2-en-1-yl
COOH=carboxyl.

In addition, the customary chemical symbols apply, such as, for example, CH$_2$ for methylene or CF$_3$ for trifluoromethyl or OH for hydroxyl. Correspondingly, composite meanings are defined as composed of the abbreviations mentioned.

In the physical data ("Data") column of the tables:
"NMR"=data according to the $^1$H-NMR spectrum (1H nuclear resonance data) are stated at the end of the table in question
"m.p."=melting point
"$(R^6)_n$=H"=unsubstituted cycle (n=0)

TABLE 1

Compounds of the formula (I'')

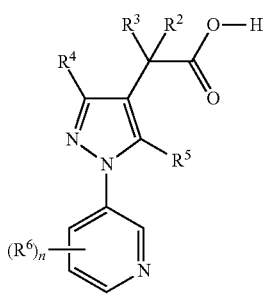

(I'')

| No. | R$^2$ | R$^3$ | R$^4$ | R$^5$ | $(R^6)_n$ | Data |
|---|---|---|---|---|---|---|
| 1-1 | H | H | Ph | Ph | H | m.p. 172° C. |
| 1-2 | H | Me | Ph | Ph | H | m.p. 192° C. |
| 1-3 | H | H | Me | 2-thienyl | 5-F | |
| 1-4 | H | H | Me | 2-furyl | H | NMR |
| 1-5 | H | H | Me | Ph | 6-OMe | m.p. 55° C. |
| 1-6 | Me | H | Me | Ph | 4-Me | |
| 1-7 | H | H | Me | Ph | 6-Cl | NMR |
| 1-8 | H | H | Me | Ph | 4-CF$_3$ | m.p. 158° C. |
| 1-9 | H | H | Me | Ph | 6-CF$_3$ | NMR |
| 1-10 | H | H | Me | Ph | 4-Me | m.p. 246° C. |
| 1-11 | H | H | Me | Ph | 2,6-Me$_2$ | NMR |
| 1-12 | H | H | Me | Ph | 2,6-Cl$_2$ | m.p. 147° C. |
| 1-13 | H | H | Me | 4-MeO-Ph | 4-Me | m.p. 202° C. |
| 1-14 | H | H | Me | 4-MeO-Ph | H | NMR |
| 1-15 | Me | H | Me | Ph | H | |
| 1-16 | H | H | Me | 4-Me-Ph | H | NMR |
| 1-17 | H | H | Me | 3-Cl-Ph | H | m.p. 163° C. |
| 1-18 | H | H | Me | 3-CF$_3$-Ph | H | NMR |
| 1-19 | H | H | Me | 3-CF$_3$-Ph | 4-Me | m.p. 202° C. |
| 1-20 | H | H | Me | 3,4-Cl$_2$-Ph | 4-Me | m.p. 192° C. |
| 1-21 | H | H | Me | 3-Cl-Ph | 4-Me | m.p. 172° C. |
| 1-22 | H | H | Me | 2-Cl-Ph | 4-Me | NMR |
| 1-23 | H | H | Me | 2,4-Cl$_2$-Ph | 4-Me | NMR |
| 1-24 | H | H | Me | 4-CF$_3$-Ph | 4-Me | m.p. 208° C. |
| 1-25 | H | H | Me | 4-Cl-Ph | 4-Me | m.p. 238° C. |
| 1-26 | H | H | Me | 4-Cl-Ph | H | m.p. 155° C. |
| 1-27 | H | H | Me | 3,4-dichloro-Ph | H | m.p. 147° C. |
| 1-28 | H | H | Me | 4-CF$_3$-Ph | H | m.p. 156° C. |
| 1-29 | H | H | Me | 4-Cl-Ph | 4-Cl | m.p. 228° C. |
| 1-30 | H | H | Me | Ph | 4-Cl | m.p. 223° C. |
| 1-31 | H | H | Me | 2-Cl-Ph | H | m.p. 238° C. |
| 1-32 | H | H | Me | 4-tBu-Ph | 4-Me | m.p. 256° C., NMR |
| 1-33 | H | H | Me | 3,5-Me$_2$-Ph | 4-Me | m.p. 221° C. |
| 1-34 | H | H | Me | Ph | 4-OMe | NMR |
| 1-35 | H | H | Me | 4-Cl-Ph | 4-OMe | m.p. 224° C. |
| 1-36 | H | H | Me | 4-Me-Ph | 4-Me | m.p. 234° C. |
| 1-37 | H | H | Me | 4-F-Ph | 4-Me | m.p. 227° C. |
| 1-38 | H | H | Me | 3-Me-Ph | 4-Me | m.p. 204° C. |

TABLE 1-continued

| 1-39 | H | H | Me | 4-(COOH)-Ph | 4-Me | m.p. 269° C. |
|---|---|---|---|---|---|---|
| 1-40 | H | H | Me | 3-Br-Ph | 4-Me | m.p. 184° C. |
| 1-41 | H | H | Me | 4-Ph-Ph | 4-Me | m.p. 232° C. |
| 1-42 | H | H | Me | 4-(COOH)-Ph | H | m.p. 169° C. |
| 1-43 | H | H | Me | 3,5-Me$_2$-Ph | H | m.p. 192° C. |
| 1-44 | H | H | Me | Ph | 4-SMe | |
| 1-45 | H | H | Me | 4-Cl-Ph | 4-SMe | m.p. 238° C. |
| 1-46 | H | H | Me | 3-Cl-4-Me-Ph | H | m.p. 187° C. |
| 1-47 | H | H | Me | 3-CF$_3$-4-Cl-Ph | H | m.p. 177° C. |
| 1-48 | H | H | Me | 3-CF$_3$-4-Cl-Ph | 4-Me | m.p. 176° C. |
| 1-49 | H | H | Me | 3-Cl-4-Me-Ph | 4-Me | m.p. 191° C. |
| 1-50 | H | H | Me | Ph | 5-Me | m.p. 165° C. |
| 1-51 | H | H | Me | 4-Cl-Ph | 5-Me | m.p. 185° C. |
| 1-52 | H | H | Me | 2-thienyl | 4-Me | m.p. 243° C. |
| 1-53 | H | H | Me | 3-Me-2-thienyl | 4-Me | m.p. 211° C. |
| 1-54 | H | H | Me | 4-Me-2-thienyl | 4-Me | m.p. 246° C. |
| 1-55 | H | H | Me | 5-Cl-2-thienyl | 4-Me | m.p. 266° C. |
| 1-56 | H | H | Me | 3-thienyl | 4-Me | m.p. 247° C. |
| 1-57 | H | H | Me | 2-thienyl | H | m.p. 190° C. |
| 1-58 | H | H | Me | 3-Me-2-thienyl | H | m.p. 145° C. |
| 1-59 | H | H | Me | 4-Me-2-thienyl | H | m.p. 170° C. |
| 1-60 | H | H | Me | 5-Cl-2-thienyl | H | m.p. 210° C. |
| 1-61 | H | H | Me | 5-Me-2-thienyl | H | m.p. 216° C. |
| 1-62 | H | H | Me | 6-MeO-pyridin-3-yl | H | m.p. 162° C. |
| 1-63 | H | H | Me | 3-thienyl | H | m.p. 189° C. |
| 1-64 | H | H | Me | 4-Cl-Ph | 4-S(O)Me | m.p. 216° C. |
| 1-65 | H | H | Me | 4-Br-Ph | 4-Me | |
| 1-66 | H | H | Me | 1,3-benzodioxol-5-yl | 4-Me | |
| 1-67 | H | H | Me | 4-I-Ph | 4-Me | |
| 1-68 | H | H | Me | 3,5-Cl$_2$-Ph | 4-Me | |
| 1-69 | H | H | Me | 4-PhO-Ph | 4-Me | |
| 1-70 | H | H | Me | 6-OH-pyridin-3-yl | H | m.p. 255° C. |
| 1-71 | H | H | Me | Ph | 4-S(O)Me | NMR |
| 1-72 | H | H | H | Ph | H | m.p. 145° C. |
| 1-73 | H | H | H | Ph | 4-Me | m.p. 208° C. |
| 1-74 | H | H | Et | Ph | H | |
| 1-75 | H | H | n-Pr | Ph | H | |
| 1-76 | H | H | CH$_2$Cl | Ph | H | |
| 1-77 | H | H | CHCl$_2$ | Ph | H | |
| 1-78 | H | H | CH$_2$F | Ph | H | |
| 1-79 | H | H | CHF$_2$ | Ph | H | |
| 1-80 | H | H | Cl | Ph | H | |
| 1-81 | H | H | Et | Ph | 4-Me | |
| 1-82 | H | H | n-Pr | Ph | 4-Me | |
| 1-83 | H | H | CH$_2$Cl | Ph | 4-Me | |
| 1-84 | H | H | CHCl$_2$ | Ph | 4-Me | |
| 1-85 | H | H | CH$_2$F | Ph | 4-Me | |
| 1-86 | H | H | CHF$_2$ | Ph | 4-Me | |
| 1-87 | H | H | Cl | Ph | 4-Me | |
| 1-88 | H | H | Et | 4-Cl-Ph | H | |
| 1-89 | H | H | n-Pr | 4-Cl-Ph | H | |
| 1-90 | H | H | CH$_2$Cl | 4-Cl-Ph | H | |
| 1-91 | H | H | CHCl$_2$ | 4-Cl-Ph | H | |
| 1-92 | H | H | CH$_2$F | 4-Cl-Ph | H | |
| 1-93 | H | H | CHF$_2$ | 4-Cl-Ph | H | |
| 1-94 | H | H | Cl | 4-Cl-Ph | H | |
| 1-95 | H | H | Et | 4-Me-Ph | H | |
| 1-96 | H | H | n-Pr | 4-Me-Ph | H | |
| 1-97 | H | H | CH$_2$Cl | 4-Me-Ph | H | |
| 1-98 | H | H | CHCl$_2$ | 4-Me-Ph | H | |
| 1-99 | H | H | CH$_2$F | 4-Me-Ph | H | |
| 1-100 | H | H | CHF$_2$ | 4-Me-Ph | H | |
| 1-101 | H | H | Cl | 4-Me-Ph | H | |
| 1-102 | H | H | Et | 2-pyridyl | H | |
| 1-103 | H | H | n-Pr | 2-pyridyl | H | |
| 1-104 | H | H | CH$_2$Cl | 2-pyridyl | H | |
| 1-105 | H | H | CHCl$_2$ | 2-pyridyl | H | |
| 1-106 | H | H | CH$_2$F | 2-pyridyl | H | |
| 1-107 | H | H | CHF$_2$ | 2-pyridyl | H | |
| 1-108 | H | H | Cl | 2-pyridyl | H | |
| 1-109 | H | H | Me | 2-pyridyl | H | m.p. 287° C. |
| 1-110 | H | H | Me | 5-Cl-pyridin-2-yl | H | m.p. 162° C. |
| 1-111 | H | H | Me | 5-Br-pyridin-2-yl | H | |
| 1-112 | H | H | Me | 5-F-pyridin-2-yl | H | |
| 1-113 | H | H | Me | 5-Me-pyridin-2-yl | H | m.p. 153° C. |
| 1-114 | H | H | Me | 2,4-Cl$_2$-Ph | H | |
| 1-115 | H | H | Me | 4-CH$_2$COOH-Ph | 4-Me | |

TABLE 1-continued

| No. | | | | | | |
|---|---|---|---|---|---|---|
| 1-116 | H | H | Me | 3,4-Me2-Ph | 4-Me | |
| 1-117 | H | H | Me | 4-Br-Ph | 4-Me | |
| 1-118 | H | H | Me | 3,4-Me2-Ph | H | |
| 1-119 | H | H | Me | 3-Me-Ph | H | |
| 1-120 | H | H | Me | 4-F-Ph | H | NMR |
| 1-121 | H | H | Me | 4-(Me-CO)-Ph | H | |
| 1-122 | H | H | Me | 4-tBu-Ph | H | |
| 1-123 | H | H | Me | 4-Cl-3-Me-Ph | H | |
| 1-124 | H | H | n-Pr | 4-Cl-Ph | 4-Me | NMR |
| 1-125 | H | H | Me | 3-pyridyl | H | |
| 1-126 | H | H | Me | 4-pyridyl | H | |
| 1-127 | H | H | C(O)OMe | Ph | H | |
| 1-128 | H | H | Me | 6-Me-pyridin-3-yl | H | |
| 1-129 | H | H | Me | 4-Cl-Ph | 4-SO2Me | |
| 1-130 | H | H | Me | 3-pyridyl | 4-Me | |
| 1-131 | H | H | Me | 2-3-Cl2-Ph | 4-Me | |
| 1-132 | H | H | Me | 2-pyridyl | 4-Me | |
| 1-133 | H | H | H | 4-Cl-Ph | 4-Me | |
| 1-134 | H | H | Me | 6-Cl-pyridin-3-yl | H | |
| 1-135 | H | H | Me | Ph | 2-Me | m.p. 222° C. |
| 1-136 | H | H | Me | 4-Me-pyridin-2-yl | H | m.p. 181° C. |
| 1-137 | H | H | Me | 4-Me-pyridin-2-yl | 4-Me | m.p. 188° C. |
| 1-138 | H | H | Me | 4-Me-pyridin-2-yl | 4-Cl | |
| 1-139 | H | H | Me | 4-Me-pyridin-2-yl | 4-F | |
| 1-140 | H | H | Me | 4-F-pyridin-2-yl | H | |
| 1-141 | H | H | Me | 4-Cl-pyridin-2-yl | H | |
| 1-142 | H | H | Me | 4-Br-pyridin-2-yl | H | |
| 1-143 | H | H | Me | 4-OMe-pyridin-2-yl | H | |
| 1-144 | H | H | Me | 5-CF3-pyridin-2-yl | H | m.p. 135° C. |
| 1-145 | H | H | Me | 6-OMe-pyridin-2-yl | H | NMR |
| 1-146 | H | H | cyPr | 4-Cl-Ph | H | m.p. 109° C. |
| 1-147 | H | H | CN | 4-Cl-Ph | H | |
| 1-148 | H | H | CN | 4-Cl-Ph | 4-Me | |
| 1-149 | H | H | CN | 4-Me-Ph | H | |
| 1-150 | H | H | CN | 4-Me-Ph | 4-Me | |
| 1-151 | H | H | CN | Ph | H | |
| 1-152 | H | H | CN | Ph | 4-Me | |
| 1-153 | H | H | CN | 2-pyridyl | H | |
| 1-154 | H | H | CN | 3-pyridyl | H | |
| 1-155 | H | H | CN | 5-Cl-pyridin-2-yl | H | |
| 1-156 | H | H | CN | 5-Br-pyridin-2-yl | H | |
| 1-157 | H | H | CN | 5-F-pyridin-2-yl | H | |
| 1-158 | H | H | CN | 5-Me-pyridin-2-yl | H | |
| 1-159 | H | H | CN | 6-Me-pyridin-3-yl | H | |
| 1-160 | H | H | CN | 4-Me-pyridin-2-yl | H | |
| 1-161 | H | H | CN | 4-F-pyridin-2-yl | H | |
| 1-162 | H | H | CN | 4-Cl-pyridin-2-yl | H | |
| 1-163 | H | H | CN | 4-Br-pyridin-2-yl | H | |
| 1-164 | H | H | CN | 4-OMe-pyridin-2-yl | H | |
| 1-165 | H | H | formyl | 4-Cl-Ph | H | |
| 1-166 | H | H | formyl | 4-Cl-Ph | 4-Me | |
| 1-167 | H | H | formyl | 4-Me-Ph | H | |
| 1-168 | H | H | formyl | 4-Me-Ph | 4-Me | |
| 1-169 | H | H | formyl | Ph | H | |
| 1-170 | H | H | formyl | Ph | 4-Me | |
| 1-171 | H | H | formyl | 2-pyridyl | H | |
| 1-172 | H | H | formyl | 3-pyridyl | H | |
| 1-173 | H | H | formyl | 5-Cl-pyridin-2-yl | H | |
| 1-174 | H | H | formyl | 5-Br-pyridin-2-yl | H | |
| 1-175 | H | H | formyl | 5-F-pyridin-2-yl | H | |
| 1-176 | H | H | formyl | 5-Me-pyridin-2-yl | H | |
| 1-177 | H | H | formyl | 6-Me-pyridin-3-yl | H | |
| 1-178 | H | H | formyl | 4-Me-pyridin-2-yl | H | |
| 1-179 | H | H | formyl | 4-F-pyridin-2-yl | H | |
| 1-180 | H | H | formyl | 4-Cl-pyridin-2-yl | H | |
| 1-181 | H | H | formyl | 4-Br-pyridin-2-yl | H | |
| 1-182 | H | H | formyl | 4-OMe-pyridin-2-yl | H | |
| 1-183 | H | H | CH2OH | 5-Me-pyridin-2-yl | H | |
| 1-184 | H | H | CH2OH | 4-Cl-Ph | H | |
| 1-185 | H | H | CH2OH | 4-Me-pyridin-2-yl | H | |
| 1-186 | H | H | CH2OH | 4-Me-Ph | H | |
| 1-187 | H | H | CH2OH | Ph | H | |
| 1-188 | H | H | CH2OH | 2-pyridyl | H | |

"NMR" of the exemplary compounds were in each case measured as $^1$H-NMR spectra at 300 MHz (CDCl$_3$) ($^1$H nuclear resonance data). Characteristic chemical shifts δ (ppm) for some exemplary compounds are listed below:

| Ex. No.: | δ (ppm) |
|---|---|
| 1-4: | 2.38 (s, 3 H), 3.60 (s, 2 H), 6.47 (m, 2 H), 7.43 (m, 1 H) |
| 1-7: | 2.37 (s, 3 H), 3.41 (s, 2 H), 7.23 (m, 3 H), 7.4 (m, 3 H), 7.57 (dd, 1 H), 8.21 (d, 1 H) |
| 1-9: | 7.60 (d, 1 H), 7.77 (dd, 1 H), 8.58 (d, 1 H) |
| 1-11: | 2.18 (s, 3 H), 2.23 (s, 3 H), 2.50 (s, 3 H), 7.85 (d, 1 H) |
| 1-14: | 3.80 (s, 3 H), 6.90 (d, 2 H), 7.17 (d, 2 H) |
| 1-16: | 2.37 (s, 3 H), 2.38 (s, 3 H), 3.42 (s, 2 H), 7.10 (d, 2 H), 7.18 (d, 2 H) |
| 1-18: | 2.38 (s, 3 H), 3.41 (s, 2 H), 7.41 (d, 1 H), 7.51 (t, 1 H), 7.55 (s, 1 H), 7.63 (d, 1 H), 8.49 (m, 2 H) |
| 1-22: | 2.27 (s, 3 H), 2.38 (s, 3 H), 3.35 (d, 1 H), 3.42 (d, 1 H), 7.18 (d, 1 H), 8.23 (s, 1 H), 8.35 (d, 1 H) |
| 1-23: | 2.25 (s, 3 H), 2.39 (s, 3 H), 3.35 (d, 1 H), 3.42 (d, 1 H), 7.37 (s, 1 H), 8.25 (s, 1 H), 8.39 (d, 1 H) |
| 1-31: | 2.40 (s, 3 H), 3.30 (d, 1 H), 3.41 (d, 1 H), 7.61 (m, 1 H), 8.45 (m, 2 H) |
| 1-34: | 2.38 (s, 3 H), 3.46 (s, 2 H), 3.59 (s, 3 H), 6.78 (d, 1 H), 8.45 (d, 1 H), 8.50 (s, 1 H) |
| 1-71: | 2.37 (s, 3 H), 2.95 (s, 3 H), 3.40 (d, 1 H), 3.48 (d, 1 H), 8.08 (d, 1 H), 8.12 (s, 1 H), 8.70 (d, 1 H) |
| 1-120: | 2.39 (s, 3 H), 3.42 (s, 2 H), 7.08 (t, 1 H) |
| 1-124: | 1.02 (t, 3 H), 1.77 (sext, 2 H), 2.08 (s, 3 H), 2.70 (t, 2 H), 3.44 (s, 2 H), 7.12 (d, 2 H), 7.19 (d, 1 H), 7.27 (d, 2 H), 8.39 (d, 1 H), 8.42 (d, 1 H) |
| 1-145: | 2.42 (s, 3 H), 3.60 (s, 2 H), 3.85 (s, 3 H), 6.69 (d, 1 H), 6.79 (d, 1 H), 7.58 (dd, 1 H) |

TABLE 2

Compounds of the formula (I''')

(I''')

| No. | R$^2$ | R$^3$ | R$^4$ | R$^5$ | (R$^6$)$_n$ | Data |
|---|---|---|---|---|---|---|
| 2-1 | H | H | Ph | Ph | H | NMR |
| 2-2 | H | H | Me | Ph | H | NMR |
| 2-3 | H | H | Me | 2-thienyl | 5-F | |
| 2-4 | H | H | Me | 2-furyl | H | NMR |
| 2-5 | H | H | Me | Ph | 6-OMe | NMR |
| 2-6 | Me | H | Me | Ph | 4-Me | |
| 2-7 | H | H | Me | Ph | 6-Cl | NMR |
| 2-8 | H | H | Me | Ph | 4-CF3 | NMR |
| 2-9 | H | H | Me | Ph | 6-CF3 | NMR |
| 2-10 | H | H | Me | Ph | 4-Me | NMR |
| 2-11 | H | H | Me | Ph | 2,6-Me2 | |
| 2-12 | H | H | Me | Ph | 2,6-Cl2 | NMR |
| 2-13 | H | H | Me | 4-MeO-Ph | 4-Me | |
| 2-14 | H | H | Me | 4-MeO-Ph | H | NMR |
| 2-15 | Me | H | Me | Ph | H | |
| 2-16 | H | H | Me | 4-Me-Ph | H | NMR |
| 2-17 | H | H | Me | 3-Cl-Ph | H | NMR |
| 2-18 | H | H | Me | 3-CF3-Ph | H | NMR |
| 2-19 | H | H | Me | 3-CF3-Ph | 4-Me | NMR |

TABLE 2-continued

| | | | | | |
|---|---|---|---|---|---|
| 2-20 | H | H | Me | 3,4-Cl$_2$-Ph | 4-Me | NMR |
| 2-21 | H | H | Me | 3-Cl-Ph | 4-Me | NMR |
| 2-22 | H | H | Me | 2-Cl-Ph | 4-Me | NMR |
| 2-23 | H | H | Me | 2,4-Cl$_2$-Ph | 4-Me | NMR |
| 2-24 | H | H | Me | 4-CF$_3$-Ph | 4-Me | m.p. 96° C. |
| 2-25 | H | H | Me | 4-Cl-Ph | 4-Me | NMR |
| 2-26 | H | H | Me | 4-Cl-Ph | H | NMR |
| 2-27 | H | H | Me | 3,4-Cl$_2$-Ph | H | NMR |
| 2-28 | H | H | Me | 4-CF$_3$-Ph | H | NMR |
| 2-29 | H | H | Me | 4-Cl-Ph | 4-Cl | NMR |
| 2-30 | H | H | Me | Ph | 4-Cl | m.p. 100° C. |
| 2-31 | H | H | Me | 2-Cl-Ph | H | NMR |
| 2-32 | H | H | Me | 4-tBu-Ph | 4-Me | NMR |
| 2-33 | H | H | Me | 3,5-Me$_2$-Ph | 4-Me | |
| 2-34 | H | H | Me | Ph | 4-OMe | m.p. 144° C. |
| 2-35 | H | H | Me | 4-Cl-Ph | 4-OMe | NMR |
| 2-36 | H | H | Me | 4-Me-Ph | 4-Me | NMR |
| 2-37 | H | H | Me | 4-F-Ph | 4-Me | NMR |
| 2-38 | H | H | Me | 3-Me-Ph | 4-Me | NMR |
| 2-39 | H | H | Me | 4-COOH-Ph | 4-Me | |
| 2-40 | H | H | Me | 3-Br-Ph | 4-Me | |
| 2-41 | H | H | Me | 4-Ph-Ph | 4-Me | m.p. 153° C. |
| 2-42 | H | H | Me | 4-COOH-Ph | H | |
| 2-43 | H | H | Me | 3,5-Me$_2$-Ph | H | NMR |
| 2-44 | H | H | Me | Ph | 4-SMe | NMR |
| 2-45 | H | H | Me | 4-Cl-Ph | 4-SMe | NMR |
| 2-46 | H | H | Me | 3-Cl-4-Me-Ph | H | NMR |
| 2-47 | H | H | Me | 3-CF$_3$-4-chloro-Ph | H | NMR |
| 2-48 | H | H | Me | 3-CF$_3$-4-Cl-Ph | 4-Me | NMR |
| 2-49 | H | H | Me | 3-Cl-4-Me-Ph | 4-Me | NMR |
| 2-50 | H | H | Me | Ph | 5-Me | NMR |
| 2-51 | H | H | Me | 4-Cl-Ph | 5-Me | NMR |
| 2-52 | H | H | Me | 2-thienyl | 4-Me | m.p. 99° C. |
| 2-53 | H | H | Me | 3-Me-2-thienyl | 4-Me | NMR |
| 2-54 | H | H | Me | 4-Me-2-thienyl | 4-Me | m.p. 94° C. |
| 2-55 | H | H | Me | 5-Cl-2-thienyl | 4-Me | m.p. 105° C. |
| 2-56 | H | H | Me | 3-thienyl | 4-Me | m.p. 104° C. |
| 2-57 | H | H | Me | 2-thienyl | H | NMR |
| 2-58 | H | H | Me | 3-Me-2-thienyl | H | NMR |
| 2-59 | H | H | Me | 4-Me-2-thienyl | H | NMR |
| 2-60 | H | H | Me | 5-Cl-2-thienyl | H | NMR |
| 2-61 | H | H | Me | 5-Me-2-thienyl | H | NMR |
| 2-62 | H | H | Me | 6-MeO-pyridin-3-yl | H | NMR |
| 2-63 | H | H | Me | 3-thienyl | H | NMR |
| 2-64 | H | H | Me | 4-Cl-Ph | 4-S(O)Me | m.p. 161° C. |
| 2-65 | H | H | Me | 4-Br-Ph | 4-Me | |
| 2-66 | H | H | Me | 1,3-Benzodioxol-5-yl | 4-Me | m.p. 91° C. |
| 2-67 | H | H | Me | 4-I-Ph | 4-Me | |
| 2-68 | H | H | Me | 3,5-Cl$_2$-Ph | 4-Me | m.p. 112° C. |
| 2-69 | H | H | Me | 4-PhO-Ph | 4-Me | |
| 2-70 | H | H | Me | 6-OH-pyridin-3-yl | H | m.p. 171° C. |
| 2-71 | H | H | Me | Ph | 4-S(O)Me | m.p. 163° C. |
| 2-72 | H | H | H | Ph | H | NMR |
| 2-73 | H | H | H | Ph | 4-Me | NMR |
| 2-74 | H | H | Et | Ph | H | NMR |
| 2-75 | H | H | n-Pr | Ph | H | |
| 2-76 | H | H | CH$_2$Cl | Ph | H | |
| 2-77 | H | H | CHCH$_2$ | Ph | H | |
| 2-78 | H | H | CH$_2$F | Ph | H | |
| 2-79 | H | H | CHF$_2$ | Ph | H | NMR |
| 2-80 | H | H | Cl | Ph | H | |
| 2-81 | H | H | Et | Ph | 4-Me | |
| 2-82 | H | H | n-Pr | Ph | 4-Me | |
| 2-83 | H | H | CH$_2$Cl | Ph | 4-Me | |
| 2-84 | H | H | CHCl$_2$ | Ph | 4-Me | |
| 2-85 | H | H | CH$_2$F | Ph | 4-Me | |
| 2-86 | H | H | CHF$_2$ | Ph | 4-Me | |
| 2-87 | H | H | Cl | Ph | 4-Me | |
| 2-88 | H | H | Et | 4-Cl-Ph | H | |
| 2-89 | H | H | n-Pr | 4-Cl-Ph | H | NMR |
| 2-90 | H | H | CH$_2$Cl | 4-Cl-Ph | H | |
| 2-91 | H | H | CHCl$_2$ | 4-Cl-Ph | H | |
| 2-92 | H | H | CH$_2$F | 4-Cl-Ph | H | |
| 2-93 | H | H | CHF$_2$ | 4-Cl-Ph | H | |
| 2-94 | H | H | Cl | 4-Cl-Ph | H | |
| 2-95 | H | H | Et | 4-Me-Ph | H | |
| 2-96 | H | H | n-Pr | 4-Me-Ph | H | |
| 2-97 | H | H | CH$_2$Cl | 4-Me-Ph | H | |
| 2-98 | H | H | CHCl$_2$ | 4-Me-Ph | H | |
| 2-99 | H | H | CH$_2$F | 4-Me-Ph | H | |
| 2-100 | H | H | CHF$_2$ | 4-Me-Ph | H | |
| 2-101 | H | H | Cl | 4-Me-Ph | H | |
| 2-102 | H | H | Et | 2-pyridyl | H | |
| 2-103 | H | H | n-Pr | 2-pyridyl | H | |
| 2-104 | H | H | CH$_2$Cl | 2-pyridyl | H | |
| 2-105 | H | H | CHCl$_2$ | 2-pyridyl | H | |
| 2-106 | H | H | CH$_2$F | 2-pyridyl | H | |
| 2-107 | H | H | CHF$_2$ | 2-pyridyl | H | |
| 2-108 | H | H | Cl | 2-pyridyl | H | |
| 2-109 | H | H | Me | 2-pyridyl | H | NMR |
| 2-110 | H | H | Me | 5-Cl-pyridin-2-yl | H | NMR |
| 2-111 | H | H | Me | 5-Br-pyridin-2-yl | H | |
| 2-112 | H | H | Me | 5-F-pyridin-2-yl | H | |
| 2-113 | H | H | Me | 5-Me-pyridin-2-yl | H | NMR |
| 2-114 | H | H | Me | 2,4-Cl$_2$-Ph | H | NMR |
| 2-115 | H | H | Me | 4-(CH$_2$COOH)-Ph | 4-Me | NMR |
| 2-116 | H | H | Me | 3,4-Me$_2$-Ph | 4-Me | NMR |
| 2-117 | H | H | Me | 4-Br-Ph | 4-Me | |
| 2-118 | H | H | Me | 3,4-Me$_2$-Ph | H | |
| 2-119 | H | H | Me | 3-Me-Ph | H | NMR |
| 2-120 | H | H | Me | 4-F-Ph | H | NMR |
| 2-121 | H | H | Me | 4-(Me-CO)-Ph | H | NMR |
| 2-122 | H | H | Me | 4-tBu-Ph | H | NMR |
| 2-123 | H | H | Me | 4-Cl-3-Me-Ph | H | NMR |
| 2-124 | H | H | n-Pr | 4-Cl-Ph | 4-Me | NMR |
| 2-125 | H | H | Me | 3-pyridyl | H | NMR |
| 2-126 | H | H | Me | 4-pyridyl | H | NMR |
| 2-127 | H | H | C(O)OMe | Ph | H | NMR |
| 2-128 | H | H | Me | 6-Me-pyridin-3-yl | H | NMR |
| 2-129 | H | H | Me | 4-Cl-Ph | 4-SO$_2$Me | |
| 2-130 | H | H | Me | 3-pyridyl | 4-Me | |
| 2-131 | H | H | Me | 2,3-Cl$_2$-Ph | 4-Me | m.p. 140° C. |
| 2-132 | H | H | Me | 2-pyridyl | 4-Me | NMR |
| 2-133 | H | H | H | 4-Cl-Ph | 4-Me | NMR |
| 2-134 | H | H | Me | 6-Cl-pyridin-3-yl | H | NMR |
| 2-135 | H | H | Me | Ph | 2-Me | NMR |
| 2-136 | H | H | Me | 4-Me-pyridin-2-yl | H | NMR |
| 2-137 | H | H | Me | 4-Me-pyridin-2-yl | 4-Me | |
| 2-138 | H | H | Me | 4-Me-pyridin-2-yl | 4-Cl | |
| 2-139 | H | H | Me | 4-Me-pyridin-2-yl | 4-F | |
| 2-140 | H | H | Me | 4-F-pyridin-2-yl | H | |
| 2-141 | H | H | Me | 4-Cl-pyridin-2-yl | H | |
| 2-142 | H | H | Me | 4-Br-pyridin-2-yl | H | |
| 2-143 | H | H | Me | 4-OMe-pyridin-2-yl | H | |
| 2-144 | H | H | Me | 5-CF$_3$-pyridin-2-yl | H | NMR |
| 2-145 | H | H | Me | 6-OMe-pyridin-2-yl | H | NMR |
| 2-146 | H | H | cyPr | 4-Cl-Ph | H | NMR |
| 2-147 | H | H | CN | 4-Cl-Ph | H | NMR |
| 2-148 | H | H | CN | 4-Cl-Ph | 4-Me | |
| 2-149 | H | H | CN | 4-Me-Ph | H | |
| 2-150 | H | H | CN | 4-Me-Ph | 4-Me | |
| 2-151 | H | H | CN | Ph | H | |
| 2-152 | H | H | CN | Ph | 4-Me | |
| 2-153 | H | H | CN | 2-pyridyl | H | |
| 2-154 | H | H | CN | 3-pyridyl | H | |
| 2-155 | H | H | CN | 5-Cl-pyridin-2-yl | H | |
| 2-156 | H | H | CN | 5-Br-pyridin-2-yl | H | |
| 2-157 | H | H | CN | 5-F-pyridin-2-yl | H | |
| 2-158 | H | H | CN | 5-Me-pyridin-2-yl | H | |
| 2-159 | H | H | CN | 6-Me-pyridin-3-yl | H | |
| 2-160 | H | H | CN | 4-Me-pyridin-2-yl | H | |
| 2-161 | H | H | CN | 4-F-pyridin-2-yl | H | |
| 2-162 | H | H | CN | 4-Cl-pyridin-2-yl | H | |
| 2-163 | H | H | CN | 4-Br-pyridin-2-yl | H | |
| 2-164 | H | H | CN | 4-OMe-pyridin-2-yl | H | |
| 2-165 | H | H | formyl | 4-Cl-Ph | H | NMR |
| 2-166 | H | H | formyl | 4-Cl-Ph | 4-Me | |
| 2-167 | H | H | formyl | 4-Me-Ph | H | |
| 2-168 | H | H | formyl | 4-Me-Ph | 4-Me | |
| 2-169 | H | H | formyl | Ph | H | |
| 2-170 | H | H | formyl | Ph | 4-Me | |

TABLE 2-continued

| | | | | | |
|---|---|---|---|---|---|
| 2-171 | H | H | formyl | 2-pyridyl | H |
| 2-172 | H | H | formyl | 3-pyridyl | H |
| 2-173 | H | H | formyl | 5-Cl-pyridin-2-yl | H |
| 2-174 | H | H | formyl | 5-Br-pyridin-2-yl | H |
| 2-175 | H | H | formyl | 5-F-pyridin-2-yl | H |
| 2-176 | H | H | formyl | 5-Me-pyridin-2-yl | H |
| 2-177 | H | H | formyl | 6-Me-pyridin-3-yl | H |
| 2-178 | H | H | formyl | 4-Me-pyridin-2-yl | H |
| 2-179 | H | H | formyl | 4-F-pyridin-2-yl | H |
| 2-180 | H | H | formyl | 4-Cl-pyridin-2-yl | H |
| 2-181 | H | H | formyl | 4-Br-pyridin-2-yl | H |
| 2-182 | H | H | formyl | 4-OMe-pyridin-2-yl | H |
| 2-183 | H | H | $CH_2OH$ | 5-Me-pyridin-2-yl | H |
| 2-184 | H | H | $CH_2OH$ | 4-Cl-Ph | H | NMR |
| 2-185 | H | H | $CH_2OH$ | 4-Me-pyridin-2-yl | H |
| 2-186 | H | H | $CH_2OH$ | 4-Me-Ph | H |
| 2-187 | H | H | $CH_2OH$ | Ph | H |
| 2-188 | H | H | $CH_2OH$ | 2-pyridyl | H |

"NMR" of the exemplary compounds were in each case measured as $^1$H-NMR spectra at 300 MHz (CDCl$_3$) ($^1$H nuclear resonance data). Characteristic chemical shifts δ (ppm) for some exemplary compounds are listed below:

Ex. No.: δ (ppm)

2-1: 3.59 (s, 2 H), 3.62 (s, 3 H), 7.2-7.8 (m, 12 H), 8.44 (dd, 1 H), 8.59 (d, 1 H)
2-2: 2.41 (s, 3 H), 3.50 (s, 2 H), 3.77 (s, 3 H), 7.63 (m, 1 H), 8.50 (dd, 1 H), 8.54 (d, 1 H)
2-4: 2.36 (s, 3 H), 3.58 (s, 2 H), 3.75 (s, 3 H), 6.47 (m, 2 H), 7.43 (m, 1 H)
2-5: 2.39 (s, 3 H), 3.43 (s, 2 H), 3.70 (s, 3 H), 3.90 (s, 3 H), 6.66 (d, 1 H), 7.98 (d, 1 H)
2-6: 1.42 (d, 3 H), 2.03 (s, 3 H), 2.38 (s, 3 H), 3.68 (s, 3 H), 3.73 (q, 1 H)
2-7: 2.37 (s, 3 H), 3.40 (s, 2 H), 3.70 (s, 3 H), 7.57 (dd, 1 H), 8.11 (d, 1 H)
2-8: 2.37 (s, 3 H), 3.43 (s, 2 H), 3.74 (s, 3 H), 7.60 (d, 1 H), 8.43 (s, 1 H), 8.73 (d, 1 H)
2-9: 2.38 (s, 3 H), 3.41 (s, 2 H), 3.70 (s, 3 H), 7.60 (d, 1 H), 7.78 (dd, 1 H), 8.57 (d, 1 H)
2-10: 2.03 (s, 3 H), 2.38 (s, 3 H), 3.43 (s, 2 H), 3.76 (s, 3 H), 8.40 (m, 2 H)
2-12: 2.37 (s, 3 H), 3.45 (s, 2 H), 3.71 (s, 3 H), 7.17-7.37 (m, 6 H), 7.59 (m, 1 H)
2-13: 2.02 (s, 3 H), 2.37 (s, 3 H), 3.45 (s, 2 H), 3.74 (s, 3 H), 3.78 (s, 3 H), 6.80 (d, 2 H), 7.07 (d, 2 H)
2-14: 2.37 (s, 3 H), 3.40 (s, 2 H), 3.72 (s, 3 H), 3.78 (s, 3 H), 6.90 (d, 2 H), 7.13 (d, 2 H)
2-16: 2.37 (s, 3 H), 2.38 (s, 3 H), 3.41 (s, 2 H), 3.72 (s, 3 H), 7.08 (d, 2 H), 7.17 (d, 2 H)
2-17: 2.37 (s, 3 H), 3.40 (s, 2 H), 3.71 (s, 3 H), 7.08 (dt, 1 H), 7.20-7.38 (m, 4 H), 7.58 (m, 1 H), 8.44 (m, 2 H)
2-18: 2.38 (s, 3 H), 3.40 (s, 2 H), 3.73 (s, 3 H), 7.39 (d, 1 H), 7.51 (t, 1 H), 7.55 (s, 1 H), 7.63 (d, 1 H)
2-19: 2.10 (s, 3 H), 2.38 (s, 3 H), 3.47 (s, 2 H), 3.76 (s, 3 H), 7.34 (d, 1 H), 7.41 (t, 1 H), 7.47 (s, 1 H), 7.58 (d, 1 H)
2-20: 2.06 (s, 3 H), 2.35 (s, 3 H), 3.42 (s, 2 H), 3.76 (s, 3 H), 6.95 (dd, 1 H), 7.15 (d, 1 H), 8.41 (d, 1 H)
2-21: 2.07 (s, 3 H), 2.35 (s, 3 H), 3.43 (s, 2 H), 3.75 (s, 3 H), 7.00 (dd, 1 H), 7.15 (d, 1 H), 8.40 (d, 1 H)
2-22: 2.25 (s, 3 H), 2.38 (s, 3 H), 3.35 (d, 1 H), 3.42 (d, 1 H), 3.62 (s, 3 H), 7.15 (s, 1 H), 8.23 (s, 1 H), 8.33 (d, 1 H)
2-23: 2.22 (s, 3 H), 2.38 (s, 3 H), 3.30 (d, 1 H), 3.40 (d, 1 H), 3.62 (s, 3 H), 8.20 (s, 1 H), 8.35 (d, 1 H)
2-25: 2.02 (s, 3 H), 2.37 (s, 3 H), 3.43 (s, 2 H), 3.75 (s, 3 H), 7.10 (d, 2 H), 7.26 (d, 2 H), 8.38 (d, 1 H), 8.42 (d, 1 H)
2-26: 2.37 (s, 3 H), 3.40 (s, 2 H), 3.72 (s, 3 H), 7.18 (d, 2 H), 7.25 (m, 1 H), 7.37 (d, 2 H), 7.58 (m, 1 H), 8.46 (m, 2 H)
2-27: 2.38 (s, 3 H), 3.41 (s, 2 H), 3.75 (s, 3 H), 7.05 (dd, 1 H), 7.40 (d, 1 H), 7.45 (d, 1 H)
2-28: 2.37 (s, 3 H), 3.40 (s, 2 H), 3.72 (s, 3 H), 7.38 (d, 2 H), 7.65 (d, 2 H)
2-29: 2.38 (s, 3 H), 3.45 (s, 2 H), 3.75 (s, 3 H), 7.15 (d, 2 H), 7.30 (d, 2 H), 7.36 (d, 1 H), 8.48 (d, 1 H), 8.55 (s, 1 H)
2-31: 2.44 (s, 3 H), 3.38 (d, 1 H), 3.48 (d, 1 H), 3.75 (s, 3 H), 8.50 (m, 2 H)
2-32: 1.25 (s, 9 H), 2.06 (s, 3 H), 2.37 (s, 3 H), 3.49 (s, 2 H), 3.76 (s, 3 H), 7.05 (d, 2 H), 7.15 (d, 1 H), 7.30 (d, 2 H), 8.37 (s, 1 H), 8.39 (d, 1 H)
2-35: 2.38 (s, 3 H), 3.43 (s, 2 H), 3.61 (s, 3 H), 3.73 (s, 3 H), 6.77 (d, 1 H), 7.14 (d, 2 H), 7.26 (d, 2 H), 8.43 (d, 1 H), 8.46 (s, 1 H)
2-36: 2.04 (s, 3 H), 2.30 (s, 3 H), 2.37 (s, 3 H), 3.43 (s, 2 H), 3.75 (s, 3 H), 7.02 (d, 2 H), 7.08 (d, 2 H)
2-37: 2.06 (s, 3 H), 2.38 (s, 3 H), 3.44 (s, 2 H), 3.75 (s, 3 H), 6.99 (t, 2 H), 8.38 (s, 1 H), 8.40 (d, 1 H)
2-38: 2.05 (s, 3 H), 2.25 (s, 3 H), 2.37 (s, 3 H), 3.47 (s, 2 H), 3.74 (s, 3 H), 6.92 (d, 1 H), 6.96 (s, 1 H)
2-43: 2.25 (s, 6 H), 2.37 (s, 3 H), 3.41 (s, 2 H), 3.72 (s, 3 H), 6.80 (s, 2 H), 7.00 (s, 1 H)
2-44: 2.37 (s, 3 H), 2.41 (s, 3 H), 3.46 (s, 2 H), 3.72 (s, 3 H), 7.09 (d, 1 H), 8.12 (s, 1 H), 8.38 (d, 1 H)
2-45: 2.37 (s, 3 H), 2.41 (s, 3 H), 3.43 (s, 2 H), 3.74 (s, 3 H), 7.09 (d, 1 H), 7.18 (d, 2 H), 7.27 (d, 2 H), 8.14 (s, 1 H), 8.39 (d, 1 H)
2-46: 2.36 (s, 3 H), 2.39 (s, 3 H), 3.41 (s, 2 H), 3.73 (s, 3 H), 6.98 (dd, 1 H), 7.21 (d, 1 H), 7.26 (m, 2 H)
2-47: 2.38 (s, 3 H), 3.40 (s, 2 H), 3.73 (s, 3 H), 7.30 (m, 2 H), 7.51 (d, 1 H)
2-48: 2.09 (s, 3 H), 2.38 (s, 3 H), 3.43 (s, 2 H), 3.77 (s, 3 H), 7.23 (dd, 1 H), 7.41 (d, 1H), 7.59 (d, 1 H)
2-49: 2.08 (s, 3 H), 2.34 (s, 3 H), 2.36 (s, 3 H), 3.43 (s, 2 H), 3.77 (s, 3 H), 6.90 (dd, 1 H), 7.12 (d, 1 H), 7.19 (d, 1 H)
2-50: 2.30 (s, 3 H), 2.37 (s, 3 H), 3.42 (s, 2 H), 3.71 (s, 3 H), 7.53 (t, 1 H), 8.12 (d, 1 H), 8.26 (d, 1 H)
2-51: 2.33 (s, 3 H), 2.37 (s, 3 H), 3.40 (s, 2 H), 3.71 (s, 3 H), 7.17 (d, 2 H), 7.37 (d, 2 H), 7.57 (t, 1 H), 8.10 (d, 1 H), 8.30 (d, 1 H)
2-53: 1.98 (s, 3 H), 2.20 (s, 3 H), 2.37 (s, 3 H), 3.43 (s, 2 H), 3.67 (s, 3 H), 6.79 (d, 1 H), 7.17 (d, 1 H), 7.23 (d, 1 H), 8.30 (s, 1 H), 8.39 (d, 1 H)
2-57: 2.36 (s, 3 H), 3.50 (s, 2 H), 3.72 (s, 3 H), 7.02 (m, 1 H), 7.08 (m, 1 H), 7.28 (m, 1 H), 7.41 (d, 1 H), 7.65 (dt, 1 H), 8.48 (dd, 1 H), 8.54 (d, 1 H)
2-58: 1.86 (s, 3 H), 2.37 (s, 3 H), 3,42 (broad d, 2 H), 3.68 (s, 3 H), 6.88 (d, 1 H), 7.23 (dd, 1 H), 7.38 (d, 1 H), 7.61 (dt, 1 H), 8.45 (dd, 1 H), 8.51 (d, 1 H)
2-59: 2.23 (s, 3 H), 2.34 (s, 3 H), 3.50 (s, 2 H), 3.72 (s, 3 H), 6.81 (d, 1 H), 6.98 (d, 1 H), 7.28 (dd, 1 H), 7.68 (dt, 1 H), 8.49 (dd, 1 H), 8.55 (d, 1 H)
2-60: 2.35 (s, 3 H), 3.49 (s, 2 H), 3.74 (s, 3 H), 6.82 (d, 1 H), 6.88 (d, 1 H), 7.31 (dd, 1 H), 7.69 (dt, 1 H), 8.53 (dd, 1 H), 8.59 (d, 1 H)
2-61: 2.36 (s, 3 H), 2.46 (d, 3 H), 3.50 (s, 2 H), 3.72 (s, 3 H), 6.70 (m, 1 H), 6.80 (d, 1 H), 7.29 (dd, 1 H), 7.70 (dt, 1 H), 8.49 (dd, 1 H), 8.57 (d, 1 H)
2-62: 2.38 (s, 3 H), 3.42 (s, 2 H), 3.72 (s, 3 H), 3.97 (s, 3 H), 6.74 (d, 1 H), 7.28 (dd, 1 H), 7.39 (dd, 1 H), 7.62 (dt, 1 H), 8.08 (d, 1 H), 8.49 (m, 2 H)
2-63: 2.37 (s, 3 H), 3.47 (s, 2 H), 3.75 (s, 3 H), 6.80 (dd, 1 H), 7.28 (dd, 1 H), 7.34 (dd, 1 H), 7.42 (dd, 1 H), 7.62 (dt, 1 H), 8.49 (dd, 1 H), 8.52 (d, 1 H)
2-72: 3.50 (s, 2 H), 3.70 (s, 3 H), 7.82 (s, 1 H), 8.47 (dd, 1 H), 8.50 (d, 1 H)

TABLE 2-continued

| | |
|---|---|
| 2-73: | 2.05 (s, 3 H), 3.56 (s, 2 H), 3.73 (s, 3 H), 7.82 (s, 1 H), 8.38 (s, 1 H), 8.41 (d, 1 H) |
| 2-74: | 1.34 (t, 3 H), 2.75 (q, 2 H), 3.43 (s, 2 H), 3.70 (s, 3 H) |
| 2-79: | 3.60 (s, 2 H), 3.73 (s, 3 H), 6.84 (t, 1 H, $^2J_{HF}$ = 55 Hz) |
| 2-89: | 1.03 (t, 3 H), 1.77 (sext, 2 H), 2.66 (t, 2 H), 3.41 (s, 2 H), 3.71 (s, 3 H), 7.19 (d, 2 H), 7.37 (d, 2 H) |
| 2-109: | 2.37 (s, 3 H), 3.60 (s, 2 H), 3.66 (s, 3 H), 7.25 (m, 3 H), 7.66 (m, 2 H), 8.39 (d, 1 H), 8.44 (dd, 1 H), 8.60 (m, 1 H) |
| 2-110: | 2.38 (s, 3 H), 3.60 (s, 2 H), 3.70 (s, 3 H), 8.40 (d, 1 H), 8.50 (dt, 1 H), 8.56 (d, 1 H) |
| 2-113: | 2.37 (s, 6 H), 3.59 (s, 2 H), 3.69 (s, 3 H), 8.38 (d, 1 H), 8.47 (m, 2 H) |
| 2-114: | 2.38 (s, 3 H), 3.25 (d, 1 H), 3.39 (d, 1 H), 3.65 (s, 3 H), 7.42 (m, 1 H), 8.40 (m, 1 H), 8.43 (m, 1 H) |
| 2-115: | 2.05 (s, 3 H), 2.38 (s, 3 H), 3.47 (s, 2 H), 3.74 (s, 3 H), 3.90 (s, 3 H), 7.23 (d, 2 H), 7.96 (d, 2 H) |
| 2-116: | 2.05 (s, 3 H), 2.18 (s, 3 H), 2.20 (s, 3 H), 2.35 (s, 3 H), 3.46 (s, 2 H), 3.74 (s, 3 H), 6.92 (s, 1 H), 7.01 (d, 1 H) |
| 2-118: | 2.20 (s, 3 H), 2.27 (s, 3 H), 2.37 (s, 3 H), 3.41 (s, 2 H), 3.72 (s, 3 H), 6.92 (d, 1 H), 6.99 (d, 1 H), 7.12 (d, 1 H) |
| 2-119: | 2.32 (s, 3 H), 2.38 (s, 3 H), 3.41 (s, 2 H), 3.72 (s, 3 H), 6.99 (d, 1 H), 7.02 (s, 1 H) |
| 2-120: | 2.38 (s, 3 H), 3.41 (s, 2 H), 3.73 (s, 3 H), 7.08 (t, 1 H) |
| 2-121: | 2.38 (s, 3 H), 3.42 (s, 2 H), 3.73 (s, 3 H), 3.94 (s, 3 H), 7.33 (d, 2 H), 8.04 (d, 2 H) |
| 2-122: | 1.32 (s, 9 H), 2.38 (s, 3 H), 3.42 (s, 2 H), 3.72 (s, 3 H), 7.13 (d, 2 H), 7.38 (d, 2 H) |
| 2-123: | 2.35 (s, 3 H), 2.37 (s, 3 H), 3.40 (s, 2 H), 3.73 (s, 3 H), 6.97 (dd, 1 H), 7.12 (d, 1 H), 7.33 (d, 1 H) |
| 2-124: | 1.03 (t, 3 H), 1.77 (sext, 2 H), 2.06 (s, 3 H), 2.67 (t, 2 H), 3.43 (s, 2 H), 3.72 (s, 3 H), 7.10 (d, 2 H), 7.14 (d, 1 H), 7.26 (d, 2 H), 8.38 (s, 1 H), 8.41 (d, 1 H) |
| 2-125: | 2.38 (s, 3 H), 3.42 (s, 2 H), 3.72 (s, 3 H), 7.26 (m, 1 H), 7.34 (m, 1 H), 7.59 (m, 2 H), 8.43-8.60 (m, 3 H), 8.62 (dd, 1 H) |
| 2-126: | 2.38 (s, 3 H), 3.43 (s, 2 H), 3.73 (s, 3 H), 7.18 (d, 2 H), 7.27 (dd, 1 H), 7.57 (dt, 1 H), 8.50 (d, 1 H), 8.53 (dd, 1 H), 8.63 (d, 2 H) |
| 2-127: | 3.72 (s, 3 H), 3.75 (s, 2 H), 3.97 (s, 3 H) |
| 2-128: | 2.38 (s, 3 H), 2.59 (s, 3 H), 3.42 (s, 2 H), 3.71 (s, 3 H), 7.18 (d, 1 H), 7.28 (dd, 1 H), 7.44 (dd, 1 H), 7.62 (dt, 1 H), 8.39 (d, 1 H), 8.45 (d, 1 H), 8.49 (dd, 1 H) |
| 2-132: | 2.09 (s, 3 H), 2.37 (s, 3 H), 3.69 (s, 3 H), 3.71 (s, 2 H), 7.57 (td, 1 H), 8.40 (s, 1 H), 8.42 (d, 1 H), 8.53 (m, 1 H) |
| 2-133: | 2.05 (s, 3 H), 3.52 (s, 2 H), 3.73 (s, 3 H), 7.07 (d, 2 H), 7.15 (d, 1 H), 7.28 (d, 2 H), 7.80 (s, 1 H), 8.37 (s, 1 H), 8.42 (d, 1 H) |
| 2-134: | 2.37 (s, 3 H), 3.40 (s, 2 H), 3.72 (s, 3 H), 7.28 (dd, 1 H), 7.35 (d, 1 H), 7.53 (dd, 1 H), 7.59 (dt, 1 H), 8.30 (d, 1 H), 8.45 (d, 1 H), 8.51 (dd, 1 H) |
| 2-135: | 2.22 (s, 3 H), 2.36 (s, 3 H), 3.45 (s, 2 H), 3.73 (s, 3 H), 7.48 (dd, 1 H), 8.46 (dd, 1 H) |
| 2-136: | 2.32 (s, 3 H), 2.38 (s, 3 H), 3.59 (s, 2 H), 3.69 (s, 3 H), 8.39 (d, 1 H), 8.48 (m, 2 H) |
| 2-144: | 2.39 (s, 3 H), 3.65 (s, 2 H), 3.70 (s, 3 H), 8.41 (d, 1 H), 8.54 (dt, 1 H), 8.89 (d, 1 H) |
| 2-145: | 2.37 (s, 3 H), 3.54 (s, 3 H), 3.65 (s, 2 H), 3.71 (s, 3 H), 6.68 (d, 1 H), 6.97 (d, 1 H), 7.58 (dd, 1 H) |
| 2-146: | 0.97 (m, 4 H), 1.88 (m, 1 H), 3.49 (s, 2 H), 3.73 (s, 3 H), 4.22 (t, 2 H), 7.17 (d, 2 H), 7.35 (d, 2 H) |
| 2-147: | 3.60 (s, 2 H), 3.74 (s, 3 H), 7.13 (d, 2 H), 7.33 (m, 1 H), 7.40 (d, 2 H), 7.63 (m, 1 H), 8.49 (m, 1 H), 8.60 (m, 1 H) |
| 2-165: | 3.70 (s, 3 H), 3.75 (s, 2 H), 7.15 (d, 2 H), 7.33 (m, 1 H), 7.40 (d, 2 H), 7.65 (m, 1 H), 8.57 (m, 1 H), 8.60 (m, 1 H), 10.13 (s, 1 H) |
| 2-184: | 3.52 (s, 2 H), 3.73 (s, 3 H), 4.80 (s, 2 H), 7.25 (d, 2 H), 7.27 (m, 1 H), 7.38 (d, 2 H), 7.60 (m, 1 H), 8.48 (m, 1 H), 8.50 (m, 1 H) |

TABLE 3

Compounds of the formula (I'''')

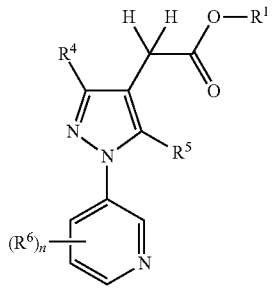

(I'''')

| No. | R$^1$ | R$^4$ | R$^5$ | (R$^6$)$_n$ | Data |
|---|---|---|---|---|---|
| 3-1 | Et | Me | 4-Cl-Ph | 4-Me | NMR |
| 3-2 | Et | Me | 4-Cl-Ph | 4-Me | |
| 3-3 | Et | Me | 2-thienyl | 4-Me | |
| 3-4 | Et | Me | 3-thienyl | 4-Me | |
| 3-5 | Et | Me | 3-Me-2-thienyl | 4-Me | |
| 3-6 | Et | Me | 4-Me-2-thienyl | 4-Me | |
| 3-7 | Et | Me | 5-Cl-2-thienyl | 4-Me | |
| 3-8 | Et | Me | 5-Me-2-thienyl | 4-Me | |
| 3-9 | Et | Me | 3-pyridyl | 4-Me | |
| 3-10 | Et | Me | 6-MeO-pyridin-3-yl | 4-Me | |
| 3-11 | Et | Me | 6-OH-pyridin-3-yl | 4-Me | |
| 3-12 | Et | Me | 6-Me-pyridin-3-yl | 4-Me | |
| 3-13 | Et | Me | 4-Me-Ph | 4-Me | |
| 3-14 | Et | Me | 4-Br-Ph | 4-Me | |
| 3-15 | Et | Me | 4-F-Ph | 4-Me | |
| 3-16 | Et | Me | 5-Cl-pyridin-2-yl | 4-Me | |
| 3-17 | Et | Me | 5-Br-pyridin-2-yl | 4-Me | |
| 3-18 | Et | Me | 5-F-pyridin-2-yl | 4-Me | |
| 3-19 | Et | Me | 5-Me-pyridin-2-yl | 4-Me | |
| 3-20 | Et | Me | 2-pyridyl | 4-Me | |

TABLE 3-continued

| | | | | | |
|---|---|---|---|---|---|
| 3-21 | Et | Me | 4-pyridyl | 4-Me | |
| 3-22 | Pr | Me | Ph | H | |
| 3-23 | Pr | Me | 4-Cl-Ph | H | |
| 3-24 | Pr | Me | 2-thienyl | H | |
| 3-25 | Pr | Me | 3-pyridyl | H | |
| 3-26 | Pr | Me | 6-Me-pyridin-3-yl | H | |
| 3-27 | Pr | Me | 4-Me-Ph | H | |
| 3-28 | Pr | Me | 4-Br-Ph | H | |
| 3-29 | Pr | Me | 4-F-Ph | H | |
| 3-30 | Pr | Me | 5-Cl-pyridin-2-yl | H | |
| 3-31 | Pr | Me | 5-Br-pyridin-2-yl | H | |
| 3-32 | Pr | Me | 5-F-pyridin-2-yl | H | |
| 3-33 | Pr | Me | 5-Me-pyridin-2-yl | H | |
| 3-34 | Pr | Me | 2-pyridyl | H | NMR |
| 3-35 | Pr | Me | 4-pyridyl | H | |
| 3-36 | i-Pr | Me | Ph | H | NMR |
| 3-37 | i-Pr | Me | 4-Cl-Ph | H | |
| 3-38 | i-Pr | Me | 2-thienyl | H | |
| 3-39 | i-Pr | Me | 3-pyridyl | H | |
| 3-40 | i-Pr | Me | 6-Me-pyridin-3-yl | H | |
| 3-41 | i-Pr | Me | 4-Me-Ph | H | |
| 3-42 | i-Pr | Me | 4-Br-Ph | H | |
| 3-43 | i-Pr | Me | 4-F-Ph | H | |
| 3-44 | i-Pr | Me | 5-Cl-pyridin-2-yl | H | |
| 3-45 | i-Pr | Me | 5-Br-pyridin-2-yl | H | |
| 3-46 | i-Pr | Me | 5-F-pyridin-2-yl | H | |
| 3-47 | i-Pr | Me | 5-Me-pyridin-2-yl | H | |
| 3-48 | i-Pr | Me | 2-pyridyl | H | NMR |
| 3-49 | i-Pr | Me | 4-pyridyl | H | |
| 3-50 | CH$_2$Ph | Me | Ph | H | m.p. 107° C. |
| 3-51 | CH$_2$Ph | Me | 4-Cl-Ph | H | |
| 3-52 | CH$_2$Ph | Me | 2-thienyl | H | |
| 3-53 | CH$_2$Ph | Me | 3-pyridyl | H | |
| 3-54 | prop-2-yn-1-yl | Me | Ph | H | NMR |
| 3-55 | prop-2-yn-1-yl | Me | 4-Cl-Ph | H | NMR |
| 3-56 | prop-2-yn-1-yl | Me | 2-thienyl | H | |
| 3-57 | prop-2-yn-1-yl | Me | 3-thienyl | H | |
| 3-58 | prop-2-yn-1-yl | Me | 3-Me-2-thienyl | H | |
| 3-59 | prop-2-yn-1-yl | Me | 4-Me-2-thienyl | H | |
| 3-60 | prop-2-yn-1-yl | Me | 5-Cl-2-thienyl | H | |
| 3-61 | prop-2-yn-1-yl | Me | 5-Me-2-thienyl | H | |
| 3-62 | prop-2-yn-1-yl | Me | 3-pyridyl | H | |
| 3-63 | prop-2-yn-1-yl | Me | 6-MeO-pyridin-3-yl | H | NMR |
| 3-64 | prop-2-yn-1-yl | H | Ph | H | NMR |
| 3-65 | prop-2-yn-1-yl | Me | 6-Me-pyridin-3-yl | H | |
| 3-66 | prop-2-yn-1-yl | Me | 4-Me-Ph | H | |
| 3-67 | prop-2-yn-1-yl | Me | 4-Br-Ph | H | |
| 3-68 | prop-2-yn-1-yl | Me | 4-F-Ph | H | NMR |
| 3-69 | prop-2-yn-1-yl | Me | 5-Cl-pyridin-2-yl | H | |
| 3-70 | prop-2-yn-1-yl | Me | 5-Br-pyridin-2-yl | H | |
| 3-71 | prop-2-yn-1-yl | Me | 5-F-pyridin-2-yl | H | |
| 3-72 | prop-2-yn-1-yl | Me | 5-Me-pyridin-2-yl | H | |
| 3-73 | prop-2-yn-1-yl | Me | 2-pyridyl | H | NMR |
| 3-74 | prop-2-yn-1-yl | Me | 4-pyridyl | H | NMR |
| 3-75 | prop-2-yn-1-yl | Me | 4-Cl-Ph | 4-Me | NMR |
| 3-76 | prop-2-yn-1-yl | Me | Ph | 4-Me | m.p. 106° C. |
| 3-77 | cyclopropylmethyl | Me | Ph | H | NMR |
| 3-78 | cyclopropylmethyl | Me | 4-Cl-Ph | H | NMR |
| 3-79 | cyclopropylmethyl | Me | 2-thienyl | H | |
| 3-80 | cyclopropylmethyl | Me | 3-thienyl | H | |
| 3-81 | cyclopropylmethyl | Me | 3-Me-2-thienyl | H | |
| 3-82 | cyclopropylmethyl | Me | 3-pyridyl | H | |
| 3-83 | cyclopropylmethyl | Me | 5-Cl-2-thienyl | H | |
| 3-84 | cyclopropylmethyl | Me | 5-Me-2-thienyl | H | |
| 3-85 | cyclopropylmethyl | Me | 4-Me-2-thienyl | H | NMR |
| 3-86 | cyclopropylmethyl | Me | 6-MeO-pyridin-3-yl | H | NMR |
| 3-87 | cyclopropylmethyl | Me | 6-OH-pyridin-3-yl | H | NMR |
| 3-88 | cyclopropylmethyl | Me | 6-Me-pyridin-3-yl | H | |
| 3-89 | cyclopropylmethyl | Me | 4-Me-Ph | H | |
| 3-90 | cyclopropylmethyl | Me | 4-Br-Ph | H | |
| 3-91 | cyclopropylmethyl | Me | 4-F-Ph | H | NMR |
| 3-92 | cyclopropylmethyl | Me | 5-Cl-pyridin-2-yl | H | |
| 3-93 | cyclopropylmethyl | Me | 5-Br-pyridin-2-yl | H | |
| 3-94 | cyclopropylmethyl | Me | 5-F-pyridin-2-yl | H | |
| 3-95 | cyclopropylmethyl | Me | 5-Me-pyridin-2-yl | H | |
| 3-96 | cyclopropylmethyl | Me | 2-pyridyl | H | |
| 3-97 | cyclopropylmethyl | Me | 4-pyridyl | H | |
| 3-98 | cyclopropylmethyl | Me | 4-Cl-Ph | 4-Me | NMR |
| 3-99 | cyclopropylmethyl | Me | Ph | 4-Me | m.p. 87° C. |
| 3-100 | cyclopropylmethyl | H | Ph | H | NMR |

TABLE 3-continued

| | | | | | |
|---|---|---|---|---|---|
| 3-101 | 3,3-dichloro-2-fluoroprop-2-en-1-yl | Me | Ph | H | NMR |
| 3-102 | 3,3-dichloro-2-fluoroprop-2-en-1-yl | Me | 4-Cl-Ph | H | |
| 3-103 | 3,3-dichloro-2-fluoroprop-2-en-1-yl | Me | 2-thienyl | H | |
| 3-104 | 3,3-dichloro-2-fluoroprop-2-en-1-yl | Me | 3-pyridyl | H | |
| 3-105 | (1-methylcyclopropyl)-methyl | Me | Ph | H | NMR |
| 3-106 | (1-methylcyclopropyl)-methyl | Me | 4-Cl-Ph | H | |
| 3-107 | (1-methylcyclopropyl)-methyl | Me | 2-thienyl | H | |
| 3-108 | (1-methylcyclopropyl)-methyl | Me | 3-pyridyl | H | |
| 3-109 | 4-chlorobut-2-yn-1-yl | Me | Ph | H | NMR |
| 3-110 | 4-chlorobut-2-yn-1-yl | Me | 4-Cl-Ph | H | |
| 3-111 | 4-chlorobut-2-yn-1-yl | Me | 2-thienyl | H | |
| 3-112 | 4-chlorobut-2-yn-1-yl | Me | 3-pyridyl | H | |
| 3-113 | (2,2-dichlorocyclopropyl)-methyl | Me | Ph | H | NMR |
| 3-114 | (2,2-dichlorocyclopropyl)-methyl | Me | 4-Cl-Ph | H | |
| 3-115 | (2,2-dichlorocyclopropyl)-methyl | Me | 2-thienyl | H | |
| 3-116 | (2,2-dichlorocyclopropyl)-methyl | Me | 3-pyridyl | H | |
| 3-117 | but-2-yn-1-yl | Me | Ph | H | NMR |
| 3-118 | but-2-yn-1-yl | Me | 4-Cl-Ph | H | NMR |
| 3-119 | but-2-yn-1-yl | Me | 2-thienyl | H | |
| 3-120 | but-2-yn-1-yl | Me | 3-thienyl | H | |
| 3-121 | but-2-yn-1-yl | Me | 3-Me-2-thienyl | H | |
| 3-122 | but-2-yn-1-yl | Me | 4-Me-2-thienyl | H | |
| 3-123 | but-2-yn-1-yl | Me | 5-Cl-2-thienyl | H | |
| 3-124 | but-2-yn-1-yl | Me | 5-Me-2-thienyl | H | |
| 3-125 | but-2-yn-1-yl | Me | 3-pyridyl | H | |
| 3-126 | but-2-yn-1-yl | Me | 6-MeO-pyridin-3-yl | H | |
| 3-127 | but-2-yn-1-yl | H | Ph | H | |
| 3-128 | but-2-yn-1-yl | Me | 6-Me-pyridin-3-yl | H | |
| 3-129 | but-2-yn-1-yl | Me | 4-Me-Ph | H | |
| 3-130 | but-2-yn-1-yl | Me | 4-Br-Ph | H | |
| 3-131 | but-2-yn-1-yl | Me | 4-F-Ph | H | |
| 3-132 | but-2-yn-1-yl | Me | 5-Cl-pyridin-2-yl | H | |
| 3-133 | but-2-yn-1-yl | Me | 5-Br-pyridin-2-yl | H | |
| 3-134 | but-2-yn-1-yl | Me | 5-F-pyridin-2-yl | H | |
| 3-135 | but-2-yn-1-yl | Me | 5-Me-pyridin-2-yl | H | |
| 3-136 | but-2-yn-1-yl | Me | 2-pyridyl | H | NMR |
| 3-137 | but-2-yn-1-yl | Me | 4-pyridyl | H | |
| 3-138 | but-2-yn-1-yl | Me | 4-Cl-Ph | 4-Me | |
| 3-139 | but-2-yn-1-yl | Me | Ph | 4-Me | NMR |
| 3-140 | 1-methylprop-2-yn-1-yl | Me | Ph | H | NMR |
| 3-141 | 1-methylprop-2-yn-1-yl | Me | 4-Cl-Ph | H | |
| 3-142 | 1-methylprop-2-yn-1-yl | Me | 2-thienyl | H | |
| 3-143 | 1-methylprop-2-yn-1-yl | Me | 3-pyridyl | H | |
| 3-144 | 1-cyclopropylethyl | Me | Ph | H | NMR |
| 3-145 | 1-cyclopropylethyl | Me | 4-Cl-Ph | H | |
| 3-146 | 1-cyclopropylethyl | Me | 2-thienyl | H | |
| 3-147 | 1-cyclopropylethyl | Me | 3-pyridyl | H | |
| 3-148 | allyl | Me | Ph | H | NMR |
| 3-149 | allyl | Me | 4-Cl-Ph | H | |
| 3-150 | allyl | Me | 2-thienyl | H | |
| 3-151 | allyl | Me | 3-pyridyl | H | |
| 3-152 | 3-methylbut-2-en-1-yl | Me | Ph | H | NMR |
| 3-153 | 3-methylbut-2-en-1-yl | Me | 4-Cl-Ph | H | |
| 3-154 | 3-methylbut-2-en-1-yl | Me | 2-thienyl | H | |
| 3-155 | 3-methylbut-2-en-1-yl | Me | 3-pyridyl | H | |
| 3-156 | 2-methylprop-2-en-1-yl | Me | Ph | H | NMR |
| 3-157 | 2-methylprop-2-en-1-yl | Me | 4-Cl-Ph | H | |
| 3-158 | 2-methylprop-2-en-1-yl | Me | 2-thienyl | H | |
| 3-159 | 2-methylprop-2-en-1-yl | Me | 3-pyridyl | H | |
| 3-160 | (2E)-1-methylbut-2-en-1-yl | Me | Ph | H | NMR |
| 3-161 | (2E)-1-methylbut-2-en-1-yl | Me | 4-Cl-Ph | H | |
| 3-162 | (2E)-1-methylbut-2-en-1-yl | Me | 2-thienyl | H | |
| 3-163 | (2E)-1-methylbut-2-en-1-yl | Me | 3-pyridyl | H | |
| 3-164 | 3-phenylprop-2-yn-1-yl | Me | Ph | H | NMR |
| 3-165 | 3-phenylprop-2-yn-1-yl | Me | 4-Cl-Ph | H | |
| 3-166 | 3-phenylprop-2-yn-1-yl | Me | 2-thienyl | H | |
| 3-167 | 3-phenylprop-2-yn-1-yl | Me | 3-pyridyl | H | |
| 3-168 | cyclobutylmethyl | Me | Ph | H | NMR |

TABLE 3-continued

| | | | | | |
|---|---|---|---|---|---|
| 3-169 | cyclobutylmethyl | Me | 4-Cl-Ph | H | |
| 3-170 | cyclobutylmethyl | Me | 2-thienyl | H | |
| 3-171 | cyclobutylmethyl | Me | 3-pyridyl | H | |
| 3-172 | cyclopentylmethyl | Me | Ph | H | NMR |
| 3-173 | cyclopentylmethyl | Me | 4-Cl-Ph | H | |
| 3-174 | cyclopentylmethyl | Me | 2-thienyl | H | |
| 3-175 | cyclopentylmethyl | Me | 3-pyridyl | H | |
| 3-176 | cyclohexylmethyl | Me | Ph | H | |
| 3-177 | cyclohexylmethyl | Me | 4-Cl-Ph | H | NMR |
| 3-178 | cyclohexylmethyl | Me | 2-thienyl | H | |
| 3-179 | cyclohexylmethyl | Me | 3-pyridyl | H | |
| 3-180 | but-3-en-1-yl | Me | Ph | H | NMR |
| 3-181 | but-3-en-1-yl | Me | 4-Cl-Ph | H | |
| 3-182 | but-3-en-1-yl | Me | 2-thienyl | H | |
| 3-183 | but-3-en-1-yl | Me | 3-pyridyl | H | |
| 3-184 | 2-chloroprop-2-en-1-yl | Me | Ph | H | NMR |
| 3-185 | 2-chloroprop-2-en-1-yl | Me | 4-Cl-Ph | H | NMR |
| 3-186 | 2-chloroprop-2-en-1-yl | Me | 2-thienyl | H | NMR |
| 3-187 | 2-chloroprop-2-en-1-yl | Me | 3-thienyl | H | NMR |
| 3-188 | 2-chloroprop-2-en-1-yl | Me | 3-Me-2-thienyl | H | NMR |
| 3-189 | 2-chloroprop-2-en-1-yl | Me | 4-Me-2-thienyl | H | NMR |
| 3-190 | 2-chloroprop-2-en-1-yl | Me | 5-Cl-2-thienyl | H | NMR |
| 3-191 | 2-chloroprop-2-en-1-yl | Me | 5-Me-2-thienyl | H | NMR |
| 3-192 | 2-chloroprop-2-en-1-yl | Me | 3-pyridyl | H | |
| 3-193 | 2-chloroprop-2-en-1-yl | Me | 6-MeO-pyridin-3-yl | H | NMR |
| 3-194 | 2-chloroprop-2-en-1-yl | Me | 6-OH-pyridin-3-yl | H | |
| 3-195 | 2-chloroprop-2-en-1-yl | Me | 6-Me-pyridin-3-yl | H | NMR |
| 3-196 | 2-chloroprop-2-en-1-yl | Me | 4-Me-Ph | H | |
| 3-197 | 2-chloroprop-2-en-1-yl | Me | 4-Br-Ph | H | |
| 3-198 | 2-chloroprop-2-en-1-yl | Me | 4-F-Ph | H | NMR |
| 3-199 | 2-chloroprop-2-en-1-yl | Me | 5-Cl-pyridin-2-yl | H | |
| 3-200 | 2-chloroprop-2-en-1-yl | Me | 5-Br-pyridin-2-yl | H | |
| 3-201 | 2-chloroprop-2-en-1-yl | Me | 5-F-pyridin-2-yl | H | |
| 3-202 | 2-chloroprop-2-en-1-yl | Me | 5-Me-pyridin-2-yl | H | |
| 3-203 | 2-chloroprop-2-en-1-yl | Me | 2-pyridyl | H | NMR |
| 3-204 | 2-chloroprop-2-en-1-yl | Me | 4-pyridyl | H | |
| 3-205 | 2-chloroprop-2-en-1-yl | Me | 4-Cl-Ph | 4-Me | |
| 3-206 | 2-chloroprop-2-en-1-yl | Me | Ph | 4-Me | |
| 3-207 | 2-chloroprop-2-en-1-yl | H | Ph | H | NMR |
| 3-208 | Et | Me | 4-Cl-Ph | H | |
| 3-209 | Et | Me | 2-thienyl | H | |
| 3-210 | Et | Me | 3-thienyl | H | |
| 3-211 | Et | Me | 3-Me-2-thienyl | H | |
| 3-212 | Et | Me | 4-Me-2-thienyl | H | |
| 3-213 | Et | Me | 5-Cl-2-thienyl | H | |
| 3-214 | Et | Me | 5-Me-2-thienyl | H | |
| 3-215 | Et | Me | 3-pyridyl | H | |
| 3-216 | Et | Me | 6-MeO-pyridin-3-yl | H | |
| 3-217 | Et | Me | 6-OH-pyridin-3-yl | H | |
| 3-218 | Et | Me | 6-Me-pyridin-3-yl | H | |
| 3-219 | Et | Me | 4-Me-Ph | H | |
| 3-220 | Et | Me | 4-Br-Ph | H | |
| 3-221 | Et | Me | Ph | H | |
| 3-222 | Et | Me | 4-F-Ph | H | |
| 3-223 | Et | Me | 5-Cl-pyridin-2-yl | H | |
| 3-224 | Et | Me | 5-Br-pyridin-2-yl | H | |
| 3-225 | Et | Me | 5-F-pyridin-2-yl | H | |
| 3-226 | Et | Me | 5-Me-pyridin-2-yl | H | |
| 3-227 | Et | Me | 2-pyridyl | H | NMR |
| 3-228 | Et | Me | 4-pyridyl | H | |
| 3-229 | 2-methoxyethyl | Me | 4-Cl-Ph | H | NMR |
| 3-230 | tetrahydrofuran-2-yl-methyl | Me | 2-pyridyl | H | NMR |
| 3-231 | 2-(dimethylamino)ethyl | Me | 4-Cl-Ph | H | NMR |
| 3-232 | oxetan-3-yl | Me | 4-Cl-Ph | H | NMR |
| 3-233 | (3-methyloxetan-3-yl)methyl | Me | 4-Cl-Ph | H | NMR |
| 3-234 | Et | Me | 4-Me-pyridin-2-yl | 4-Me | |
| 3-235 | Et | Me | 4-Me-pyridin-2-yl | H | |

"NMR" of the exemplary compounds were in each case measured as $^1$H-NMR spectra at 300 MHz (CDCl$_3$) ($^1$H nuclear resonance data). Characteristic chemical shifts δ (ppm) for some exemplary compounds are listed below:

Ex. No.: δ (ppm)

3-1: 1.27 (t, 3 H), 2.04 (s, 3 H), 2.38 (s, 3 H), 3.41 (s, 2 H), 4.18 (q, 2 H), 7.10 (d, 2 H), 7.25 (d, 2 H)

3-34: 0.91 (t, 3 H), 1.63 (sext., 2 H), 2.38 (s, 3 H), 3.60 (s, 2 H), 4.05 (t, 2 H), 8.40 (d, 1 H), 8.48 (dd, 1 H), 8.61 (dt, 1 H)

3-36: 1.23 (d, 6 H), 2.37 (s, 3 H), 3.38 (s, 2 H), 5.03 (sept, 1 H)

TABLE 3-continued

| | |
|---|---|
| 3-48: | 1.22 (d, 6 H), 2.38 (s, 3 H), 3.55 (s, 2 H), 4.99 (sept., 1 H), 8.39 (d, 1 H), 8.48 (dd, 1 H), 8.61 (dt, 1 H) |
| 3-54: | 2.37 (s, 3 H), 2.49 (t, 1 H), 3.48 (s, 2 H), 4.72 (d, 2 H) |
| 3-55: | 2.38 (s, 3 H), 2.51 (t, 1 H), 3.44 (s, 2 H), 4.72 (d, 2 H), 7.19 (d, 2 H), 7.38 (d, 2 H) |
| 3-63: | 2.38 (s, 3 H), 2.50 (t, 1 H), 3.45 (s, 2 H), 3.95 (s, 3 H), 4.72 (d, 2 H), 6.75 (d, 1 H), 7.28 (dd, 1 H), 7.40 (dd, 1 H), 7.62 (dt, 1 H), 8.08 (d, 1 H), 8.48 (m, 2 H) |
| 3-64: | 2.49 (t, 1 H), 3.55 (s, 2 H), 4.71 (d, 2 H), 7.84 (s, 1 H), 8.48 (dd, 1 H), 8.50 (d, 1 H) |
| 3-68: | 2.38 (s, 3 H), 2.50 (t, 1 H), 3.44 (s, 2 H), 4.71 (d, 2 H), 7.07 (t, 2 H) |
| 3-73: | 2.38 (s, 3 H), 2.45 (t, 1 H), 3.64 (s, 2 H), 4.67 (d, 2 H), 7.26 (m, 3 H), 7.67 (m, 2 H), 8.40 (d, 1 H), 8.46 (dd, 1 H), 8.61 (m, 1 H) |
| 3-74: | 2.39 (s, 3 H), 2.51 (t, 1 H), 3.50 (s, 2 H), 4.73 (d, 2 H), 7.17 (d, 2 H), 8.63 (d, 2 H) |
| 3-75: | 2.05 (s, 3 H), 2.38 (s, 3 H), 2.51 (t, 1 H), 3.50 (s, 2 H), 4.73 (d, 2 H), 7.10 (d, 2 H), 7.28 (d, 2 H) |
| 3-77: | 0.28 (m, 2 H), 0.58 (m, 2 H), 1.15 (m, 1 H), 2.38 (s, 3 H), 3.42 (s, 2 H), 3.96 (d, 2 H) |
| 3-78: | 0.28 (m, 2 H), 0.59 (m, 2 H), 1.14 (m, 1 H), 2.39 (s, 3 H), 3.41 (s, 2 H), 3.97 (d, 2 H), 7.20 (d, 2 H), 7.37 (d, 2 H) |
| 3-85: | 0.29 (m, 2 H), 0.59 (m, 2 H), 1.15 (m, 1 H), 2.23 (s, 3 H), 2.37 (s, 3 H), 3.50 (s, 2 H), 3.96 (d, 2 H), 6.86 (d, 1 H), 6.98 (d, 1 H) |
| 3-86: | 0.28 (m, 2 H), 0.59 (m, 2 H), 1.14 (m, 1 H), 2.39 (s, 3 H), 2.59 (s, 3 H), 3.42 (s, 2 H), 3.96 (d, 2 H), 7.18 (d, 1 H), 7.27 (dd, 1 H), 7.48 (dd, 1 H), 7.61 (dt, 1 H), 8.39 (d, 1 H), 8.44 (d, 1 H), 8.48 (dd, 1 H) |
| 3-87: | 0.30 (m, 2 H), 0.60 (m, 2 H), 1.16 (m, 1 H), 2.38 (s, 3 H), 3.41 (s, 2 H), 3.97 (d, 2 H), 6.53 (d, 1 H), 7.21 (dd, 1 H), 7.33 (dd, 1 H), 7.58 (d, 1 H), 7.78 (dt, 1 H), 8.53 (dd, 1 H), 8.60 (d, 1 H), 13.38 (broad s, 1 H) |
| 3-91: | 0.28 (m, 2 H), 0.59 (m, 2 H), 1.14 (m, 1 H), 2.38 (s, 3 H), 3.41 (s, 2 H), 3.95 (d, 2 H), 7.07 (t, 2 H), 7.58 (dt, 1 H), 8.46 (m, 2 H) |
| 3-98: | 0.28 (m, 2 H), 0.59 (m, 2 H), 1.14 (m, 1 H), 2.04 (s, 3 H), 2.38 (s, 3 H), 3.43 (s, 2 H), 3.97 (d, 2 H), 7.14 (d, 2 H), 7.37 (d, 2 H) |
| 3-100: | 0.28 (m, 2 H), 0.58 (m, 2 H), 1.13 (m, 1 H), 3.51 (s, 2 H), 3.96 (d, 2 H), 7.83 (s, 1 H), 8.48 (dd, 1 H), 8.50 (d, 1 H) |
| 3-101: | 2.38 (s, 3 H), 3.50 (s, 2 H), 4.93 (d, 2 H) |
| 3-105: | 0.38 (m, 2 H), 0.48 (m, 2 H), 1.10 (s, 3 H), 2.40 (s, 3 H), 3.45 (s, 2 H), 3.93 (s, 2 H) |
| 3-109: | 2.39 (s, 3 H), 3.48 (s, 2 H), 4.17 (m, 2 H), 4.77 (m, 2 H) |
| 3-113: | 1.34 (t, 1 H), 1.71 (dd, 1 H), 2.00 (m, 1 H), 2.40 (s, 3 H), 3.47 (s, 2 H), 4.07 (dd, 1 H), 4.40 (dd, 1 H) |
| 3-117: | 1.86 (t, 3 H), 2.38 (s, 3 H), 3.46 (s, 2 H), 4.66 (q, 2 H) |
| 3-118: | 1.87 (t, 3 H), 2.38 (s, 3 H), 3.42 (s, 2 H), 4.68 (q, 2 H), 7.19 (d, 2 H), 7.37 (d, 2 H) |
| 3-138: | 1.87 (t, 3 H), 2.05 (s, 3 H), 2.38 (s, 3 H), 3.47 (s, 2 H), 4.68 (q, 2 H), 7.12 (d, 2 H), 7.27 (d, 2 H) |
| 3-139: | 1.87 (t, 3 H), 2.05 (s, 3 H), 2.38 (s, 3 H), 3.50 (s, 2 H), 4.70 (q, 2 H) |
| 3-140: | 1.51 (d, 3 H), 2.39 (s, 3 H), 2.47 (d, 1 H), 3.43 (s, 2 H), 5.46 (dq, 1 H) |
| 3-144: | 0.23 (m, 1 H), 0.38 (m, 1 H), 0.52 (m, 2 H), 1.30 (d, 3 H), 2.39 (s, 3 H), 3.40 (s, 2 H), 4.38 (m, 1 H) |
| 3-148: | 2.38 (s, 3 H), 3.43 (s, 2 H), 4.61 (m, 2 H), 5.25 (m, 1 H), 5.30 (m, 1 H), 5.90 (m, 1 H) |
| 3-152: | 1.72 (s, 3 H), 1.78 (s, 3 H), 2.38 (s, 3 H), 3.41 (s, 2 H), 4.60 (d, 2 H), 5.35 (t, 1 H) |
| 3-156: | 1.74 (s, 3 H), 2.39 (s, 3 H), 3.45 (s, 2 H), 4.54 (s, 2 H), 4.97 (m, 2 H) |
| 3-160: | 1.28 (d, 3 H), 1.70 (m, 3 H), 2.38 (s, 3 H), 3.40 (s, 2 H), 5.34 (quint, 1 H), 5.46 (m, 1 H), 5.71 (dq, 1 H) |
| 3-164: | 2.40 (s, 3 H), 3.45 (s, 2 H), 4.94 (s, 2 H) |
| 3-168: | 1.75 (m, 2 H), 1.87 (m, 2 H), 2.06 (m, 2 H), 2.39 (s, 3 H), 2.62 (sept, 1 H), 3.41 (s, 2 H), 4.09 (d, 2 H) |
| 3-172: | 1.22 (m, 2 H), 1.58 (m, 4 H), 1.72 (m, 2 H), 2.20 (sept, 1 H), 2.38 (s, 3 H), 3.41 (s, 2 H), 4.01 (d, 2 H) |
| 3-176: | 0.95 (m, 2 H), 1.22 (m, 3 H), 1.69 (m, 6 H), 2.39 (s, 3 H), 3.41 (s, 2 H), 3.94 (d, 2 H) |
| 3-180: | 2.05 (s, 3 H), 2.37 (s, 3 H), 2.40 (q, 2 H), 3.47 (s, 2 H), 4.20 (t, 2 H), 5.10 (m, 2 H), 5.78 (m, 1 H) |
| 3-184: | 2.39 (s, 3 H), 3.50 (s, 2 H), 4.70 (s, 2 H), 5.40 (m, 2 H) |
| 3-185: | 2.38 (s, 3 H), 3.48 (s, 2 H), 4.70 (s, 2 H), 5.42 (s, 2 H), 7.18 (d, 2 H), 7.36 (d, 2 H) |
| 3-186: | 2.38 (s, 3 H), 3.58 (s, 2 H), 4.70 (s, 2 H), 5.41 (m, 2 H), 7.03 (m, 1 H), 7.07 (m, 1 H), 7.29 (dd, 1 H), 7.42 (d, 1 H), 7.66 (dt, 1 H), 8.50 (dd, 1 H), 8.55 (d, 1 H) |
| 3-187: | 2.38 (s, 3 H), 3.51 (s, 2 H), 4.70 (s, 2 H), 5.42 (m, 2 H), 6.80 (dd, 1 H), 7.28 (dd, 1 H), 7.34 (dd, 1 H), 7.42 (dd, 1 H), 7.61 (dt, 1 H), 8.48 (dd, 1 H), 8.51 (d, 1 H) |
| 3-188: | 1.84 (s, 3 H), 2.37 (s, 3 H), 3.49 (broad d, 2 H), 3.68 (s, 3 H), 3.57 (s, 2 H), 4.64 (s, 2 H), 5.39 (s, 2 H), 6.87 (d, 1 H), 7.23 (dd, 1 H), 7.38 (d, 1 H), 7.61 (dt, 1 H), 8.43 (dd, 1 H), 8.52 (d, 1 H) |

TABLE 3-continued 3-189: 2.25 (s, 3 H), 2.37 (s, 3 H), 3.57 (s, 2 H), 4.70 (s, 2 H), 5.42 (m, 2 H), 6.84 (s, 1 H), 6.99 (s, 1 H), 7.29 (dd, 1 H), 7.69 (dt, 1 H), 8.50 (dd, 1 H), 8.56 (d, 1 H)
3-190: 2.37 (s, 3 H), 3.55 (s, 2 H), 4.70 (s, 2 H), 5.42 (m, 2 H), 6.83 (d, 1 H), 6.89 (d, 1 H), 7.31 (dd, 1 H), 7.69 (dt, 1 H), 8.54 (dd, 1 H), 8.59 (d, 1 H)
3-191: 2.36 (s, 3 H), 2.45 (s, 3 H), 3.56 (s, 2 H), 4.70 (s, 2 H), 5.42 (m, 2 H), 6.70 (d, 1 H), 6.80 (d, 1 H), 7.29 (dd, 1 H), 7.70 (dt, 1 H), 8.49 (dd, 1 H), 8.56 (d, 1 H)
3-193: 2.38 (s, 3 H), 3.48 (s, 2 H), 3.96 (s, 3 H), 4.70 (s, 2 H), 5.42 (m, 2 H), 6.75 (d, 1 H), 7.28 (dd, 1 H), 7.41 (dd, 1 H), 7.62 (dt, 1 H), 8.08 (d, 1 H), 8.48 (m, 2 H)
3-195: 2.39 (s, 3 H), 2.59 (s, 3 H), 3.48 (s, 2 H), 4.70 (s, 2 H), 5.42 (m, 2 H), 7.18 (d, 1 H), 7.27 (dd, 1 H), 7.46 (dd, 1 H), 7.62 (dt, 1 H), 8.39 (d, 1 H), 8.44 (d, 1 H), 8.48 (dd, 1 H)
3-198: 2.38 (s, 3 H), 3.47 (s, 2 H), 4.70 (s, 2 H), 5.42 (m, 2 H), 7.07 (t, 2 H)
3-203: 2.39 (s, 3 H), 3.68 (s, 2 H), 4.66 (s, 2 H), 5.40 (m, 2 H), 7.26 (m, 3 H), 7.69 (m, 2 H), 8.40 (d, 1 H), 8.47 (dd, 1 H), 8.62 (m, 1 H)
3-207: 3.58 (s, 2 H), 4.68 (s, 2 H), 5.41 (m, 2 H), 7.84 (s, 1 H), 8.47 (dd, 1 H), 8.50 (d, 1 H)
3-227: 1.25 (t, 3 H), 2.38 (s, 3 H), 3.59 (s, 2 H), 4.15 (q, 2 H), 8.40 (d, 1 H), 8.48 (dd, 1 H), 8.61 (dt, 1 H)
3-229: 2.37 (s, 3 H), 3.39 (s, 3 H), 3.45 (s, 2 H), 3.59 (m, 2 H), 4.28 (m, 2 H), 7.20 (d, 2 H), 7.35 (d, 2 H)
3-230: 1.83-2.05 (m, 4 H), 2.38 (s, 3 H), 3.66 (s, 2 H), 3.75-3.90 (m, 2 H), 4.05 (dd, 1 H), 4.10 (m, 1 H), 4.18 (dd, 1 H), 8.40 (d, 1 H), 8.49 (dd, 1 H), 8.62 (dt, 1 H)
3-231: 2.28 (s, 6 H), 2.37 (s, 3 H), 2.56 (t, 2 H), 3.43 (s, 2 H), 4.22 (t, 2 H), 7.19 (d, 2 H), 7.35 (d, 2 H)
3-232: 2.38 (s, 3 H), 3.47 (s, 2 H), 3.58 (m, 2 H), 4.07 (m, 1 H), 4.38 (m, 2 H), 7.17 (d, 2 H), 7.37 (d, 2 H)
3-233: 0.99 (s, 3 H), 2.38 (s, 3 H), 3.45 (m, overlapping signals, 6 H), 4.12 (m, 2 H), 7.17 (d, 2 H), 7.37 (d, 2 H)

TABLE 4

Compounds of the formula (III) (intermediates)

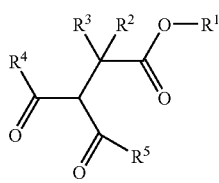

(III)

| No. | $R^1$ | $R^2$ | $R^3$ | $R^4$ | $R^5$ | Data |
|---|---|---|---|---|---|---|
| 4-1 | Me | H | H | Ph | Ph | |
| 4-2 | Me | H | H | Me | Ph | |
| 4-3 | Me | H | H | Me | 2-furyl | |
| 4-4 | Me | Me | H | Me | Ph | |
| 4-5 | Me | H | H | Me | 4-MeO-Ph | |
| 4-6 | Me | H | H | Me | 4-Me-Ph | |
| 4-7 | Me | H | H | Me | 3-$CF_3$-Ph | |
| 4-8 | Me | H | H | Me | 3,4-$Cl_2$-Ph | |
| 4-9 | Me | H | H | Me | 3-Cl-Ph | |
| 4-10 | Me | H | H | Me | 2-Cl-Ph | |
| 4-11 | Me | H | H | Me | 2,4-$Cl_2$-Ph | |
| 4-12 | Me | H | H | Me | 4-$CF_3$-Ph | |
| 4-13 | Me | H | H | Me | 4-Cl-Ph | |
| 4-14 | Me | H | H | Me | 4-$CF_3$-Ph | |
| 4-15 | Me | H | H | Me | 4-tBu-Ph | |
| 4-16 | Me | H | H | Me | 3,5-$Me_2$-Ph | |
| 4-17 | Me | H | H | Me | 4-Me-Ph | |
| 4-18 | Me | H | H | Me | 4-F-Ph | |
| 4-19 | Me | H | H | Me | 3-Me-Ph | |
| 4-20 | Me | H | H | Me | 4-COOH-Ph | |
| 4-21 | Me | H | H | Me | 3-Br-Ph | |
| 4-22 | Me | H | H | Me | 4-Ph-Ph | |
| 4-23 | Me | H | H | Me | 3-Cl-4-Me-Ph | |
| 4-24 | Me | H | H | Me | 3-$CF_3$-4-chloro-Ph | |
| 4-25 | Me | H | H | Me | 2-thienyl | |
| 4-26 | Me | H | H | Me | 3-Me-2-thienyl | |
| 4-27 | Me | H | H | Me | 4-Me-2-thienyl | |
| 4-28 | Me | H | H | Me | 5-Cl-2-thienyl | |
| 4-29 | Me | H | H | Me | 3-thienyl | |
| 4-30 | Me | H | H | Me | 5-Me-2-thienyl | |
| 4-31 | Me | H | H | Me | 6-MeO-pyridin-3-yl | |
| 4-32 | Me | H | H | Me | 3-thienyl | |
| 4-33 | Me | H | H | Me | 4-Br-Ph | |
| 4-34 | Me | H | H | Me | 1,3-benzodioxol-5-yl | |
| 4-35 | Me | H | H | Me | 4-I-Ph | |
| 4-36 | Me | H | H | Me | 4-PhO-Ph | |
| 4-37 | Me | H | H | Me | 6-OH-pyridin-3-yl | |
| 4-38 | Me | H | H | H | Ph | |
| 4-39 | Me | H | H | Et | Ph | |
| 4-40 | Me | H | H | n-Pr | Ph | |
| 4-41 | Me | H | H | $CH_2Cl$ | Ph | |
| 4-42 | Me | H | H | $CHCl_2$ | Ph | |
| 4-43 | Me | H | H | $CH_2F$ | Ph | |
| 4-44 | Me | H | H | $CHF_2$ | Ph | |
| 4-45 | Me | H | H | Cl | Ph | |
| 4-46 | Me | H | H | n-Pr | 4-Cl-Ph | |
| 4-47 | Me | H | H | $CH_2Cl$ | 4-Cl-Ph | |
| 4-48 | Me | H | H | $CHCl_2$ | 4-Cl-Ph | |
| 4-49 | Me | H | H | $CH_2F$ | 4-Cl-Ph | |
| 4-50 | Me | H | H | $CHF_2$ | 4-Cl-Ph | |
| 4-51 | Me | H | H | Cl | 4-Cl-Ph | |
| 4-52 | Me | H | H | Et | 4-Me-Ph | |
| 4-53 | Me | H | H | n-Pr | 4-Me-Ph | |
| 4-54 | Me | H | H | $CH_2Cl$ | 4-Me-Ph | |
| 4-55 | Me | H | H | $CHCl_2$ | 4-Me-Ph | |
| 4-56 | Me | H | H | $CH_2F$ | 4-Me-Ph | |
| 4-57 | Me | H | H | $CHF_2$ | 4-Me-Ph | |
| 4-58 | Me | H | H | Cl | 4-Me-Ph | |

TABLE 4-continued

Compounds of the formula (III) (intermediates)

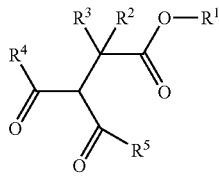

(III)

| No. | $R^1$ | $R^2$ | $R^3$ | $R^4$ | $R^5$ | Data |
|---|---|---|---|---|---|---|
| 4-59 | Me | H | H | Et | 2-pyridyl | |
| 4-60 | Me | H | H | n-Pr | 2-pyridyl | |
| 4-61 | Me | H | H | $CH_2Cl$ | 2-pyridyl | |
| 4-62 | Me | H | H | $CHCl_2$ | 2-pyridyl | |
| 4-63 | Me | H | H | $CH_2F$ | 2-pyridyl | |
| 4-64 | Me | H | H | $CHF_2$ | 2-pyridyl | |
| 4-65 | Me | H | H | Cl | 2-pyridyl | |
| 4-66 | Me | H | H | Me | 2-pyridyl | |
| 4-67 | Me | H | H | Me | 5-Cl-pyridin-2-yl | |
| 4-68 | Me | H | H | Me | 5-Br-pyridin-2-yl | |
| 4-69 | Me | H | H | Me | 5-F-pyridin-2-yl | |
| 4-70 | Me | H | H | Me | 5-Me-pyridin-2-yl | |
| 4-71 | Me | H | H | Me | 2,4-$Cl_2$-Ph | |
| 4-72 | Me | H | H | Me | 4-$CH_2$COOH-Ph | |
| 4-73 | Me | H | H | Me | 4-Me(CO)-Ph | |
| 4-74 | Me | H | H | Me | 4-tBu-Ph | |
| 4-75 | Me | H | H | Me | 4-Cl-3-Me-Ph | |
| 4-76 | Me | H | H | n-Pr | 4-Cl-Ph | |
| 4-77 | Me | H | H | Me | 3-pyridyl | |
| 4-78 | Me | H | H | Me | 4-pyridyl | |
| 4-79 | Me | H | H | C(O)OMe | Ph | |
| 4-80 | Me | H | H | Me | 6-Me-pyridin-3-yl | |
| 4-81 | Me | H | H | Me | 2,3-dichloro-Ph | |
| 4-82 | Me | H | H | H | 4-Cl-Ph | |
| 4-83 | Me | H | H | Me | 6-Cl-pyridin-3-yl | |
| 4-84 | Et | H | H | Ph | Ph | |
| 4-85 | Et | H | H | Me | Ph | |
| 4-86 | Et | Me | H | Me | Ph | |
| 4-87 | Et | H | H | Me | 4-MeO-Ph | |
| 4-88 | Et | H | H | Me | 4-Me-Ph | |
| 4-89 | Et | H | H | Me | 3-$CF_3$-Ph | |
| 4-90 | Et | H | H | Me | 3,4-$Cl_2$-Ph | |
| 4-91 | Et | H | H | Me | 3-Cl-Ph | |
| 4-92 | Et | H | H | Me | 2-Cl-Ph | |
| 4-93 | Et | H | H | Me | 2,4-$Cl_2$-Ph | |
| 4-94 | Et | H | H | Me | 4-$CF_3$-Ph | |
| 4-95 | Et | H | H | Me | 4-Cl-Ph | |
| 4-96 | Et | H | H | Me | 4-$CF_3$-Ph | |
| 4-97 | Et | H | H | Me | 4-tBu-Ph | |
| 4-98 | Et | H | H | Me | 3,5-$Me_2$-Ph | |
| 4-99 | Et | H | H | Me | 4-Me-Ph | |
| 4-100 | Et | H | H | Me | 4-F-Ph | |
| 4-101 | Et | H | H | Me | 3-Me-Ph | |
| 4-102 | Et | H | H | Me | 4-COOH-Ph | |
| 4-103 | Et | H | H | Me | 3-Br-Ph | |
| 4-104 | Et | H | H | Me | 4-Ph-Ph | |
| 4-105 | Et | H | H | Me | 3-Cl-4-Me-Ph | |
| 4-106 | Et | H | H | Me | 3-$CF_3$-4-chloro-Ph | |
| 4-107 | Et | H | H | Me | 2-thienyl | |
| 4-108 | Et | H | H | Me | 3-Me-2-thienyl | |
| 4-109 | Et | H | H | Me | 4-Me-2-thienyl | |
| 4-110 | Et | H | H | Me | 5-Cl-2-thienyl | |
| 4-111 | Et | H | H | Me | 3-thienyl | |
| 4-112 | Et | H | H | Me | 5-Me-2-thienyl | |
| 4-113 | Et | H | H | Me | 6-MeO-pyridin-3-yl | |
| 4-114 | Et | H | H | Me | 3-thienyl | |
| 4-115 | Et | H | H | Me | 4-Br-Ph | |
| 4-116 | Et | H | H | Me | 1,3-benzodioxol-5-yl | |
| 4-117 | Et | H | H | Me | 4-I-Ph | |
| 4-118 | Et | H | H | Me | 4-PhO-Ph | |
| 4-119 | Et | H | H | Me | 6-OH-pyridin-3-yl | |
| 4-120 | Et | H | H | H | Ph | |
| 4-121 | Et | H | H | Et | Ph | |
| 4-122 | Et | H | H | n-Pr | Ph | |
| 4-123 | Et | H | H | $CH_2Cl$ | Ph | |
| 4-124 | Et | H | H | $CHCl_2$ | Ph | |
| 4-125 | Et | H | H | $CH_2F$ | Ph | |
| 4-126 | Et | H | H | $CHF_2$ | Ph | |
| 4-127 | Et | H | H | Cl | Ph | |
| 4-128 | Et | H | H | n-Pr | 4-Cl-Ph | |
| 4-129 | Et | H | H | $CH_2Cl$ | 4-Cl-Ph | |
| 4-130 | Et | H | H | $CHCl_2$ | 4-Cl-Ph | |
| 4-131 | Et | H | H | $CH_2F$ | 4-Cl-Ph | |
| 4-132 | Et | H | H | $CHF_2$ | 4-Cl-Ph | |
| 4-133 | Et | H | H | Cl | 4-Cl-Ph | |
| 4-134 | Et | H | H | Et | 4-Me-Ph | |
| 4-135 | Et | H | H | n-Pr | 4-Me-Ph | |
| 4-136 | Et | H | H | $CH_2Cl$ | 4-Me-Ph | |
| 4-137 | Et | H | H | $CHCl_2$ | 4-Me-Ph | |
| 4-138 | Et | H | H | $CH_2F$ | 4-Me-Ph | |
| 4-139 | Et | H | H | $CHF_2$ | 4-Me-Ph | |
| 4-140 | Et | H | H | Cl | 4-Me-Ph | |
| 4-141 | Et | H | H | Et | 2-pyridyl | |
| 4-142 | Et | H | H | n-Pr | 2-pyridyl | |
| 4-143 | Et | H | H | $CH_2Cl$ | 2-pyridyl | |
| 4-144 | Et | H | H | $CHCl_2$ | 2-pyridyl | |
| 4-145 | Et | H | H | $CH_2F$ | 2-pyridyl | |
| 4-146 | Et | H | H | $CHF_2$ | 2-pyridyl | |
| 4-147 | Et | H | H | Cl | 2-pyridyl | |
| 4-148 | Et | H | H | Me | 2-pyridyl | |
| 4-149 | Et | H | H | Me | 5-Cl-pyridin-2-yl | |
| 4-150 | Et | H | H | Me | 5-Br-pyridin-2-yl | |
| 4-151 | Et | H | H | Me | 5-F-pyridin-2-yl | |
| 4-152 | Et | H | H | Me | 5-Me-pyridin-2-yl | |
| 4-153 | Et | H | H | Me | 2,4-$Cl_2$-Ph | |
| 4-154 | Et | H | H | Me | 4-$CH_2$COOH-Ph | |
| 4-155 | Et | H | H | Me | 4-Me(CO)-Ph | |
| 4-156 | Et | H | H | Me | 4-tBu-Ph | |
| 4-157 | Et | H | H | Me | 4-Cl-3-Me-Ph | |
| 4-158 | Et | H | H | n-Pr | 4-Cl-Ph | |
| 4-159 | Et | H | H | Me | 3-pyridyl | |
| 4-160 | Et | H | H | Me | 4-pyridyl | |
| 4-161 | Et | H | H | C(O)OMe | Ph | |
| 4-162 | Et | H | H | Me | 6-Me-pyridin-3-yl | |
| 4-163 | Et | H | H | Me | 2,3-dichloro-Ph | |
| 4-164 | Et | H | H | H | 4-Cl-Ph | |
| 4-165 | Et | H | H | Me | 6-Cl-pyridin-3-yl | |

(B) FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A readily water-dispersible dispersion concentrate is obtained by mixing 20 parts by weight of a compound of the formula (I) with 6 parts by weight of alkylphenol Polyglycol Ether®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Water-dispersible granules are obtained by mixing

| | | |
|---|---|---|
| 75 | parts by weight | of a compound of the formula (I), |
| 10 | " | of calcium lignosulfonate, |
| 5 | " | of sodium lauryl sulfate, |
| 3 | " | of polyvinyl alcohol and |
| 7 | " | of kaolin, | grinding the mixture in a pinned-disk mill, and granulating the powder in a fluidized bed by spraying on water as granulating liquid.

f) Water-dispersible granules are also obtained by homogenizing and precomminuting

| | | |
|---|---|---|
| 25 | parts by weight | of a compound of the formula (I), |
| 5 | " | of sodium 2,2'-dinaphthylmethane-6,6'-disulfonate, |
| 2 | " | sodium oleoylmethyltaurate, |
| 1 | part by weight | of polyvinyl alcohol, |
| 17 | parts by weight | of calcium carbonate and |
| 50 | " | of water | in a collid mill, then grinding the mixture in a bead mill, and atomizing and drying the resulting suspension in a spray tower, using a single-fluid nozzle.

(C) BIOLOGICAL EXAMPLES

1. Pre-Emergence Effect on Weeds

Seeds or sections of rhizome from monocotyledonous and dicotyledonous weed plants were laid out in sandy loam soil in plastic pots, and covered with soil. The compounds according to the invention, formulated as wettable powders or emulsifiable concentrates, were then applied, in the form of aqueous suspensions or emulsions, at various dosages, onto the surface of the covering soil, at an application rate of 600 to 800 l of water/ha (converted).

Following the treatment, the pots were placed in a greenhouse and maintained under good growth conditions for the weeds. Visual scoring of the plant damage or emergence damage was made when the test plants had emerged, after a test time of 3 to 4 weeks, in comparison to untreated controls. As the test results showed, the compounds according to the invention featured good pre-emergence herbicidal activity against a broad spectrum of weed grasses and broad-leaved weeds. For example, the Examples Nos. 1-1, 1-2, 1-4, 1-5, 1-7, 1-8, 1-9, 1-10, 1-11, 1-12, 1-13, 1-14, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 140, 141, 1-42, 1-43, 1-45, 146, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-70, 1-71, 1-72, 1-73, 1-109, 1-110, 1-113, 1-120, 1-125, 1-135, 1-136, 1-137, 1-144, 1-145, 1-146, 2-1, 2-2, 2-4, 2-5, 2-6, 2-7, 2-8, 2-9, 2-10, 2-11, 2-12, 2-13, 2-14, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-35, 2-36, 2-37, 2-38, 240, 2-41, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-66, 2-68, 2-70, 2-71, 2-72, 2-73, 2-74, 2-79, 2-89, 2-109, 2-110, 2-113, 2-114, 2-115, 2-116, 2-119, 2-120, 2-121, 2-122, 2-123, 2-124, 2-125, 2-126, 2-127, 2-128, 2-131, 2-132, 2-133, 2-134, 2-135, 2-136, 2-144, 2-145, 2-146, 2-147, 2-165, 2-184, 13-1, 3-34, 3-36, 3-48, 3-50, 3-54, 3-55, 3-63, 3-64, 3-68, 3-73, 3-74, 3-75, 3-76, 3-77, 3-78, 3-85, 3-86, 3-87, 3-91, 3-98, 3-99, 3-100, 3-101, 3-105, 3-109, 3-113, 3-117, 3-118, 3-136, 3-139, 3-140, 3-144, 3-148, 3-152, 3-156, 3-160, 3-164, 3-168, 3-172, 3-177, 3-180, 3-184, 3-186, 3-187, 3-188, 3-189, 3-190, 3-191, 3-193, 3-195, 3-198, 3-203, 3-207, 3-227, 3-229, 3-230, 3-231, 3-232, 3-233 from Tables 1 to 3 showed very good herbicidal action (control of 70% or more) against weed plants such as *Lolium multiflorum, Amaranthus retroflexus, Sinapis alba, Stellaria media* and *Setaria viridis* when applied by the pre-emergence method at an application rate of 1 kg or less of active substance per hectare. Here, some of the exemplary compounds also showed very good action against harmful plants such as *Avena sativa* and *Capsella* bursa-pastoris.

2. Post-Emergence Effect on Weeds

Seeds or sections of rhizome from monocotyledonous and dicotyledonous weeds were laid out in sandy loam soil in plastic pots, covered with soil, and cultivated in a greenhouse under good growth conditions. Three weeks after sowing, the test plants were treated at the three-leaf stage. The compounds according to the invention, formulated as wettable powders or as emulsion concentrates, were sprayed in different dosages onto the green parts of the plants, at an application rate of 600 to 800 l of water/ha (converted). After the test plants had stood in the greenhouse under optimum growth conditions for a period of about 3 to 4 weeks, the effect of the products was scored visually in comparison to untreated controls. Post-emergence as well, the compositions according to the invention exhibited good herbicidal activity against a broad spectrum of economically important weed grasses and broad-leaved weeds. For example, the Examples Nos. 1-1, 1-2, 14, 1-5, 1-7, 1-8, 1-9, 1-10, 1-11, 1-12, 1-13, 1-14, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 140, 1-41, 1-42, 1-43, 1-45, 1-46, 1-47, 148, 1-49, 1-50, 1-51, 1-52, 1-53, 1-54, 1-55, 1-56, 1-57, 1-58, 1-59, 1-60, 1-61, 1-62, 1-63, 1-64, 1-70, 1-71, 1-72, 1-73, 1-109, 1-110, 1-113, 1-120, 1-125, 1-135, 1-136, 1-137, 1-144, 1-145, 1-146, 2-1, 2-2, 2-4, 2-5, 2-6, 2-7, 2-8, 2-9, 2-10, 2-11, 2-12, 2-13, 2-14, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-35, 2-36, 2-37, 2-38, 2-40, 241, 2-43, 2-44, 2-45, 2-46, 2-47, 248, 249, 2-50, 2-51, 2-52, 2-53, 2-54, 2-55, 2-56, 2-57, 2-58, 2-59, 2-60, 2-61, 2-62, 2-63, 2-64, 2-66, 2-68, 2-70, 2-71, 2-72, 2-73, 2-74, 2-79, 2-89, 2-109, 2-110, 2-113, 2-114, 2-115, 2-116, 2-119, 2-120, 2-121, 2-122, 2-123, 2-124, 2-125, 2-126, 2-127, 2-128, 2-131, 2-132, 2-133, 2-134, 2-135, 2-135, 2-144, 2-145, 2-146, 2-147, 2-165, 2-184, 3-1, 3-4, 3-36, 348, 3-50, 3-54, 3-55, 3-63, 3-64, 3-68, 3-73, 3-74, 3-75, 3-76, 3-77, 3-78, 3-85, 3-86, 3-87, 3-91, 3-98, 3-99, 3-100, 3-101, 3-105, 3-109, 3-113, 3-117, 3-118, 3-136, 3-139, 3-140, 3-144, 3-148, 3-152, 3-156, 3-160, 3-164, 3-168, 3-172, 3-177, 3-180, 3-184, 3-186, 3-187, 3-188, 3-189, 3-190, 3-191, 3-193, 3-195, 3-198, 3-203, 3-207, 3-227, 3-229, 3-230, 3-231, 3-232, 3-233 from Tables 1 to 3 showed very good herbicidal action (control of 70% or more) against weed plants such as *Lolium multiflorum, Amaranthus retroflexus, Sinapis alba,*

*Stellaria media* and *Setaria viridis* when applied post-emergence at an application rate of 500 g or less of active substance per hectare. Here, in some cases the exemplary compounds also showed very good action against harmful plants such as *Avena sativa* and *Capsella* bursa-pastoris.

3. Action on Weeds in Rice

Transplanted and sown rice and typical rice weeds (broad-leaved and graminaceous) were grown in closed plastic pots in the greenhouse to the three-leaf stage (*Echinochloa crus-galli* 1,5-leaf) under paddy rice conditions (depth of the water: 2 to 3 cm). This was followed by treatment with the compounds according to the invention. For this purpose, the formulated active compounds were suspended, dissolved or emulsified in water and applied by pouring them into the water around the test plants in various dosages.

After this treatment, the test plants were placed in a greenhouse under optimum growth conditions and were maintained under these conditions throughout the entire test period.

About three weeks after the application, evaluation was carried out by visual scoring of the damage to the plants by comparison with untreated controls. For example, the compounds according to the invention Nos. 1-1, 1-2, 1-4, 1-5, 1-7, 1-8, 1-9, 1-10, 1-11, 1-12, 1-13, 1-14, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-70, 1-71, 1-72, 1-73, 1-109, 1-110, 1-113, 1-120, 1-125, 1-135, 1-136, 1-137, 1-144, 1-145, 1-146, 2-1, 2-2, 24, 2-5, 2-6, 2-7, 2-8, 2-9, 2-10, 2-11, 2-12, 2-13, 2-14, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-35, 2-36, 2-37, 2-38, 2-40, 2-41, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-66, 2-68, 2-70, 2-71, 2-72, 2-73, 2-74, 2-79, 2-89, 2-109, 2-110, 2-113, 2-114, 2-115, 2-116, 2-119, 2-120, 2-121, 2-122, 2-123, 2-124, 2-125, 2-126, 2-127, 2-128, 2-131, 2-132, 2-133, 2-134, 2-135, 2-136, 2-144, 2-145, 2-146, 2-147, 2-165, 2-184, 3-1, 3-34, 3-36, 3-48, 3-50, 3-54, 3-55, 3-63, 3-64, 3-68, 3-73, 3-74, 3-75, 3-76, 3-77, 3-78, 3-85, 3-86, 3-87, 3-91, 3-98, 3-99, 3-100, 3-101, 3-105, 3-109, 3-113, 3-117, 3-118, 3-136, 3-139, 3-140, 3-144, 3-148, 3-152, 3-156, 3-160, 3-164, 3-168, 3-172, 3-177, 3-180, 3-184, 3-186, 3-187, 3-188, 3-189, 3-190, 3-191, 3-193, 3-195, 3-198, 3-203, 3-207, 3-227, 3-229, 3-230, 3-231, 3-232, 3-233 from Tables 1 to 3 showed very good herbicidal action (control of 70% or more) against typical harmful plants in rice, such as, for example, *Cyperus iria* and *Echinochloa crus-galli*.

4. Tolerance by Crop Plants

In further greenhouse experiments, seeds of a relatively large number of crop plants and weeds were placed in sandy loam soil and covered with soil. Some of the pots were treated immediately as described under section 1, while the remainder was placed in the greenhouse until the plants had developed two to three true leaves, and then sprayed with various dosages of the compounds of the formula (I) according to the invention, as described in section 2. Four to five weeks after the application, and after the plants have remained in the greenhouse, visual scoring showed that the compounds according to the invention left dicotyledonous crops such as, for example, soybeans, cotton, oilseed rape, sugar beet and potatoes undamaged when employed pre- and post-emergence, even when high dosages of active compounds were used. In general, at appropriate application rates, the compounds also spared graminaceous crops, such as, for example, barley, wheat, rye, sorghum, corn or rice. Some of the compounds of the formula (I) displayed high selectivity and are therefore suitable for controlling unwanted vegetation in agricultural crops.

5. Plant Growth Regulation Test

Culm Stabilization of Crop Plants

With stirring, the compound of the formula (I) in question was, in the form of a water-dispersible powder, together with a surfactant (customary adjuvant at an application rate of 1 l/ha), mixed with water such that a homogenous spray liquor was formed, and applied at an application rate of 300 l of water/ha (converted).

Seeds of summer wheat of the cultivar 'Triso' were sown at a depth of 1 cm in plant pots and cultivated outdoors until treatment.

The plants were treated on a laboratory track sprayer with spray liquors of the test substances at macrostage 3 after having reached about 10% of the maximum longitudinal growth typical for the cultivar (stage BBCH 31) and, after the treatment, returned outdoors.

After the ears had formed, the length of the culms were measured. The culm stabilization was evaluated as a percentage of the untreated control.

The evaluations showed that, for example, the compounds (I) according to the invention Nos. 1-1, 1-2, 1-4, 1-5, 1-7, 1-8, 1-9, 1-10, 1-11, 1-12, 1-13, 1-14, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 141, 142, 143, 145, 146, 147, 148, 149, 1-50, 1-51, 1-52, 1-53, 1-54, 1-55, 1-56, 1-57, 1-58, 1-59, 1-60, 1-61, 1-62, 1-63, 1-64, 1-70, 1-71, 1-72, 1-73, 1-109, 1-110, 1-113, 1-120, 1-125, 1-135, 1-136, 1-137, 1-144, 1-145, 1-146, 2-1, 2-2, 2-4, 2-5, 2-6, 2-7, 2-8, 2-9, 2-10, 2-11, 2-12, 2-13, 2-14, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-35, 2-36, 2-37, 2-38, 2-40, 2-41, 2-43, 244, 245, 246, 2-47, 248, 2-49, 2-50, 2-51, 2-52, 2-53, 2-54, 2-55, 2-56, 2-57, 2-58, 2-59, 2-60, 2-61, 2-62, 2-63, 2-64, 2-66, 2-68, 2-70, 2-71, 2-72, 2-73, 2-74, 2-79, 2-89, 2-109, 2-110, 2-113, 2-114, 2-115, 2-116, 2-119, 2-120, 2-121, 2-122, 2-123, 2-124, 2-125, 2-126, 2-127, 2-128, 2-131, 1-132, 2-133, 2-134, 2-135, 2-136, 2-144, 2-145, 2-146, 2-147, 2-165, 2-184, 3-1, 3-34, 3-36, 348, 3-50, 3-54, 3-55, 3-63, 3-64, 3-68, 3-73, 3-74, 3-75, 3-76, 3-77, 3-78, 3-85, 3-86, 3-87, 3-91, 3-98, 3-99, 3-100, 3-101, 3-105, 3-109, 3-113, 3-117, 3-118, 3-136, 3-139, 3-140, 3-144, 3-148, 3-152, 3-156, 3-160, 3-164, 3-168, 3-172, 3-177, 3-180, 3-184, 3-186, 3-187, 3-188, 3-189, 3-190, 3-191, 3-193, 3-195, 3-198, 3-203, 3-207, 3-227, 3-229, 3-230, 3-231, 3-232, 3-233 from Tables 1 to 3, at an application rate of 30 to 300 g of active substance per hectare, had effectively shortened the longitudinal growth of summer wheat.

The invention claimed is:
1. A method for controlling harmful plants or for regulating the growth of plants which comprises applying an effective amount of one or more compounds of the formula (I) or salts thereof

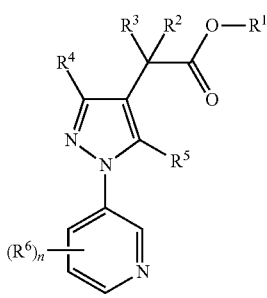

(I)

wherein
R¹ is hydrogen or a hydrolyzable radical,
R² is hydrogen, halogen or (C₁-C₆)-alkyl which is unsubstituted or substituted by one or more radicals selected from the group consisting of halogen, (C₁-C₄)-alkoxy, (C₁-C₄)-alkylthio and (C₁-C₄)-haloalkoxy,
R³ is hydrogen, halogen or (C₁-C₆)-alkyl which is unsubstituted or substituted by one or more radicals selected from the group consisting of halogen, (C₁-C₄)-alkoxy, (C₁-C₄)-alkylthio and (C₁-C₄)-haloalkoxy, or R² and R³ together with the carbon atom to which they are attached are a carbocyclic saturated or partially unsaturated ring having 3 to 6 carbon atoms which is unsubstituted or substituted by one or more radicals selected from the group consisting of halogen and (C₁-C₄)-alkyl,
R⁴ is hydrogen, halogen, cyano, (C₁-C₆)-alkyl, (C₂-C₆)-alkenyl or (C₂-C₆)-alkynyl, where each of the three last mentioned radicals is unsubstituted or substituted by one or more radicals selected from the group consisting of halogen, cyano, hydroxyl, (C₁-C₄)-alkoxy, (C₁-C₄)-haloalkoxy, (C₁-C₄)-alkoxy-(C₁-C₄)-alkoxy, (C₁-C₄)-alkylthio and optionally halogen-, cyano-, (C₁-C₄)-alkyl- or (C₁-C₄)-haloalkyl-substituted (C₃-C₉)-cycloalkyl, or (C₃-C₉)-cycloalkyl, (C₅-C₉)-cycloalkenyl or (C₅-C₉)-cycloalkynyl, where each of the 3 last mentioned radicals is unsubstituted or substituted by one or more radicals selected from the group consisting of halogen, (C₁-C₄)-alkyl, (C₁-C₄)-haloalkyl, (C₂-C₄)-alkenyl, (C₂-C₄)-alkynyl, (C₁-C₄)-alkoxy, (C₁-C₄)-haloalkoxy and (C₁-C₄)-alkylthio, or phenyl which is unsubstituted or substituted by one or more radicals selected from the group consisting of halogen, cyano, nitro, carboxyl, (C₁-C₄)-alkyl, (C₁-C₄)-haloalkyl, (C₂-C₄)-alkenyl, (C₂-C₄)-alkynyl, (C₁-C₄)-alkoxy, (C₁-C₄)-haloalkoxy, (C₁-C₄)-alkoxy-(C₁-C₄)-alkoxy, (C₁-C₄)-alkylthio, (C₁-C₄)-alkanoyl, (C₁-C₄)-haloalkanoyl, [(C₁-C₄)-alkoxy]carbonyl and [(C₁-C₄)-haloalkoxy]carbonyl, or (C₁-C₆)-alkanoyl which is unsubstituted or substituted by one or more radicals selected from the group consisting of halogen, cyano, (C₁-C₄)-alkoxy, (C₁-C₄)-haloalkoxy, (C₁-C₄)-alkoxy-(C₁-C₄)-alkoxy, (C₁-C₄)-alkylthio and optionally halogen-, cyano-, (C₁-C₄)-alkyl- or (C₁-C₄)-haloalkyl-substituted (C₃-C₆)-cycloalkyl, or [(C₁-C₄)-alkoxy]carbonyl which is unsubstituted or substituted by one or more radicals selected from the group consisting of halogen, cyano, (C₁-C₄)-alkoxy, (C₁-C₄)-haloalkoxy, (C₁-C₄)-alkoxy-(C₁-C₄)-alkoxy, (C₁-C₄)-alkylthio and optionally halogen-, cyano-, (C₁-C₄)-alkyl- or (C₁-C₄)-haloalkyl-substituted (C₃-C₆)-cycloalkyl, or [(C₃-C₉)-cycloalkoxy]carbonyl which is unsubstituted or substituted by one or more radicals selected from the group consisting of halogen, (C₁-C₄)-alkyl, (C₁-C₄)-haloalkyl, (C₂-C₄)-alkenyl, (C₂-C₄)-alkynyl, (C₁-C₄)-alkoxy, (C₁-C₄)-haloalkoxy and (C₁-C₄)-alkylthio,
R⁵ is an aryl radical which is unsubstituted or substituted and, including substituents, has 6 to 30 carbon atoms, or a heteroaromatic radical having 1 to 4 hetero ring atoms selected from the group consisting of N, O and S which is unsubstituted or substituted and, including substituents, has 1 to 30 carbon atoms, and
(R⁶)ₙ are n substituents R⁶, where R⁶, in the case that n=1, or each of the substituents R⁶ independently of the others, in the case that n is greater than 1, is a halogen, hydroxyl, amino, nitro, carboxyl, cyano, carbamoyl, (C₁-C₆)-alkyl, (C₁-C₆)-haloalkyl, (C₁-C₄)-alkoxy-(C₁-C₄)-alkyl, (C₁-C₄)-alkylthio-(C₁-C₄)-alkyl, mono- or di-[(C₁-C₄)-alkyl]aminoalkyl, hydroxy-(C₁-C₄)-alkyl, (C₂-C₆)-alkenyl, (C₂-C₆)-haloalkenyl, (C₂-C₆)-alkynyl, (C₂-C₆)-haloalkynyl, (C₁-C₆)-alkoxy, (C₁-C₆)-haloalkoxy, (C₁-C₄)-alkoxy-(C₁-C₄)-alkoxy, (C₁-C₆)-alkylthio, [(C₁-C₆)-alkoxy]carbonyl, [(C₁-C₆)-haloalkoxy]carbonyl, (C₁-C₆)-alkanoyl, (C₁-C₆)-haloalkanoyl, mono- or di-[(C₁-C₄)-alkyl]aminocarbonyl, mono- or di-[(C₁-C₆)-acyl]amino, mono- or di-[(C₁-C₄)-alkyl]amino, N—[(C₁-C₆)-acyl]-N—[(C₁-C₆)-alkyl]amino, (C₁-C₆)-alkylsulfinyl, (C₁-C₆)-haloalkylsulfinyl, (C₁-C₆)-alkylsulfonyl, (C₁-C₆)-haloalkylsulfonyl, (C₃-C₉)-cycloalkyl or (C₅-C₉)-cycloalkenyl, where each of the two last mentioned radicals is unsubstituted or substituted by one or more radicals selected from the group consisting of halogen, (C₁-C₄)-alkyl and (C₁-C₄)-haloalkyl, and n is 0, 1, 2, 3 or 4,
onto the plants, part of the plants, plant seeds or the area where the plants grow.

2. The method as claimed in claim 1, wherein
R¹ is hydrogen, alkyl, alkenyl, alkynyl, cycloalkyl, cycloalkenyl, cycloalkynyl or aryl, where each of the 7 last mentioned radicals is unsubstituted or substituted and, including substituents, has up to 30 carbon atoms or a heterocyclyl radical having 3 to 9 ring atoms which contains 1 to 4 heteroatoms selected from the group consisting of N, O and S and which is optionally substituted and, including substituents, has 1 to 30 carbon atoms, or a radical of the formula SiRᵃRᵇRᶜ, —NRᵃRᵇ or —N=CRᶜRᵈ, where in the 3 last mentioned formulae each of the radicals Rᵃ, Rᵇ, Rᶜ and Rᵈ independently of the others is hydrogen, (C₁-C₄)-alkyl, (C₂-C₄)-alkenyl, (C₂-C₄)-alkynyl, benzyl, substituted benzyl, phenyl or substituted phenyl or Rᵃ and Rᵇ together with the nitrogen atom are a 3- to 8-membered heterocycle which, in addition to the nitrogen atom, may contain one or two further hetero ring atoms selected from the group consisting of N, O and S and which is unsubstituted or substituted by one or more radicals selected from the group consisting of (C₁-C₄)-alkyl and (C₁-C₄)-haloalkyl, or Rᶜ and Rᵈ together with the carbon atom are a 3- to 8-membered carbocyclic radical or heterocyclic radical which may contain 1 to 3 hetero ring atoms selected from the group consisting of N, O and S, where the carbocyclic or heterocyclic radical is unsubstituted or substituted by one or more radicals selected from the group consisting of (C₁-C₄)-alkyl and (C₁-C₄)-haloalkyl,
R² is hydrogen, halogen or (C₁-C₄)-alkyl which is unsubstituted or substituted by one or more halogen radicals,
R³ is hydrogen, halogen or (C₁-C₄)-alkyl which is unsubstituted or substituted by one or more radicals selected from the group consisting of halogen or $R^2$ and $R^3$ together with the carbon atom to which they are attached are $(C_3-C_6)$-cycloalkyl or $(C_5-C_6)$-cycloalkenyl, where each of the 2 last mentioned radicals is unsubstituted or substituted by one or more radicals selected from the group consisting of halogen and $(C_1-C_4)$-alkyl, $R^4$ is hydrogen, halogen, cyano, $(C_1-C_4)$-alkyl, $(C_2-C_4)$-alkenyl or $(C_2-C_4)$-alkynyl, where each of the three last mentioned radicals is unsubstituted or substituted by one or more radicals selected from the group consisting of halogen and $(C_3-C_6)$-cycloalkyl which is unsubstituted or substituted by one or more radicals selected from the group consisting of halogen and $(C_1-C_4)$-alkyl, or phenyl which is unsubstituted or substituted by one or more radicals selected from the group consisting of halogen, nitro, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $[(C_1-C_4)$-alkoxy]carbonyl and $[(C_1-C_4)$-haloalkoxy]carbonyl, or $(C_1-C_4)$-alkanoyl which is unsubstituted or substituted by one or more radicals selected from the group consisting of halogen, cyano, $(C_1-C_4)$-alkoxy, $(C_1-C_4)$-haloalkoxy and $(C_1-C_2)$-alkoxy-$(C_1-C_2)$-alkoxy, or $[(C_1-C_4)$-alkoxy]carbonyl which is unsubstituted or substituted by one or more radicals selected from the group consisting of halogen, or $[(C_3-C_6)$-cycloalkoxy]carbonyl which is unsubstituted or substituted by one or more radicals selected from the group consisting of halogen and $(C_1-C_4)$-alkyl, and $R^5$ is phenyl which is unsubstituted or substituted by one or more radicals selected from the group consisting of halogen, hydroxyl, amino, nitro, carboxyl, cyano, carbamoyl, $(C_1-C_6)$-alkyl, $(C_1-C_6)$-haloalkyl, $(C_1-C_4)$-alkoxy-$(C_1-C_4)$-alkyl, $(C_1-C_4)$-alkylthio-$(C_1-C_4)$-alkyl, mono- and di-$[(C_1-C_4)$-alkyl]aminoalkyl, hydroxy-$(C_1-C_4)$-alkyl, carboxy-$(C_1-C_4)$-alkyl, cyano-$(C_1-C_4)$-alkyl, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- and di-$[(C_1-C_4)$-alkyl]aminocarbonyl, mono- and di-$[(C_1-C_6)$-acyl]amino, mono- and di-$[(C_1-C_4)$-alkyl]amino, N—$[(C_1-C_6)$-acyl]-N—$[(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_3-C_6)$-cycloalkyl, $(C_3-C_6)$-cycloalkyloxy, phenyl and phenoxy, where each of the 4 last mentioned radicals is unsubstituted or substituted by one or more radicals selected from the group consisting of halogen, $(C_1-C_4)$-alkyl and $(C_1-C_4)$-haloalkyl, and where two adjacent substituents may form a fused-on 5- or 6-membered ring which is carbocyclic or may additionally contain 1 to 3 hetero ring atoms selected from the group consisting of N, O and S and which is unsubstituted or substituted by one or more radicals selected from the group consisting of halogen and $(C_1-C_6)$-alkyl, or a 5- or 6-membered heteroaromatic ring having 1 to 3 hetero ring atoms selected from the group consisting of N, O and S, which is unsubstituted or substituted by one or more radicals selected from the group consisting of halogen, hydroxyl, amino, nitro, carboxyl, cyano, carbamoyl, $(C_1-C_6)$-alkyl, $(C_1-C_6)$-haloalkyl, $(C_1-C_4)$-alkoxy-$(C_1-C_4)$-alkyl, $(C_1-C_4)$-alkylthio-$(C_1-C_4)$-alkyl, mono- and di-$[(C_1-C_4)$-alkyl]aminoalkyl, hydroxy-$(C_1-C_4)$-alkyl, carboxy-$(C_1-C_4)$-alkyl, cyano-$(C_1-C_4)$-alkyl, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- and di-$[(C_1-C_4)$-alkyl]aminocarbonyl, mono- and di-$[(C_1-C_6)$-acyl]amino, mono- and di-$[(C_1-C_4)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_3-C_6)$-cycloalkyl, $(C_3-C_6)$-cycloalkyloxy, phenyl and phenoxy, where each of the 4 last mentioned radicals is unsubstituted or substituted by one or more radicals selected from the group consisting of halogen, $(C_1-C_4)$-alkyl and $(C_1-C_4)$-haloalkyl, and $(R^6)_n$ are n substituents $R^6$, where $R^6$, in the case that n=1, or each of the substituents $R^6$ independently of the others, in the case that n is greater than 1, is a radical halogen, $(C_1-C_4)$-alkyl, $(C_1-C_4)$-haloalkyl, $(C_1-C_4)$-alkoxy, $(C_1-C_4)$-alkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl, and n is 0, 1, 2, 3 or 4.

3. The method as claimed in claim 1, wherein $R^1$ is H, $(C_1-C_{18})$-alkyl, $(C_2-C_{18})$-alkenyl, $(C_2-C_{18})$-alkynyl, $(C_3-C_9)$-cycloalkyl, $(C_5-C_9)$-cycloalkenyl, $(C_5-C_9)$-cycloalkynyl, or phenyl, where each of the 7 last mentioned radicals is unsubstituted or substituted by one or more radicals selected from the group consisting of halogen, cyano, thio, nitro, hydroxyl, $(C_1-C_8)$-alkyl, $(C_1-C_8)$-haloalkyl, $(C_1-C_4)$-alkoxy-$(C_1-C_4)$-alkyl, $(C_2-C_8)$-alkenyl, $(C_2-C_8)$-haloalkenyl, $(C_2-C_8)$-alkynyl, $(C_2-C_8)$-haloalkynyl, the 7 last mentioned radicals only in the case of cyclic base radicals, $(C_1-C_8)$-alkoxy, $(C_2-C_8)$-alkenyloxy, $(C_2-C_8)$-alkynyloxy, $(C_1-C_8)$-haloalkoxy, $(C_1-C_4)$-alkoxy-$(C_1-C_4)$-alkoxy, $(C_1-C_8)$-alkylthio, $(C_2-C_8)$-alkenylthio, $(C_2-C_8)$-alkynylthio, radicals of the formulae —NR*R**, —CO—NR*R** and —O—CO—NR*R**, where each of the radicals R* and R** in the 3 last mentioned formulae independently of the others is H, $(C_1-C_8)$-alkyl, $(C_2-C_8)$-alkenyl, $(C_2-C_8)$-alkynyl, benzyl, substituted benzyl, phenyl or substituted phenyl, or together with the nitrogen atom is a 3- to 8-membered heterocycle which, in addition to the nitrogen atom, may contain one or two further hetero ring atoms selected from the group consisting of N, O and S and which is unsubstituted or substituted by one or more radicals selected from the group consisting of $(C_1-C_4)$-alkyl and $(C_1-C_4)$-haloalkyl, and $[(C_1-C_8)$-alkoxy]carbonyl, $[(C_1-C_8)$-alkoxy]thiocarbonyl, $[(C_2-C_8)$-alkenyloxy]carbonyl, $[(C_2-C_8)$-alkynyloxy]carbonyl, $[(C_1-C_8)$-alkylthio]carbonyl, $[(C_2-C_8)$-alkenylthio]carbonyl, $[(C_2-C_8)$-alkynylthio]carbonyl, $(C_1-C_8)$-alkanoyl, $[(C_2-C_8)$-alkenyl]carbonyl, $[(C_2-C_8)$-alkynyl]carbonyl, $(C_1-C_4)$-alkylimino, $(C_1-C_4)$-alkoxyimino, $[(C_1-C_8)$-alkyl]carbonylamino, $[(C_2-C_8)$-alkenyl]carbonylamino, $[(C_2-C_8)$-alkynyl]carbonylamino, $[(C_1-C_8)$-alkoxy]carbonylamino, $[(C_2-C_8)$-alkenyloxy]carbonylamino, $[(C_2-C_8)$-alkynyloxy]carbonylamino, $[(C_1-C_8)$-alkylamino]carbonylamino, $[(C_1-C_6)$-alkyl]carbonyloxy, $[(C_2-C_6)$-alkenyl]carbonyloxy, $[(C_2-C_6)$-alkynyl]carbonyloxy, $[(C_1-C_8)$-alkoxy]carbonyloxy, $[(C_2-C_8)$-alkenyloxy]carbonyloxy, $[(C_2-C_8)$-alkynyloxy]carbonyloxy, $(C_1-C_8)$-alkylsulfinyl and $(C_1-C_8)$-alkylsulfonyl, where each of the 27 last mentioned radicals is unsubstituted or substituted by one or more radicals selected from the group consisting of halogen, $NO_2$, $(C_1-C_4)$-alkoxy and optionally substituted phenyl, and phenyl, phenyl-$(C_1-C_6)$-alkoxy, phenyl-$[(C_1-C_6)$-alkoxy]carbonyl, phenoxy, phenoxy-$(C_1-C_6)$-alkoxy, phenoxy-$[(C_1-C_6)$-alkoxy]carbonyl, phenoxycarbonyl, phenylcarbonyloxy, phenylcarbonylamino, phenyl-$[(C_1-C_6)$-alkyl]

carbonylamino, phenyl-[($C_1$-$C_6$)-alkyl]carbonyloxy, ($C_3$-$C_7$)-cycloalkyl and ($C_3$-$C_7$)-cycloalkoxy, where each of the 13 last mentioned radicals is unsubstituted in the ring or substituted by one or more radicals selected from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, and radicals of the formulae —SiR'$_3$, —O—SiR'$_3$, (R')$_3$Si—($C_1$-$C_6$)-alkoxy, —CO—O—NR'$_2$, —O—N=CR'$_2$, —N=CR'$_2$, —O—NR'$_2$, —CH(OR')$_2$ and —O—(CH$_2$)$_m$—CH(OR')$_2$, in which each of the radicals R' independently of the others is H, ($C_1$-$C_4$)-alkyl or phenyl which is unsubstituted or substituted by one or more radicals selected from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or substituted in two adjacent positions by a ($C_2$-$C_6$)-alkylene bridge, and m is an integer of from 0 to 6, and radicals of the formula R'''O—CHR'''CH(OR'')—($C_1$-$C_6$)-alkoxy, in which each of the radicals R'' independently of the others is H or ($C_1$-$C_4$)-alkyl or the radicals R'' together are a ($C_1$-$C_6$)-alkylene group and R''' is H or ($C_1$-$C_4$)-alkyl.

4. The method as claimed in claim 1, wherein
$R^2$ is hydrogen, methyl or ethyl,
$R^3$ is hydrogen or methyl,
$R^4$ is hydrogen, halogen, cyano, ($C_1$-$C_4$)-alkyl, ($C_1$-$C_4$)-hydroxyalkyl, ($C_1$-$C_4$)-haloalkyl, cyclopropyl or cyclobutyl, where each of the two last mentioned radicals is unsubstituted or substituted by one or more radicals selected from the group consisting of halogen and ($C_1$-$C_4$)-alkyl, or phenyl which is unsubstituted or substituted by one or more radicals selected from the group consisting of halogen, ($C_1$-$C_4$)-alkyl, ($C_1$-$C_4$)-haloalkyl, ($C_1$-$C_4$)-alkoxy and ($C_1$-$C_4$)-alkylthio, or ($C_1$-$C_4$)-alkanoyl which is unsubstituted or substituted by one or more radicals selected from the group consisting of halogen, or [($C_1$-$C_4$)-alkoxy]carbonyl or [($C_1$-$C_4$)-haloalkoxy]carbonyl,
$R^5$ is phenyl which is unsubstituted or substituted by one or more radicals selected from the group consisting of halogen, hydroxyl, nitro, carboxyl, cyano, ($C_1$-$C_4$)-alkyl, ($C_1$-$C_4$)-haloalkyl, ($C_1$-$C_4$)-alkoxy-($C_1$-$C_4$)-alkyl, ($C_1$-$C_4$)-alkylthio-($C_1$-$C_4$)-alkyl, hydroxy-($C_1$-$C_4$)-alkyl, ($C_1$-$C_4$)-alkoxy, ($C_1$-$C_4$)-haloalkoxy, ($C_1$-$C_4$)-alkoxy-($C_1$-$C_4$)-alkoxy, ($C_1$-$C_4$)-alkylthio, [($C_1$-$C_4$)-alkoxy]carbonyl, [($C_1$-$C_6$)-haloalkoxy]carbonyl, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl, ($C_3$-$C_6$)-cycloalkyl, ($C_3$-$C_6$)-cycloalkyloxy, phenyl and phenoxy, where each of the 4 last mentioned radicals is unsubstituted or substituted by one or more radicals selected from the group consisting of halogen, ($C_1$-$C_4$)-alkyl and ($C_1$-$C_4$)-haloalkyl, and where two adjacent substituents may form a fused-on 5- or 6-membered ring which is carbocyclic and may additionally contain 1 to 3 hetero ring atoms selected from the group consisting of N, O and S and which is unsubstituted or substituted by one or more radicals selected from the group consisting of halogen and ($C_1$-$C_4$)-alkyl, or a 5- or 6-membered heteroaromatic radical having 1 to 3 hetero ring atoms selected from the group consisting of N, O and S, which is unsubstituted or substituted by one or more radicals selected from the group consisting of halogen, hydroxyl, carboxyl, cyano, ($C_1$-$C_4$)-alkyl, ($C_1$-$C_4$)-haloalkyl, ($C_1$-$C_4$)-alkoxy-($C_1$-$C_4$)-alkyl, ($C_1$-$C_4$)-alkylthio-($C_1$-$C_4$)-alkyl, hydroxy-($C_1$-$C_4$)-alkyl, ($C_1$-$C_4$)-alkoxy, ($C_1$-$C_4$)-haloalkoxy, ($C_1$-$C_4$)-alkoxy-($C_1$-$C_4$)-alkoxy, ($C_1$-$C_4$)-alkylthio, [($C_1$-$C_6$)-alkoxy]carbonyl, [($C_1$-$C_6$)-haloalkoxy]carbonyl, ($C_1$-$C_4$)-alkylsulfinyl, ($C_1$-$C_4$)-haloalkylsulfinyl, ($C_1$-$C_4$)-alkylsulfonyl, ($C_1$-$C_4$)-haloalkylsulfonyl and ($C_3$-$C_6$)-cycloalkyl which is unsubstituted or substituted by one or more radicals selected from the group consisting of halogen, ($C_1$-$C_4$)-alkyl and ($C_1$-$C_4$)-haloalkyl, and ($R^6$)$_n$ are n substituents $R^6$, where $R^6$, in the case that n=1, or each of the substituents $R^6$ independently of the others, in the case that n is greater than 1, is halogen, methyl, ethyl, $CF_3$, methoxy, ethoxy, methylthio, methylsulfinyl, ethylsulfinyl, methylsulfonyl or ethylsulfonyl, and n is 0, 1, 2, 3 or 4.

5. The method according to claim 1, wherein the compounds of the formula (I) or salts thereof are employed for controlling harmful plants or for regulating the growth in crops of useful plants or ornamental plants.

6. The method according to claim 5, wherein the crop plants are transgenic crop plants.

7. A herbicidal or plant growth-regulating composition which comprises one or more compounds of the formula (I) or salts thereof

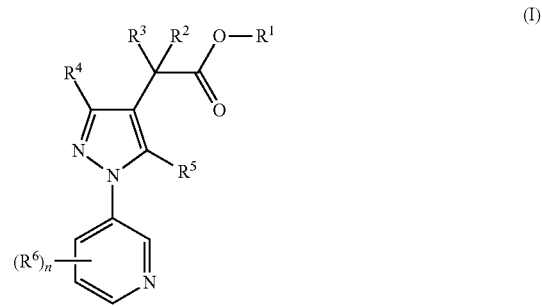

(I)

wherein
$R^1$ is hydrogen or a hydrolyzable radical,
$R^2$ is hydrogen, halogen or ($C_1$-$C_6$)-alkyl which is unsubstituted or substituted by one or more radicals selected from the group consisting of halogen, ($C_1$-$C_4$)-alkoxy, ($C_1$-$C_4$)-alkylthio and ($C_1$-$C_4$)-haloalkoxy,
$R^3$ is hydrogen, halogen or ($C_1$-$C_6$)-alkyl which is unsubstituted or substituted by one or more radicals selected from the group consisting of halogen, ($C_1$-$C_4$)-alkoxy, ($C_1$-$C_4$)-alkylthio and ($C_1$-$C_4$)-haloalkoxy, or $R^2$ and $R^3$ together with the carbon atom to which they are attached are a carbocyclic saturated or partially unsaturated ring having 3 to 6 carbon atoms which is unsubstituted or substituted by one or more radicals selected from the group consisting of halogen and ($C_1$-$C_4$)-alkyl,
$R^4$ is hydrogen, halogen, cyano, ($C_1$-$C_6$)-alkyl, ($C_1$-$C_6$)-alkenyl or ($C_2$-$C_6$)-alkynyl, where each of the three last mentioned radicals is unsubstituted or substituted by one or more radicals selected from the group consisting of halogen, cyano, hydroxyl, ($C_1$-$C_4$)-alkoxy, ($C_1$-$C_4$)-haloalkoxy, ($C_1$-$C_4$)-alkoxy-($C_1$-$C_4$)-alkoxy, ($C_1$-$C_4$)-alkylthio and optionally halogen-, cyano-, ($C_1$-$C_4$)-alkyl- or ($C_1$-$C_4$)-haloalkyl-substituted ($C_3$-$C_9$)-cycloalkyl, or ($C_3$-$C_9$)-cycloalkyl, ($C_5$-$C_9$)-cycloalkenyl or ($C_5$-$C_9$)-cycloalkynyl, where each of the 3 last mentioned radicals is unsubstituted or substituted by one or more radicals selected from the group consisting of halogen, ($C_1$-$C_4$)-alkyl, ($C_1$-$C_4$)-haloalkyl, ($C_7$-$C_4$)-alkenyl, ($C_1$-$C_4$)-alkynyl, ($C_1$-$C_4$)-alkoxy, ($C_1$-$C_4$)-haloalkoxy and ($C_1$-$C_4$)-alkylthio, or phenyl which is unsubstituted or substituted by one or more radicals selected from the group consisting of halogen, cyano, nitro, carboxyl, $(C_1-C_4)$-alkyl, $(C_1-C_4)$-haloalkyl, $(C_7-C_4)$-alkenyl, $(C_1-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_1-C_4)$-alkanoyl, $(C_1-C_4)$-haloalkanoyl, [$(C_1-C_4)$-alkoxy]carbonyl and [$(C_1-C_4)$-haloalkoxy]carbonyl, or $(C_1-C_6)$-alkanoyl which is unsubstituted or substituted by one or more radicals selected from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$ alkyl- or $(C_1-C_4)$-haloalkyl-substituted $(C_3-C_6)$-cycloalkyl, or [$(C_1-C_4)$-alkoxy]carbonyl which is unsubstituted or substituted by one or more radicals selected from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4$-alklthio and optionally halogen-, cyano-, $(C_1-C_4)$-alkyl- or $(C_1-C_4)$-haloalkyl-substituted $(C_3-C_6)$-cycloalkyl, or [$(C_3-C_9)$-cycloalkoxy]carbonyl which is unsubstituted or substituted by one or more radicals selected from the group consisting of halogen, $(C_1-C_4)$-alkyl, $(C_1-C_4)$-haloalkyl, $(C_2-C_4)$-alkenyl, $(C_7-C_4)$-alkynyl, $(C_1-C_4)$-alkoxy, $(C_1-C_4)$-haloalkoxy and $(C_1-C_4)$-alkylthio, $R^5$ is an aryl radical which is unsubstituted or substituted and, including substituents, has 6 to 30 carbon atoms, or a heteroaromatic radical having 1 to 4 hetero ring atoms selected from the group consisting of N, O and S which is unsubstituted or substituted and, including substituents, has 1 to 30 carbon atoms, and $(R^6)_n$ are n substituents $R^6$, where $R^6$, in the case that n=1, or each of the substituents $R^6$ independently of the others, in the case that n is greater than 1, is a halogen, hydroxyl, amino, nitro, carboxyl, cyano, carbamoyl, $(C_1-C_6)$-alkyl, $(C_1-C_6)$-haloalkyl, $(C_1-C_4)$-alkoxy-$(C_1-C_4)$-alkyl, $(C_1-C_4)$-alkylthio-$(C_1-C_4)$-alkyl, mono- or di-[$(C_1-C_4)$-alkyl]amino alkyl, hydroxy-$(C_1-C_4)$-alkyl, $(C_7-C_6)$-alkenyl, $(C_7-C_6)$-haloalkenyl, $(C_2-C_6)$-alkynyl, $(C_2-C_6)$-haloalkynyl, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, [$(C_1-C_6)$-alkoxy]carbonyl, [$(C_1-C_6)$-haloalkoxy]carbonyl, $(C_1-C_6)$-alkanoyl, $(C_1-C_6)$-haloalkanoyl, mono- or di-[$(C_1-C_4)$-alkyl]aminocarbonyl, mono- or di-[$(C_1-C_6)$-acyl]amino, mono- or di-[$(C_1-C_4)$-alkyl]amino, N—[$(C_1-C_6)$-acyl]-N—[$(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_3-C_9)$-cycloalkyl or $(C_5-C_9)$-cycloalkenyl, where each of the two last mentioned radicals is unsubstituted or substituted by one or more radicals selected from the group consisting of halogen, $(C_1-C_4)$-alkyl and $(C_1-C_4)$-haloalkyl, and n is 0, 1, 2, 3 or 4, and formulation auxiliaries customary in crop protection.

\* \* \* \* \*